(12) United States Patent
Hallahan

(10) Patent No.: US 10,449,261 B2
(45) Date of Patent: Oct. 22, 2019

(54) COMPOSITIONS TARGETING RADIATION-INDUCED MOLECULES AND METHODS OF USE THEREOF

(71) Applicant: Washington University, St. Louis, MO (US)

(72) Inventor: Dennis E. Hallahan, St. Louis, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

(21) Appl. No.: 15/328,829

(22) PCT Filed: Jul. 24, 2015

(86) PCT No.: PCT/US2015/041986
§ 371 (c)(1),
(2) Date: Jan. 24, 2017

(87) PCT Pub. No.: WO2016/014939
PCT Pub. Date: Jan. 28, 2016

(65) Prior Publication Data
US 2017/0209603 A1    Jul. 27, 2017

Related U.S. Application Data

(60) Provisional application No. 62/028,771, filed on Jul. 24, 2014.

(51) Int. Cl.
| | | |
|---|---|---|
| *A61K 49/00* | (2006.01) | |
| *A61K 51/08* | (2006.01) | |
| *A61K 51/06* | (2006.01) | |
| *A61K 47/60* | (2017.01) | |
| *A61K 47/64* | (2017.01) | |
| *A61N 5/10* | (2006.01) | |

(52) U.S. Cl.
CPC ............ *A61K 51/088* (2013.01); *A61K 47/60* (2017.08); *A61K 47/64* (2017.08); *A61K 51/065* (2013.01); *A61N 2005/1098* (2013.01)

(58) Field of Classification Search
CPC ...... A61K 51/00; A61K 51/08; A61K 51/088; A61K 51/065; A61K 2121/00; A61K 2123/00; A61K 38/00; A61K 47/00; A61K 47/60; A61K 47/64; A61N 2005/1098
USPC .......... 424/1.11, 1.65, 1.69, 1.81, 1.85, 1.89, 424/9.1, 9.2, 9.3, 9.4, 9.5, 9.6; 514/1, 514/1.1; 530/300; 534/7, 10–16
See application file for complete search history.

(56) References Cited

U.S. PATENT DOCUMENTS

| | | |
|---|---|---|
| 4,241,046 A | 12/1980 | Papahadjopoulos |
| 4,244,946 A | 1/1981 | Rivier |
| 4,281,061 A | 7/1981 | Zuk |
| 4,394,448 A | 7/1983 | Szoka et al. |
| 4,515,165 A | 5/1985 | Carroll |
| 4,529,561 A | 7/1985 | Hunt et al. |
| 4,551,482 A | 11/1985 | Tschang et al. |
| 4,619,823 A | 10/1986 | Yokoyama et al. |
| 4,670,386 A | 6/1987 | Sugaar |
| 4,741,900 A | 5/1988 | Alvarez et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Mueller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,093,104 A | 3/1992 | Kaminsky |
| 5,223,409 A | 6/1993 | Ladner et al. |
| 5,264,563 A | 11/1993 | Huse |
| 5,264,618 A | 11/1993 | Felgner et al. |
| 5,277,892 A | 1/1994 | Rhodes |
| 5,292,524 A | 3/1994 | Male et al. |
| 5,328,840 A | 7/1994 | Coller |
| 5,334,369 A | 8/1994 | Halushka et al. |
| 5,382,680 A | 1/1995 | Abraham et al. |
| 5,490,840 A | 2/1996 | Uzgiris et al. |
| 5,510,103 A | 4/1996 | Yokoyama et al. |
| 5,516,881 A | 5/1996 | Lee et al. |
| 5,574,172 A | 11/1996 | Katsuro et al. |
| 5,614,535 A | 3/1997 | Juraszyk |
| 5,645,815 A | 7/1997 | Dean |
| 5,651,991 A | 7/1997 | Sugiyama et al. |
| 5,688,931 A | 11/1997 | Nogusa et al. |
| 5,693,627 A | 12/1997 | Schieven |
| 5,714,166 A | 2/1998 | Tomalia et al. |
| 5,753,627 A | 5/1998 | Albert et al. |

(Continued)

FOREIGN PATENT DOCUMENTS

| | | |
|---|---|---|
| DE | 2621311 A1 | 11/1976 |
| EP | 0229718 B1 | 4/1991 |

(Continued)

OTHER PUBLICATIONS

Karmali, P. et al., "Targeting of albumin-embedded paclitaxel nanoparticles to tumors," NIH Public Access Author Manuscript, available in PMC Mar. 1, 2010, pp. 1-16, Published in final edited form as: Nanomedicine, Mar. 2009, pp. 73-82, vol. 5, No. 1.

(Continued)

*Primary Examiner* — D. L. Jones
(74) *Attorney, Agent, or Firm* — Polsinelli PC

(57) ABSTRACT

The present invention is directed towards the compositions of peptide constructs that bind to GRP78 and the methods of use thereof.

19 Claims, 16 Drawing Sheets
(15 of 16 Drawing Sheet(s) Filed in Color)
Specification includes a Sequence Listing.

(56) References Cited

U.S. PATENT DOCUMENTS

| | | |
|---|---|---|
| 5,759,542 A | 6/1998 | Gurewich |
| 5,776,427 A | 7/1998 | Thorpe |
| 5,786,387 A | 7/1998 | Watanabe et al. |
| 5,830,856 A | 11/1998 | Dean |
| 5,855,866 A | 1/1999 | Thorpe |
| 5,855,900 A | 1/1999 | Nobuhiko |
| 5,858,410 A | 1/1999 | Muller et al. |
| 5,863,538 A | 1/1999 | Thorpe |
| 5,889,169 A | 3/1999 | Beach |
| 5,922,356 A | 7/1999 | Koseki et al. |
| 5,922,545 A | 7/1999 | Mattheakis et al. |
| 5,962,424 A | 10/1999 | Hallahan et al. |
| 5,965,132 A | 10/1999 | Thorpe |
| 5,977,313 A | 11/1999 | Heath |
| 5,994,392 A | 11/1999 | Shashoua |
| 6,004,554 A | 12/1999 | Thorpe |
| 6,015,561 A | 1/2000 | Alvarez |
| 6,015,881 A | 1/2000 | Kang et al. |
| 6,031,071 A | 2/2000 | Mandeville et al. |
| 6,033,847 A | 3/2000 | Sherr |
| 6,051,230 A | 4/2000 | Thorpe |
| 6,068,829 A | 5/2000 | Ruoslahti |
| 6,106,866 A | 8/2000 | Ranney |
| 6,107,059 A | 8/2000 | Hart |
| 6,127,339 A | 10/2000 | Hatanaka et al. |
| 6,156,511 A | 12/2000 | Schatz |
| 6,156,736 A | 12/2000 | Weichselbaum |
| 6,159,443 A | 12/2000 | Hallahan |
| 6,174,687 B1 | 1/2001 | Rajotte |
| 6,232,287 B1 | 5/2001 | Ruoslahti et al. |
| 6,261,535 B1 | 7/2001 | Thorpe |
| 6,277,974 B1 | 8/2001 | Lo et al. |
| 6,316,208 B1 | 11/2001 | Roberts |
| 6,383,470 B1 | 5/2002 | Fritzsch |
| 6,403,383 B1 | 6/2002 | Casterlin |
| 6,576,239 B1 | 6/2003 | Ruoslahti |
| 6,605,712 B1 | 8/2003 | Weichselbaum |
| 6,630,570 B1 | 10/2003 | Licha et al. |
| 6,673,545 B2 | 1/2004 | Faris et al. |
| 7,018,615 B2 | 3/2006 | Ruoslahti |
| 7,018,618 B2 | 3/2006 | Lewis et al. |
| 7,049,140 B1 | 5/2006 | Hallahan |
| 7,056,506 B2 | 6/2006 | Varner |
| 7,122,361 B2 | 10/2006 | Liu et al. |
| 7,138,238 B2 | 11/2006 | Vodyanoy |
| 7,230,083 B2 | 6/2007 | Jonak et al. |
| 7,230,088 B2 | 6/2007 | Rajagopalan et al. |
| 7,306,925 B2 | 12/2007 | Hallahan |
| 7,402,392 B2 | 7/2008 | Hallahan |
| 7,875,454 B2 | 1/2011 | Hallahan |
| 7,906,102 B2 | 3/2011 | Hallahan |
| 7,968,675 B2 | 6/2011 | Hallahan |
| 8,012,945 B2 | 9/2011 | Hallahan et al. |
| 8,101,157 B2 | 1/2012 | Hallahan |
| 8,388,932 B2 | 3/2013 | Hallahan et al. |
| 8,617,521 B2 | 12/2013 | Hallahan et al. |
| 8,765,097 B2 | 7/2014 | Hallahan et al. |
| 8,927,288 B2 | 1/2015 | Hallahan et al. |
| 9,340,581 B2 | 5/2016 | Hallahan |
| 10,086,073 B2 | 10/2018 | Hallahan et al. |
| 2002/0086288 A1 | 7/2002 | Bird et al. |
| 2002/0164663 A1 | 11/2002 | Fuqua et al. |
| 2003/0027159 A1 | 2/2003 | Ward et al. |
| 2003/0083261 A1 | 5/2003 | Yu et al. |
| 2003/0130190 A1 | 7/2003 | Hallahan et al. |
| 2003/0157025 A1 | 8/2003 | Unger et al. |
| 2003/0157482 A1 | 8/2003 | Keesee |
| 2004/0191249 A1 | 9/2004 | Hallahan et al. |
| 2006/0046271 A1 | 3/2006 | Hallahan |
| 2006/0104898 A1 | 5/2006 | Hallahan |
| 2006/0188442 A1 | 8/2006 | Hallahan |
| 2007/0065361 A1 | 3/2007 | Hallahan |
| 2007/0081993 A1 | 4/2007 | Kufer et al. |
| 2008/0003200 A1 | 1/2008 | Arap et al. |
| 2008/0118978 A1 | 5/2008 | Sato et al. |
| 2008/0187488 A1 | 8/2008 | Hallahan et al. |
| 2008/0206130 A1 | 8/2008 | Hallahan et al. |
| 2008/0305111 A1 | 12/2008 | Evans et al. |
| 2010/0039023 A1 | 2/2010 | Rogojevic et al. |
| 2010/0041074 A1 | 2/2010 | Kimura |
| 2010/0111852 A1 | 5/2010 | Yoshida |
| 2010/0111959 A1 | 5/2010 | Swanson et al. |
| 2010/0135905 A1 | 6/2010 | Hallahan et al. |
| 2010/0221183 A1 | 9/2010 | Squires |
| 2011/0213293 A1 | 9/2011 | Hallahan et al. |
| 2012/0041303 A1 | 2/2012 | Hallahan et al. |
| 2012/0089017 A1 | 4/2012 | Hallahan et al. |
| 2013/0251628 A1 | 9/2013 | Hallahan et al. |
| 2014/0088408 A1 | 3/2014 | Hallahan et al. |
| 2014/0369929 A1 | 12/2014 | Hallahan et al. |
| 2016/0206736 A1 | 7/2016 | Hallahan et al. |

FOREIGN PATENT DOCUMENTS

| | | |
|---|---|---|
| EP | 0723156 A2 | 7/1996 |
| EP | 0723156 A3 | 4/1998 |
| EP | 1217377 B1 | 6/2002 |
| WO | 1986005693 A1 | 10/1986 |
| WO | 1991001144 A1 | 2/1991 |
| WO | 1992020796 A2 | 11/1992 |
| WO | 1993006835 A1 | 4/1993 |
| WO | 1993014791 A2 | 8/1993 |
| WO | 1993020229 A1 | 10/1993 |
| WO | 1995033496 A1 | 12/1995 |
| WO | 1995034315 A1 | 12/1995 |
| WO | 1996012956 A1 | 5/1996 |
| WO | 1996025947 A2 | 8/1996 |
| WO | 1998010795 A3 | 3/1998 |
| WO | 1999004238 A2 | 1/1999 |
| WO | 2000066182 A1 | 11/2000 |
| WO | 2001009611 A2 | 2/2001 |
| WO | 2001009611 A3 | 7/2001 |
| WO | 2003028640 A2 | 4/2003 |
| WO | 2005042780 A1 | 5/2005 |
| WO | 2006028993 A2 | 3/2006 |
| WO | 2007011680 A2 | 1/2007 |
| WO | 2013019730 A1 | 2/2013 |
| WO | 2013049830 A2 | 4/2013 |
| WO | 2016014939 A1 | 1/2016 |

OTHER PUBLICATIONS

Kastan, M. et al., "ATM kinase modulation for screening and therapies," Database HCAPLUS on STN, 2000, Abstract WO00/47760, Accession No. 2000:573954, Registry No. 288259-02-9 for SEQ ID No. 8 and SEQ ID No. 10 and Registry No. 288259-18-7 for SEQ ID No. 13, 1 pg.

Katanasaka, Y., et al., Cancer antineovascular therapy with liposome drug delivery systems targeted to BiP/GRP78, Int. J. Cancer, 2010, pp. 2685-2698, vol. 127, No. 11.

Kelley, M. et al., "CDKN2 in HPV-Positive and HPV-Negative Cervical-Carcinoma Cell Lines," Int. J. Cancer, 1995 pp. 226-230, vol. 63.

Kern, J., et al., "GRP-78 secreted by tumor cells blocks the antiangiogenic activity of bortezomib," Blood, Oct. 29, 2009, pp. 3960-3967, vol. 114, No. 18, The American Society of Hematology.

Khleif, S. et al., "Inhibition of cyclin D-CDK4/CDK6 activity is associated with an E2F-mediated induction of cyclin kinase inhibitor activity," PNAS, Apr. 1996, pp. 4350-4354, vol. 93.

Kim, J. et al., "Absence of p15INK48 and p16INK4A Gene Alterations in Primary Cervical Carcinoma Tissues and Cell Lines with Human Papillomavirus Infection," Gynecologic Oncology, 1998, pp. 75-79, vol. 70, Article No. GO985041.

Kim, Y. et al., "Underexpression of Cyclin-Dependent Kinase (CDK) Inhibitors in Cervical Carcinoma," Gynecologic Oncology, 1998, pp. 38-45, vol. 71, Article No. GO985134.

Klaes, R. et al., "Overexpression of p16INK4A as a Specific Marker for Dysplastic and Neoplastic Epthelial Cells of the Cervis Uteri," Int. J. Cancer, 2001, pp. 276-284, vol. 92.

(56) References Cited

OTHER PUBLICATIONS

Koivunen, E. et al., "Isolation of a Highly Specific Ligand for the alpha5beta 1 Integrin from a Phage Display Library," J. Cell Biol., 1994, pp. 373-380, vol. 124.

Koivunen, E. et al., "Selection of Peptides Binding to the alpha5beta 1 Integrin from Phage Display Library," J. Bio. Chem., Sep. 25, 1993, pp. 20205-20210, vol. 268, No. 27.

Krauer, K. et al., "Antitumor Effect of 2'-Deoxy-5-fluorouridine Conjugates against a Murine Thymoma and Colon Carcinoma Xenografts," Cancer Res., Jan. 1, 1992, pp. 132-137, vol. 52.

Kruskal, W. et al., "Use of Ranks in One-Criteria Variance Analysis," J. Am. Stat. Assoc., Dec. 1952, pp. 583-621, vol. 47, No. 260.

Kurnik, B. et al., "Prospective study of atrial natriuretic peptide for the prevention of radio-contrast-induced nephropathy," Database HCAPLUS on STN, Abstract, Am. J. Kidney Disease, 1998, Accession No. 1998:248017, Registry No. 95896-08-5 for atrial natriuetic peptide-25, for SEQ ID No. 11, 1 pg.

Lee, A., "GRP78 induction in Cancer: Therapeutic and Prognostic Implications," Cancer Res, Apr. 15, 2007, pp. 3496-3499, vol. 67, No. 8, American Association for Cancer Research.

Li, J. et al., "Stress Induction of GRP78/BiP and Its Role in Cancer," Curr. Mol. Med., Feb. 2006, pp. 45-54, vol. 6, No. 1, Bentham Science Publishers.

Lieberman, H. et al., "A human homolog of the Schizosaccharomyces pombe rad9+ checkpoint control gene," PNAS, Nov. 1996, pp. 13890-13895, vol. 93.

Liggett, W. et al., "Role of the p16 Tumor Suppressor Gene in Cancer," J. Clin. Onocl., Mar. 1998, pp. 1197-1206, vol. 16, No. 3.

Liu, S. et al., "Bifunctional Chelators for Therapeutic Lanthanide Radiopharmaceuticals," Bioconjugate Chem., 2001, pp. 7-34, vol. 12, No. 1, with Correction, Bioconjugate Chem., 2001, p. 653, vol. 12, No. 4.

Liu, Y. et al., "Mechanistic Studies of a Peptidic GRP78 Ligand for Cancer Cell-Specific Drug Delivery," NIH Public Access Author Manuscript, available in PMC Sep. 10, 2008, pp. 1-22, Published in final form as: Mol. Pharm., 2007, pp. 435-447, vol. 4, No. 3.

Llovet, J. et al., "Arterial embolisation or chemoembolisation versus symptomatic treatment in patients with unresectable hepatocellular carcinoma: a randomised controlled trial," Lancet, May 18, 2002, pp. 1734-1739, vol. 359.

Lohse, J. et al., "Fluorescein-Conjugated Lysine Monomers for Solid Phase Synthesis of Fluorescent Peptides and PNA Oligomers," Bioconjugate Chem., 1997, pp. 503-509, vol. 8, No. 4, American Chemical Society.

Lowery, A. et al., "Tumor-targeted delivery of liposome-encapsulated doxorubicin by use of a peptide that selectively binds to irradiated tumors," NIH Public Access Author Manuscript, 15 pgs., J. Control Release, Feb. 28, 2011, pp. 117-124, vol. 150, No. 1.

Ma, Y. et al., "The role of the unfolded protein response in tumour development: friend or foe?," Nat. Rev. Can., Dec. 2004, pp. 966-977, vol. 4.

Maddalo, D. et al., "A Peptidic Unconjugated GRP78/BiP Ligand Modulates the Unfolded Protein Response and Induces Prostate Cancer Cell Death," PLoS ONE, Oct. 2012, pp. 1-14, vol. 7, No. 10, e45690.

Mao, C. et al., "Evaluation of a new p16INK4a ELISA test and a high-risk HPV DNA test for cervical cancer screening: Results from proof-of-concept study," Int. J. Cancer, 2007, pp. 2435-2438, vol. 120.

Martin, F., et al., "Targeted Retroviral Infection of Tumor Cells by Receptor Cooperation," J. Virology, Feb. 2003, pp. 2753-2756, vol. 77, No. 4.

Mathis, J. et al., "Oncolytic adenoviruses—selective retargeting to tumor cells," Oncogene, 2005, pp. 7775-7791, vol. 24, Nature Publishing Group.

Mauceri, H. et al., "Tumor Necrosis Factor alpha (TNF-alpha) Gene Therapy Targeted by Ionizing Radiation Selectively Damages Tumor Vasculature," Cancer Res., Oct. 1, 1996, pp. 4311-4314, vol. 56.

McCabe, J., "The effects of detergents on the enzyme-linked immunosorbent assay (ELISA) of blood group substances," J. Immunol., Methods, Apr. 1988, pp. 129-135, vol. 108, No. 1, Abstract only.

McFarland, B. et al., "Plasminogen Kringle 5 Induces Apoptosis of Brain Microvessel Endothelial Cells: Sensitization by Radiation and Requirement for GRP78 and LRP1," Cancer Res., Jul. 1, 2009, pp. 5537-5545, vol. 69, No. 13, American Association for Cancer.

Menon, R. et al., "Functional Implications of Structural Predictions for Alternative Splice Proteins Expressed in Her2/neu-Induced Breast Cancers," NIH Public Access Author Manuscript, 19 pgs., J. Proteome Res., Dec. 2, 2011, pp. 5503-5511, vol. 10, No. 12.

Milde-Langosch, K. et al., "P16/MTS1 and pRB expression in endometrial carcinomas," Virchows Arch, 1999, pp. 23-28, vol. 434.

Milde-Langosch, K. et al., "p16/MTS1 Inactivation in Ovarian Carcinomas: High Frequency of Reduced Protein Expression Associated With Hyper-Methylation or Mutation in Endometrioid and Mucinous Tumors," Int. J. Cancer (Pred. Oncol.), 1998, pp. 61-65, vol. 79.

Mintz, P. et al., "Fingerprinting the circulating repertoire of antibodies from cancer patients," Nature Biotechnol., Jan. 2003, pp. 57-63, vol. 21, Nature Publishing Group.

Misra, U. et al., "Ligation of cancer cell surface GRP78 with antibodies directed against its COOH-terminal domain up-regulates p53 activity and promotes apoptosis," Mol. Cancer Ther., May 2009, pp. 1350-1362, vol. 7, No. 5, American Association for Cancer Research.

Molema, G. et al., "Tumor Vascular Endothelium: Barrier or Target in Tumor Directed Drug Delivery and Immunotherapy," Pharm. Res., 1997, pp. 2-10, vol. 14, No. 1.

Moretti, L. et al., "Cell Cycle and Vascular Targets for Radiotherapy," Principles and Practice of Lung Cancer: The Official Reference Text of the IASLC, eds. H. Pass et al., Fourth Edition, 2010, Section 2, Chapter 14, pp. 189-208, Lippincott Williams & Wilkins, The People's Republic of China.

Munro, S. et al., "An Hsp70-like Protein in the ER: Identity with the 78 kd Glucose-Regulated Protein and Immunoglobulin Heavy Chain Binding Protein," Cell, Jul. 18, 1986, pp. 291-300, vol. 46, Cell Press.

Munro, S. et al., "A C-Terminal Signal Prevents Secretion of Luminal ER Proteins," Cell, Mar. 13, 1987, pp. 899-907, vol. 48, No. 5, Cell Press.

Myung, N. et al., "Loss of p16 and p27 is associated with progression of Human gastric cancer," Cancer Letters, 2000, pp. 129-136, vol. 153.

Nakao, Y. et al., "Induction of p16 during immortalization by HPV 16 and 18 and not during malignant transformation," British J. Cancer, 1997, pp. 1410-1416, vol. 75, No. 10.

Nanocs, Inc., "PEG Derivatives," http://www.nanocs.com/PEG.htm, 2013; 5 pgs.

Newton, J. et al., "Phage Peptide Display," Handb. Exp. Pharmacol., 2008, pp. 145-163, vol. 185, Part 2.

Newton, J. et al., "In Vivo Bacteriophage Display for the Discovery of Novel Peptide-Based Tumor-Targeting Agents," Methods Mol. Biol.: Biosensors and Biodetection, 2009, pp. 275-290, vol. 504, Humana Press.

Notice of Allowance dated Dec. 14, 2005 from related U.S. Appl. No. 09/914,605; 3 pgs.

Notice of Allowance with Interview Summary dated Jan. 29, 2008 from related U.S. Appl. No. 10/259,087; 8 pgs.

Notice of Allowance dated Apr. 29, 2011 from related U.S. Appl. No. 11/953,780; 5 pgs.

Notice of Allowance dated May 27, 2010 from related U.S. Appl. No. 11/413,783; 4 pgs.

Notice of Allowance dated Sep. 14, 2010 from related U.S. Appl. No. 11/413,783; 4 pgs.

Extended European Search Report from related European Patent Application No. 15824229.7; 9 pgs.

Kapoor, V. et al., "Targeting radiation-inducible cell surface GRP78 using GIRLRG peptide as a novel imaging and therapeutic strategy for tumors," Proceedings of the 106th Annual Meeting of the American Association for Cancer Research, Philadelphia, PA, Apr. 18-22, 2015, pp. 1791, vol. 75, Issue 15 Suppl., Abstract Nr. 1791.

(56) References Cited

OTHER PUBLICATIONS

Notice of Allowance dated Mar. 28, 2018 from related U.S. Appl. No. 15/094,579; 4 pgs.
Wisniewska, M. et al., "Crystal Structures of the ATPase Domains of Four Human Hsp70 Isoforms: HSPA1L/Hsp70-hom, HSPA2/Hsp70-2, HSPA6/Hsp70B', and HSPA5/BiP/GRP78," PLoS ONE, Jan. 2010, pp. 1-8, vol. 5, No. 1, e8625.
Wong, Y. et al., "Frequent loss of heterozygosity of chromosome 3 short arm detected by PCR-based microsatellite polymorphisms in cervical squamous cell carcinoma," Cancer Letters, 1997, pp. 161-164, vol. 115.
Wong, Y. et al., "p16INK4 and p15INK4B Alterations in Primary Gynecologic Malignancy," Gynecologic Onco., 1997, pp. 319-324, vol. 65, Article No. GO974669.
Wong, Y. et al., "Methylation of p16INK4A in primary gynecologic malignancy," Cancer Letters, Mar. 1, 1999, pp. 231-235, vol. 136, No. 2, Abstract Only.
Wu, C-C. et al., "Identification of a New Peptide for Fibrosarcoma Tumor Targeting and Imaging in Vivo," J. Biomed. Biotechnol., 2010, pp. 1-10, vol. 2010, Article 167045.
Xu, X. et al., "Cell cycle proteins PP5 associated with Rad9 and uses in screening for a bioactive agent," Database HCAPLUS on STN, 2001, Abstract WO01/64913, Accession No. 2001:661624, Registry No. 263887-03-02 for human gene rad9 for SEQ ID No. 8, 1 pg.
Xu, X. et al., "The tandem affinity purification method: An efficient system for protein complex purification and protein interaction identification," Protein Expr. Purif., 2010, pp. 149-156, vol. 72, No. 2.
Yamamoto, Y. et al., Molecular Design of Bioconjugated Cell Adhesion Peptide with a Water-Soluble Polymeric Modifier for Enhancement of Antimetastatic Effect, Current Drug Targets, Apr. 1, 2002, pp. 123-130, vol. 3, No. 2, Bentham Science Publishers Ltd.
Yokota, T. et al., "Rapid Tumor Penetration of a Single-Chain Fv and Comparison with Other Immunoglobulin Forms," Can. Res., Jun. 15, 1992, pp. 3402-3408, vol. 52.
Zang, L. et al., "Screening and Identification of a peptide specifically targeted to NCI-H1299 from a phage display peptide library," Cancer Letters, 2009, pp. 64-70, vol. 281, No. 1.
Zhang, J. et al., "Structural Basis of beta-Catenin Recognition by Tax-interacting Protein-1," J. Mol. Biol., 2008, pp. 255-263, vol. 384, No. 1.
Zhang, Y. et al., "Cell Surface Relocalization of the Endoplasmic Reticulum Chaperone and Unfolded Protein Response Regulator GRP78/BiP," J. Biol. Chem., May 14, 2010, pp. 15065-15075, vol. 285, No. 20, The American Society for Biochemistry and Molecular Biology, Inc.
Alewine, C. et al., "TIP-1 Has PDZ Scaffold Antagonist Activity," Mol. Biol. Cell, Oct. 2006, pp. 4200-4211, vol. 17, No. 10.
Ambrosini, V., et al., "Radiopeptide Imaging and Therapy in Europe," J. Nucl. Med., Dec. 2011, pp. 42S-55S, vol. 52, No. 12 (suppl.), Society of Nuclear Medicine.
Andersson, L. et al., "Large-scale synthesis of peptides," Biopolymers (Peptide Science), May 2000, pp. 227-250, vol. 55, No. 3, John Wiley & Sons, Inc.
Arap, W. et al., "Cancer Treatment by Targeted Drug Delivery to Tumor Vasculature in a Mouse Model," Science, Jan. 16, 1998, pp. 377-380, vol. 279.
Arap, M. et al., "Cell surface expression of the stress response chaperone GRP78 enables tumor targeting by circulating ligands," Cancer Cell, Sep. 2004, pp. 275-284, vol. 6, Cell Press.
Baillie, C.T. et al., "Tumor vasculature—a potential therapeutic agent," British J. Can., 1995, pp. 257-267, vol. 72.
Bailon, P. et al., "PEG-modified biopharmaceuticals," Expert Opin. Drug Deliv., 2009, pp. 1-16, vol. 6, No. 1, Informa UK Ltd.
Barry, M. et al., "Toward cell-targeting gene therapy vectors: Selection of cell-binding peptides from random peptide-presenting phage libraries," Nat. Med., Mar. 3, 1996, pp. 299-305, vol. 2, No. 3.
Bender, H. et al., "Enhancement of Monoclonal Antibody Efficacy: The Effect of External Beam Radiation," Hybridoma, 1995, pp. 129-134, vol. 14, No. 2.
Bender, H. et al., "External Beam Radiation Enhances Antibody Mediated Radiocytotoxicity in Human Glioma Cells in Vitro," Anticancer Res., 1997, pp. 1797-1802, vol. 17.
Bhakdi, S., "Removal of SDS From Proteins for Immunochemical Analyses: A Simple Method Utilizing Ultracentrifugation in Sucrose Density Gradients Containing Non-Ionic Detergent," J. Biochem. Biophys. Methods, 1980, pp. 79-90, vol. 2.
Bird, R. et al., "Single-Chain Antigen-Binding Proteins," Science, New Series, Oct. 21, 1988, pp. 423-426, vol. 242, No. 4877.
Boothman, D. et al., "Induction of Tissue-type Plasminogen Activator by Ionizing Radiation in Human Malignant Melanoma Cells," Cancer Res., 1991, pp. 5587-5595, vol. 51.
Brach, M. et al, "Ionizing Radiation Induces Expression of Interleukin 6 by Human Fibroblasts Involving Activation of Nuclear Factor-kB," J. Biolog. Chem., Apr. 25, 1993, pp. 8466-8472, vol. 268, No. 12.
Brooks, B. et al., "CHARMM: The Biomolecular Simulation Program," NIH Public Access Author Manuscript, 124 pgs., J. Comput. Chem., Jul. 30, 2009, pp. 1545-1614, vol. 30, No. 10.
Burg, M. et al., "NG2 Proteoglycan-binding Peptides Target Tumor Neovasculature," Cancer Res., Jun. 15, 1999, pp. 2869-2874, vol. 59.
Burikhanov, R., et al., The Tumor Suppressor Par-4 Activates an Extrinsic Pathway for Apoptosis, Cell, Jul. 24, 2009, pp. 377-388, vol. 138, No. 2, Elsevier Inc.
Cai, X. et al, "Anti-melanoma antibodies from melanoma patients immunized with genetically modified autologous tumor cells: Selection of specific antibodies from single-chain Fv fusion phage libraries," PNAS, Jul. 1995, pp. 6537-6541, vol. 92.
Castellano, M. et al., "CDKN2A/p16 Is Inactivated in Most Melanoma Cell Lines," Cancer Res, 1997, pp. 4868-4875, vol. 57.
Chen, C. et al., "Reactivity of Synthetic Peptide Analogs of Adhesive Proteins in Regard to the Interaction of Human Endothelial Cells With Extracellular Matrix," Blood, May 15, 1991, pp. 2200-2206, vol. 77, No. 10.
Cheng, C-C. et al., "Novel targeted nuclear imaging agent for gastric cancer diagnosis: glucose-regulated protein 78 binding peptide-guided 111In-labeled polymeric micelles," International J. Nanomed., Apr. 2013; pp. 1385-1391, vol. 8, Dove Medical Press Ltd.
Cheresh, D. et al., "Human endothelial cells synthesize and express an Arg-Gly-Asp-directed adhesion receptor involved in attachment to fibrinogen and von Willebrand factor," PNAS, Sep. 1987, pp. 6471-6475, vol. 84.
Chothia, C. et al., "Canonical Structures for the Hypervariable Regions of Immunoglobulins," J. Mol. Biol., 1987, pp. 901-917, vol. 196.
Cohen, M. et al., "Purified autoantibodies against glucose-regulated protein 78 (GRP78) promote apoptosis and decrease invasiveness of ovarian cancer cells," Cancer Lett., Oct. 1, 2011, pp. 104-109, vol. 309, No. 1, Elsevier Inc.
Collins, M. et al., "Mapping multiprotein complexes by affinity purification and mass spectrometry," Curr. Opin. Biotechnol., 2008, pp. 324-330, vol. 19, No. 4.
Corringer, P. et al., "CCK-B Agonist or Antagonist Activities of Structurally Hindered and Peptidase-resistant Boc-CCK4 Derivatives," J. Med. Chem., 1993, pp. 166-172, vol. 36, No. 1.
Croce, C. et al., "Cloning of human RAD54 gene homolog and its diagnostic and therapeutic uses," Database HCAPLUS on STN, 1998, Abstract EP0844305, Accession No. 1998:365000, Registry No. 208601-90-5 for human rad54 for SEQ ID No. 12, 1 pg.
Dai, C. et al., "p16INK4a Expression Begins Early in Human Colon Neoplasia and Correlates Inversely With Markers of Cell Proliferation," Gastroenterology, 2000, pp. 929-942, vol. 119.
Davidson, D., "Kringle 5 of Human Plasminogen Induces Apoptosis of Endothelial and Tumor Cells through Surface-Expressed Glucose-Regulated Protein 78," Cancer Res., Jun. 1, 2005, pp. 4663-4672, vol. 65, No. 11, American Association for Cancer Research.
De Barros, A. et al., "Emerging role of radiolabeled nanoparticles as an effective diagnostic technique," EJNMMI Res., 2012, pp. 1-15, vol. 2, No. 39, Springer.

(56) References Cited

OTHER PUBLICATIONS

De Bree, R. et al., "Selection of monoclonal antibody E48 IgG or U36 IgG for adjuvant radioimmunotherapy in head and neck cancer patients," British J. Cancer, 1997, pp. 1049-1060, vol. 75, No. 7.

Delpino, A. et al., "The 78 kDa Glucose-regulated Protein (GRP78/BIP) is Expressed on the Cell Membrane, is Released into Cell Culture Medium and is Also Present in Human Peripheral Circulation," Bioscience Reports, Jun.-Aug. 2002, pp. 407-420, vol. 22, Nos. 3 and 4, Plenum Publishing Corporation.

Diaz, R. et al., "Determining glioma response to radiation therapy using recombinant peptides," Expert Rev. Anticancer Ther., 2008, pp. 1787-1796, vol. 8, No. 11.

Dimitriadis, G., "Effect of Detergents on Antibody-Antigen Interaction," Anal. Biochem., 1979, pp. 445-451, vol. 98.

Dolganov, G., "The human RAD50 and Septin-2 genes and their roles in myelodysplastic diseases and their diagnostic and therapeutic uses," Database HCAPLUS on STN, 1997, Abstract WO97/27284, Accession No. 1997:513697, Registry No. 194813-18-8 for human clone B15.2, for SEQ ID No. 8, 1 pg.

Edmonds, S., "Antibody-Targeted Chemotherapy with Mylotarg Shows Promise for Many Adults with Deadly Form of Leukemia," American Society of Clinical Oncology 36th Annual Meeting, May 21, 2000, New Orleans, Louisiana.

Ellerby, H. et al., "Anti-cancer activity of targeted pro-apoptotic peptides," Nature Medicine, Sep. 1999, pp. 1032-1038, vol. 5, No. 9.

Evan, G. et al., "Isolation of Monoclonal Antibodies Specific for Human c-myc Proto-Oncogene Product," Mol. Cell Biol., Dec. 1985, pp. 3610-3616, vol. 5, No. 12.

Fani, M. et al., "Radiolabeled Peptides: Valuable Tools for the Detection and Treatment of Cancer," Theranostics, 2012, pp. 481-501, vol. 2, No. 5, Ivyspring International Publisher.

Fields, G. et al., "Solid phase peptide synthesis utilizing 9-fluorenylmethoxycarbonyl amino acids," Int. J. Peptide Protein Res., Mar. 1990, pp. 161-214, vol. 35, No. 3, Blackwell Publishing Ltd.

Figini, M. et al., "Panning Phage Antibody Libraries on Cells: Isolation of Human Fab Fragments against Ovarian Carcinoma Using Guided Selection," Cancer Res., Mar. 1, 1998, pp. 991-996, vol. 58.

Fox, S. et al., "Markers of tumor angiogenesis: clinical applications in prognosis and anti-angiogenic therapy," Investigational New Drugs, 1997, pp. 15-28, vol. 15.

Fu, Y. et al., "Glucose Regulated Proteins in Cancer Progression, Drug Resistance and Immunotherapy," Cancer Biol. Ther., Jul. 2006, pp. 741-744, vol. 5, No. 7, Landes Bioscience.

Garbay-Jaureguiberry, C. et al., "Solid phase synthesis of peptides containing the non-hydrolysable analog of (O)phosphotyrosine, P(CH2PO3H2)Phe," Int. J. Peptide Protein Res., Jun. 1992, pp. 523-527, vol. 39, No. 6, Blackwell Publishing Ltd.

Geradts, J. et al., "Frequent Loss of KAI1 Expression in Squamous and Lymphoid Neoplasms," Am. J. Path., Jun. 1999, pp. 1665-1671, vol. 154, No. 6.

Geradts, J. et al., "Immunohistochemical Detection of the Cyclin-dependent Kinase Inhibitor 2/Multiple Tumor Suppressor Gene 1 (CDKN2/MTS1) Product p16INK4A in Archival Human Solid Tumors: Correlation with Retinoblastoma Protein Expression," Cancer Res., 1995, pp. 6006-6011, vol. 55.

Goldman, C. et al., "Targeted Gene Delivery to Kaposi's Sarcoma Cells via the Fibroblast Growth Factor Receptor," Cancer Res., Apr. 15, 1997, pp. 1447-1451, vol. 57.

Gonzalez-Gronow, M. et al., "Prostate Cancer Cell Proliferation In vitro is Modulated by Antibodies against Glucose-Regulated Protein 78 Isolated from Patient Serum," Cancer Res., Dec. 1, 2006, pp. 11424-11431, vol. 66, No. 23, American Association for Cancer Research.

Gonzalez-Gronow, M. et al., "Plasminogen Structural Domains Exhibit Different Functions When Associated with Cell Surface GRP78 or the Voltage-dependent Anion Channel," J. Biol. Chem., Nov. 9, 2007, pp. 32811-32820, vol. 282, No. 45, The American Society for Biochemistry and Molecular Biology, Inc.

Gump, J. et al., "Phosphorylation of p16INK4A Correlates with Cdk4 Association," J. Biol. Chem., Feb. 28, 2003, pp. 6619-6622, vol. 278, No. 9.

Notice of Allowance with Interview Summary dated Feb. 22, 2011 from related U.S. Appl. No. 12/111,693; 10 pgs.

Notice of Allowance dated Sep. 12, 2011 from related U.S. Appl. No. 11/592,451; 5 pgs.

Notice of Allowance dated Jul. 26, 2000 from related U.S. Appl. No. 09/302,456; 5 pgs.

Notice of Allowance with Examiner-Initiated Interview Summary dated Oct. 28, 2010 from related U.S. Appl. No. 11/183,325; 9 pgs.

Notice of Allowance dated Jul. 24, 2007 from related U.S. Appl. No. 10/689,006; 6 pgs.

Notice of Allowance dated Aug. 17, 2004 from related Australian Patent Application No. 51239/00; 1 pg.

Notice of Allowance with Examiner-Initiated Interview Summary dated Nov. 6, 2012 from related U.S. Appl. No. 13/018,747; 8 pgs.

Notice of Allowance dated Aug. 12, 2013 from related U.S. Appl. No. 13/195,570; 9 pgs.

Notice of Allowance dated Feb. 19, 2014 from related U.S. Appl. No. 13/766,310; 7 pgs.

Notice of Allowance dated Jul. 25, 2014 from related U.S. Appl. No. 14/092,412; 6 pgs.

Notice of Allowance dated Aug. 26, 2014 from related U.S. Appl. No. 14/092,412; 5 pgs.

Notice of Allowance dated Feb. 28, 2018 from related U.S. Appl. No. 15/094,579; 4 pgs.

Nuovo, G. et al., "In situ detection of the hypermethylation-induced inactivation of the p16 gene as an early event in oncogenesis," PNAS, Oct. 26, 1999, pp. 12754-12759, vol. 96, No. 22.

O'Brien, P. et al., "Antibody Phage Display: Methods and Protocols," E-Streams, Dec. 2002, pp. 1-2, vol. 5, No. 12.

Office Action dated Apr. 18, 2005 from related U.S. Appl. No. 09/914,605; 6 pgs.

Office Action dated Sep. 8, 2004 from related U.S. Appl. No. 09/914,605; 6 pgs.

Office Action dated Feb. 17, 2006 from related U.S. Appl. No. 10/259,087; 19 pgs.

Office Action dated Feb. 22, 2005 from related U.S. Appl. No. 10/259,087; 15 pgs.

Office Action dated May 4, 2004 from related U.S. Appl. No. 10/259,087; 11 pgs.

Office Action dated Apr. 4, 2007 corresponding to U.S. Appl. No. 10/650,057; 19 pgs.

Office Action dated Jan. 25, 2007 corresponding to U.S. Appl. No. 10/650,057; 19 pgs.

Office Action dated Aug. 16, 2006 corresponding to U.S. Appl. No. 10/650,057; 19 pgs.

Office Action with Interview Summary dated May 18, 2007 from related U.S. Appl. No. 10/259,087; 18 pgs.

Office Action dated Jan. 24, 2008 from related U.S. Appl. No. 11/219,634; 7 pgs.

Office Action dated Dec. 3, 2008 from related U.S. Appl. No. 11/219,634; 8 pgs.

Office Action dated Sep. 3, 2009 from related U.S. Appl. No. 11/219,634; 8 pgs.

Office Action dated Oct. 22, 2010 from related U.S. Appl. No. 11/953,780; 6 pgs.

Office Action dated Feb. 19, 2010 from related U.S. Appl. No. 11/953,780; 6 pgs.

Office Action dated Jan. 7, 2010 from related U.S. Appl. No. 11/413,783; 9 pgs.

Office Action dated Jan. 28, 2008 from related U.S. Appl. No. 11/413,783; 11 pgs.

Office Action dated Aug. 5, 2010 from related U.S. Appl. No. 12/111,693; 27 pgs.

Office Action dated Feb. 28, 2011 from related U.S. Appl. No. 11/592,451; 3 pgs.

Office Action dated Mar. 24, 2011 from related U.S. Appl. No. 11/592,451; 18 pgs.

(56) References Cited

OTHER PUBLICATIONS

Office Action dated May 13, 2010 from related U.S. Appl. No. 11/592,451; 11 pgs.
Office Action dated Nov. 18, 2010 from related U.S. Appl. No. 11/592,451; 17 pgs.
Office Action dated Jun. 8, 2010 from related U.S. Appl. No. 11/183,325; 11 pgs.
Office Action dated Jan. 19, 2007 from related U.S. Appl. No. 10/689,006; 6 pgs.
Office Action dated Nov. 8, 2007 from related Canadian Patent Application No. 2,368,748; 5 pgs.
Office Action dated May 17, 2005 from related Canadian Patent Application No. 2,368,748; 5 pgs.
Office Action dated Feb. 28, 2005 from related European Patent Application No. 00935839.1; 3 pgs.
Office Action dated Aug. 13, 2008 from related European Patent Application No. 00935839.1; 4 pgs.
Office Action dated Jul. 18, 2012 from related U.S. Appl. No. 13/018,747; 6 pgs.
Office Action dated Nov. 15, 2012 from related U.S. Appl. No. 13/195,570; 5 pgs.
Office Action dated Aug. 1, 2012 from related U.S. Appl. No. 13/195,570; 8 pgs.
Office Action dated May 1, 2013; from related U.S. Appl. No. 13/195,570; 6 pgs.
Office Action dated Jun. 25, 2014 from related U.S. Appl. No. 13/326,870; 13 pgs.
Office Action dated Nov. 12, 2013 from related U.S. Appl. No. 13/766,310; 8 pgs.
Office Action dated Jan. 14, 2014 from related U.S. Appl. No. 14/092,412; 6 pgs.
Office Action dated Oct. 6, 2017 from related U.S. Appl. No. 15/094,579; 8 pgs.
Oliver, A. et al., "The HPV16 E6 binding protein Tip-1 interacts with ARHGEF16, which activates Cdc42," Br. J. Cancer, 2011, pp. 324-331, vol. 104, No. 2.
Hallahan, D. et al., "Ionizing Radiation Mediates Expression of Cell Adhesion Molecules in Distinct Histological Patterns within the Lung," Cancer Res., Jun. 1, 1997, pp. 2096-2099, vol. 57.
Hallahan, D. et al., "Cell Adhesion Molecules Mediate Radiation-induced Leukocyte Adhesion to the Vascular Endothelium," Cancer Res., Nov. 15, 1996, pp. 5150-5155, vol. 56.
Hallahan, D. et al., "c-jun and Egr-1 Participate in DNA Synthesis and Cell Survival in Response to Ionizing Radiation Exposure," J. Bio. Chem., Dec. 22, 1995, pp. 30303-30309, vol. 270, No. 51.
Hallahan, D. et al., "E-selectin gene induction by ionizing radiation is independent of cytokine induction," Biochem. Biophys. Res. Commun., Dec. 26, 1995, pp. 784-795, vol. 217, No. 3.
Hallahan, D. et al., "Integrin-mediated targeting of drug delivery to irradiated tumor blood vessels," Cancer Cell, Jan. 2003, pp. 63-74, vol. 3, No. 1.
Hallahan, D. et al., "Intercellular adhesion molecule 1 knockout abrogates radiation induced pulmonary inflammation," PNAS, Jun. 1997, pp. 6432-6437, vol. 94.
Hallahan, D. et al., "Nuclear Factor kB Dominant Negative Genetic Constructs Inhibit X-ray Induction of Cell Adhesion Molecules in the Vascular Endothelium," Cancer Res., Dec. 1, 1998, pp. 5484-5488, vol. 58.
Hallahan, D. et al., "Radiation Signaling Mediated by Jun Activation following Dissociation from a Cell Type-specific Repressor," J. Bio. Chem., Mar. 5, 1993, pp. 4903-4907, vol. 268, No. 7.
Hallahan, D. et al., "Spatial and temporal control of gene therapy using ionizing radiation," Nature Medicine, Aug. 1995, pp. 786-791, vol. 1, No. 8.
Hallahan, D. et al., Targeting drug delivery to radiation-induced neoantigens in tumor microvasculature, J. Controlled Release, 2001, pp. 183-191, vol. 74.
Hallahan, D. et al., "X-Ray-induced P-selectin Localization to the Lumen of Tumor Blood Vessels," Cancer Res., Nov. 15, 1998, pp. 5216-5220, vol. 58.
Hallahan, D., "Radiation-Mediated Gene Expression in the Pathogenesis of the Clinical Radiation Response," Seminars Radiat. Oncol., Oct. 1996, pp. 250-267, vol. 6, No. 4.
Hallahan, D., et al., "Radiation-Mediated Control of Drug Delivery," Am. J. Clin. Oncol., 2001, pp. 473-480, vol. 24, No. 5.
Han, Z. et al., "Noninvasive assessment of cancer response to therapy," Nat. Med., Mar. 2008, pp. 343-349, vol. 14, No. 3.
Han, M. et al., "The PDZ protein TIP-1 facilitates cell migration and pulmonary metastasis of human invasive breast cancer cells in athymic mice," NIH Public Access Author Manuscript, 13 pgs., Biochem. Biophys. Res. Commun., May 25, 2012, pp. 139-145, vol. 422, No. 1.
Harari, O. et al., "Targeting an adenoviral gene vector to cytokine-activated vascular endothelium via E-selectin," Gene Therapy, 1999, pp. 801-807, vol. 6, Stockton Press.
Hareyama, M. et al., "The Effect of Radiation on the Expression of Intercellular Adhesion Molecule-1 of Human Adenocarcinoma Cells," Int. J. Rad. Oncol. Biol. Phys., 1998, pp. 691-696, vol. 40, No. 3.
Hariri, G et al., "Radiation-Guided P-Selectin Antibody Targeted to Lung Cancer," NIH Public Access Author Manuscript, available in PMC May 1, 2009, pp. 1-22, Published in final edited form as: Ann. Biomed. Eng., May 2008, pp. 821-830, vol. 36, No. 5.
Hariri, G. et al., "Radiation-Guided Drug Delivery to Mouse Models of Lung Cancer," Clin. Cancer Res., Oct. 15, 2010, pp. 4968-4977, vol. 16, No. 20.
He, X-S. et al., "Expression, deleton and mutation of p16 gene in human gastric cancer," World J. Gastroenterol., 2001, pp. 515-521, vol. 7, No. 4.
Hirama, T. et al., "p16 (CDKN2—Cyclin-dependent Kinase-4 Inhibitor-Multiple Tumor Suppressor-1) Gene Is Not filtered in Uterine Cervical Carcinomas or Cell Lines," Modern Pathology, 1996, pp. 26-30, vol. 9, No. 1, Abstract only.
Hirata, "Fate of Intravenously Injected Human Tumor Cells in the Lung of Nude Mice Following Whole-Body X-Irradiation," Invasion Metastasis, 1985, pp. 61-70, Abstract Only.
Hirata, H. et al., "Artificial Metastases and Decrease of Fibrinolysis in the Nude Mouse Lung After Hemithoracic Irradiation," Clin. Expl. Metastasis, 1984, pp. 311-319, vol. 2, No. 4, Abstract Only.
Humira™ (adalimumab) Package Insert, Dec. 20, 2002, 16 pgs.
Huston, J., "Protein engineering of antibody binding sites: Recovery of specific activity in an anti-digoxin single-chain Fv analogue produced in *Escherichia coli*," PNAS, Aug. 1998, pp. 5879-5883, vol. 85.
Ikeda, K. et al., "Extraction and Analysis of Diagnostically Useful Proteins from Formalin-fixed, Paraffin-embedded Tissue Sections," J. Histochem. Cytochem., 1998, pp. 397-403, vol. 46, No. 3.
International Preliminary Report on Patentability dated Oct. 30, 2007 from related International Patent Application No. PCT/US2005/031367; 4 pgs.
International Search Report dated Oct. 11, 2007 from related International Patent Application No. PCT/US2005/031367; 1 pg.
International Preliminary Examination Report dated Aug. 27, 2001 from related International Patent Application No. PCT/US2000/011485; 6 pgs.
International Search Report dated Oct. 4, 2000 from related International Patent Application No. PCT/US2000/011485; 4 pgs.
International Preliminary Examination Report dated Jul. 20, 2005 from related International Patent Application No. PCT/US04/034719; 3 pgs.
International Search Report dated Jan. 26, 2005 from related International Patent Application No. PCT/US04/034719; 1 pg.
International Search Report dated Feb. 10, 2005 from related International Patent Application No. PCT/US02/030917; 4 pgs.
International Preliminary Report on Patentability dated Jan. 16, 2008 from International Patent Application No. PCT/US2006/027283; 4 pgs.
International Search Report and Written Opinion dated Mar. 13, 2007 from related International Patent Application No. PCT/US2006/027283; 7 pgs.
International Preliminary Report on Patentability dated Apr. 10, 2014 from related International Patent Application No. PCT/US2012/058329; 5 pgs.

(56) References Cited

OTHER PUBLICATIONS

International Search Report and Written Opinion dated Jan. 8, 2013 from related International Patent Application No. PCT/US2012/058329; 5 pgs.
International Search Report and Written Opinion dated Dec. 31, 2015 related International Patent Application No. PCT/US2015/041986; 13 pgs.
International Search Report and Written Opinion dated Jan. 4, 2013 from related International Patent Application No. PCT/US2012/048856; 14 pgs.
Interview Summary dated May 6, 2010 from related U.S. Appl. No. 11/413,783; 3 pgs.
Interview Summary dated Dec. 22, 2010 from related U.S. Appl. No. 12/111,693; 2 pgs.
Ito, T. et al., "Preclinical Assessments of 90Y-labeled C110 Anti-Carcinoembryonic Antigen Immunotoxin: A Therapeutic Immunoconjugate for Human Colon Cancer," Cancer Res., Jan. 1, 1991, pp. 255-260, vol. 51.
Jaboin, J. et al., "Using In Vivo Biopanning for the Development of Radiation-Guided Drug Delivery Systems," Methods Mol. Biol., Gene Ther. Cancer, 2009, pp. 285-300, vol. 542, Humana Pres0073.
Jahroudi, N. et al., "Ionizing irradiation increases transcription of the von Willebrand factor gene in endothelial cells," Blood, Nov. 15, 19966, pp. 3801-3814, vol. 88, No. 10, (1996).
Jain, R., "Barriers to Drug Delivery in Solid Tumors," Scientific American, Jul. 1994, pp. 58-65, vol. 271.
Johnson, D., et al., eds., "Superior Vena Cava Syndrome," Cancer of the lung. Abeloff's Clinical Oncology, 2008, pp. 803-814, Chapter 54.
Johnson, T. et al., "Therapy of B-cell lymphomas with monoclonal antibodies and radioimmunoconjugates: the Seattle experience," Ann. Hematol., 2000 pp. 175-182, vol. 79.
Kaltsas, G. et al., "Treatment of advanced neuroendocrine tumours with radiolabelled somatostatin analogues," Endocrine-Related Cancer, 2005, pp. 683-699, vol. 12, Society for Endocrinology, Great Britain.
Kanamori, M. et al., "The PDZ Protein Tax-interacting Protein-1 Inhibits beta-Catenin Transcriptional Activity and Growth of Colorectal Cancer Cells," J. Biol. Chem., Oct. 3, 2003, pp. 38758-38764, vol. 278, No. 40.
Kapoor, V. et al., "Circulating cycloxygenase-2 in patients with tobacco-related intraoral squamous cell carcinoma and evaluation of its peptide inhibitors as potential antitumor agent," J. Cancer Res. Clin. Onco., Dec. 2010, pp. 1795-1804, vol. 136, No. 12, Springer-Verlag.
O'Nions, J. et al., "p73 is over-expressed in vulval cancer principally as the Δ2 isoform," British J. Cancer, 2001, pp. 1551-1556, vol. 85, No. 10.
Palama, I. et al., "Imatinib-loaded polyelectrolyte microcapsules for sustained targeting of BCR-ABL+ leukemia stem cells," Nanomedicine, 2010, pp. 1-13, vol. 5, No. 3, Future Medicine Ltd.
Pan, X-M. et al., "What Is the Minimum Number Of Residues to Determine the Secondary Structural State?," J. Protein Chem., 1999, pp. 579-584, vol. 18, No. 5.
Pasqualini, R. et al., "Organ targeting in vivo using phage display peptide libraries," Nature, Mar. 28, 1996, pp. 364-366, vol. 380.
Passarella, R. et al., "Targeted Nanoparticles That Deliver a Sustained, Specific Release of Paclitaxel to Irradiated Tumors," Cancer Res., Jun. 1, 2010, pp. 4550-4559, vol. 70, No. 11.
Passarella, R. et al., "Recombinant Peptides as Biomarkers for Tumor Response to Molecular Targeted Therapy," NIH Public Access Author Manuscript, 25 pgs., Clin. Cancer Res., Oct. 15, 2009, pp. 6421-6429, vol. 15, No. 20.
Pastan, I., "Targeted therapy of cancer with recombinant immunotoxins," Biochimica et Biophysica Acta, 1997, pp. C1-C6, vol. 1333.
Pavone, V. et al. "Non coded Calpha,alpha-disubstituted amino acids: X-ray diffraction analysis of a dipeptide containing (S)-alpha-methylserine," Int. J. Pept. Protein Res., 1993, pp. 15-20, vol. 41, No. 1.
Philippova, M. et al., "Identification of Proteins Associating with Glycosylphosphatidylinositol-Anchored T-Cadherin on the Surface of Vascular Endothelial Cells: Role for Grp78/BiP in T-Cadherin-Dependent Cell Survival," Mol. Cell Biol., Jun. 2008, pp. 4004-4017, vol. 28, No. 12, American Society for Microbiology.
Phillips, J. et al., "Scalable Molecular Dynamics with NAMD," NIH Public Access Author Manuscript, 43 pgs., J. Comput. Chem., Dec. 2005, pp. 1781-1802, vol. 26, No. 16.
Pinsky, D. et al., "Hypoxia-induced Exocytosis of Endothelial Cell Weibel-Palade Bodies. A Mechanism for Rapid Neutrophil Recruitment after Cardiac Preservation," J. Clin. Invest., Jan. 1996, pp. 493-500, vol. 97, No. 2.
Plath, T. et al., "A Novel Function for the Tumor Suppressor p16INK4a: Induction of Anoikis via Upregulation of the alpha5beta1 Fibronectin Receptor," J. Cell Bio., Sep. 18, 2000, pp. 1467-1477, vol. 150, No. 6.
Pyrko, P. et al., "The Unfolded Protein Response Regulator GRP78/BiP as a Novel Target for Increasing Chemosensitivity in Malignant Gliomas," Cancer Res.Oct. 15, 2007, pp. 9809-9816, vol. 67, No. 20, American Association for Cancer.
Qualtiere, L. et al., "Effects of Ionic and Nonionic Detergents on Antigen-Antibody Reactions," J. Immunol., Nov. 1977, pp. 1645-1651, vol. 119.
Raiter, A. et al., "Activation of GRP78 on Endothelial Cell Membranes by an ADAM15-Derived Peptide Induces Angiogenesis," J. Vasc. Res., 2010, pp. 399-411, vol. 47, S. Karger AG, Basel.
Rajotte, D. et al., "Membrane Dipeptidase Is he Receptor for a Lung-targeting Peptide Identified by in vivo Phage Display," J. Bio. Chem., Apr. 23, 1999, pp. 11593-11598, vol. 274, No. 17.
Rangel, R. et al., "Combinatorial targeting and discovery of ligand-receptors in organelles of mammalian cells," Nat. Commun., 2012, pp. 1-10, vol. 3, No. 788.
Rosenberg, E. et al., "Destruction of Human Lymphoid Tissue-Culture Cell Lines by Human Peripheral Lymphocytes in 51Cr-Release Cellular Cytotoxicity Assays," J. Nat. Cancer Inst., Feb. 1974, pp. 345-352, vol. 52, No. 2.
Rufini, V. et al., "Imaging of Neuroendocrine Tumors," Seminars in Nuclear Medicine, 2006, pp. 228-247, vol. 36, Elsevier Inc.
Ruoslahti, E., "RGD and Other Recognition Sequences for Integrins," Annu. Rev. Cell Dev. Biol., 1996, pp. 697-715, vol. 12.
Ryder, K. et al., "An Enzyme Immunoassay Procedure for Cancer Antigen 125 Evaluated," Clin. Chem., 1988, pp. 2513-2516, vol. 34, No. 12.
Sakamoto, N. et al., "Inhibition of Angiogenesis and Tumor Growth by a Synthetic Laminin Peptide, CDPGYIGSR-NH2," Cancer Res., Feb. 1, 1991, pp. 903-906, vol. 51.
Sano, T., et al., "Expression Status of p16 Protein Is Associated with Human Papillomavirus Oncogenic Potential in Cervical and Genital Lesions," Am. J. Pathol., 1998, pp. 1741-1748, vol. 153, No. 6.
Sano, T. et al., "Immunohistochemical overexpression of p16 protein associated with intact retinoblastoma protein expression in cervical cancer and cervical intraepithelial neoplasia," Pathology Int., 1998, pp. 580-585, vol. 48.
Sano, T. et al., "Overexpression of p16 and p14ARF is associated with human papillomavirus infection in cervical squamous cell carcinoma and dysplasia," Pathology Int., 2002, pp. 375-383, vol. 52.
Schottelius, M. et al., "Molecular imaging targeting peptide receptors," Methods, Jun. 2009, pp. 161-177, vol. 48, No. 2, Elsevier.
Sengupta, S. et al., "Temporal targeting of tumour cells and neovasculature with a nanoscale delivery system," Nat. Lett., Jul. 28, 2005, pp. 568-572, vol. 436.
Serrano, M. et al., "A new regulatory motif in cell-cycle control causing specific inhibition of cyclin D/CDK4," Nature, Dec. 16, 1993, pp. 704-707, vol. 366.
Shalaby, M. et al., "Development of Humanized Bispecific Antibodies Reactive with Cytotoxic Lymphocytes and Tumor Cells Overexpressing the HER2 Protooncogene," J. Exp. Med., Jan. 1992, pp. 217-225, vol. 175, The Rockefeller University Press.
Sherr, C., "The INK4a/ARF Network in Tumor Suppression," Nat. Rev. Mol. Cell Bio., Oct. 2001, pp. 731-737, vol. 2.

(56) References Cited

OTHER PUBLICATIONS

Shigemasa, K. et al., "p16 overexpression: a potential early indicator of transformation in ovarian carcinoma," J. Soc. Gynecol. Invest., 1997, pp. 95-102, vol. 4, No. 2.

Shim, C. et al., "Profiling of differentially expressed genes in human primary cervical cancer by complementary DNA expression array," Clin. Cancer Res., Dec. 1998, pp. 3045-3050, vol. 4.

Sivam, G. et al., "Therapeutic Efficacy of a Doxorubicin Immunoconjugate in a Preclinical Model of Spontaneous Metastatic Human Melanoma," Cancer Res., Jun. 1, 1995, pp. 2352-2356, vol. 55.

Song, C. et al., "Combined Cytolytic Effect of X Irradiation and Cell-Mediated Immune Reactions on Tumor Cells in Vitro," Radiology, Apr. 1974, pp. 213-214, vol. 111.

Stratton, J. et al., "Imaging Arterial Thrombosis: Comparison of Technetium-99m-Labeled Monoclonal Antifibrin Antibodies and Indium-111-Platelets," J. Nucl. Med., Nov. 1994, pp. 1731-1737, vol. 35, No. 11.

Sudarsanam, S., "Structural Diversity of Sequentially Identical Subsequences of Proteins: Identical Octapeptides Can Have Different Conformations," PROTEINS: Structure, Function, and Genetics, 1998, pp. 228-231, vol. 30, Wiley-Liss, Inc.

Sun, Q. et al., "Expressions of GRP78 and Bax associate with differentiation, metastasis, in non-small cell lung cancer," Mol. Biol. Rep., 2012, pp. 6753-6761, vol. 39, Springer.

Suneja, S. et al., "Quantification of a neurotrophin receptor from submilligram quantities of brain tissue using Western blotting," Brain Res. Protocols, 1998, pp. 88-93, vol. 3.

Supplementary European Search Report from European Patent Application No. 00935839.0 dated Mar. 31, 2003; 5 pgs.

Takeuchi, H. et al., "Altered p16/MTS1/CDKN2 and cyclin D1/PRAD-1 gene expression is associated with the prognosis of squamous cell carcinoma of the esophagus," Clin. Cancer Res., Dec. 1997, pp. 2229-2236, vol. 3.

Tam, S. et al., "Differential Expression and Cell Cycle Regulation of the Cyclin-dependent Kinase 4 Inhibitor p16Ink4," Cancer Res., Nov. 15, 1994, pp. 5816-5820, vol. 54.

Triantafilou, M. et al., "Major Histocompatibility Class One Molecule Associates With Glucose Regulated Protein (GRP) 78 on the Cell Surface," Human Immunol., Aug. 2001, pp. 764-770, vol. 62, No. 8, Elsevier Science Inc.

Tsujie, M. et al., "Expression of Tumor Suppressor Gene p16INK4 Products in Primary Gastric Cancer," Oncology, 2000, pp. 126-136, vol. 58.

Tung, C.-H. et al., "An Acridine Amino Acid Derivative for Use in Fmoc Peptide Synthesis," Pept. Res., Mar.-Apr. 1992, pp. 115-118, vol. 5, No. 2, Eaton Publishing.

Urge, L. et al., "Fmoc-protected, glycosylated asparagines potentially useful as reagents in the solid-phase synthesis pf N-glycopeptides," Carbohydr. Res., Nov. 4, 1992, pp. 83-93, vol. 235, No. 4, Elsevier Science Publishers B.V., Amsterdam.

Vithayathil, R. et al., "The Scope of Phage Display for Membrane Proteins," NIH Public Access Author Manuscript, 18 pgs., J. Mol. Biol., Dec. 9, 2011, pp. 499-510, vol. 414, No. 4.

Wang, J. et al., "How Well Does a Restrained Electrostatic Potential (RESP) Model Perform in Calculating Conformational Energies of Organic and Biological Molecules?," J. Comput. Chem., 2000, pp. 1049-1074, vol. 21, No. 12, John Wiley & Sons, Inc.

Wang, H. et al., "TIP-1 Translocation onto the Cell Plasma Membrane Is a Molecular Biomarker of Tumor Response to Ionizing Radiation," PLoS ONE, Aug. 2010, pp. 1-12, vol. 5, No. 8, e12051.

Weichselbaum, R. et al., "Gene Therapy Targeted by Radiation Preferentially Radiosensitizes Tumor Cells," Cancer Res., Aug. 15, 1994, pp. 4266-4269, vol. 54.

Wentzensen, N. et al., "Identification of High-Grade Cervical Dysplasia by the Detection of p16INK4a in Cell Lysates Obtained From Cervical Samples," Cancer, Nov. 1, 2006, pp. 2307-2313, vol. 107, No. 9.

Communication Under Rule 71(3) (Notice of Allowance) dated Feb. 15, 2019 from related European Patent Application No. 15824229.7; 7 pgs.

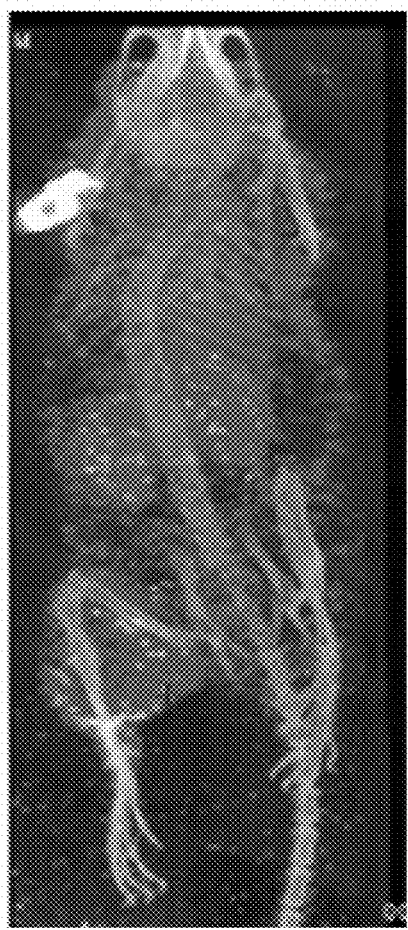
FIG. 1A      FIG. 1B

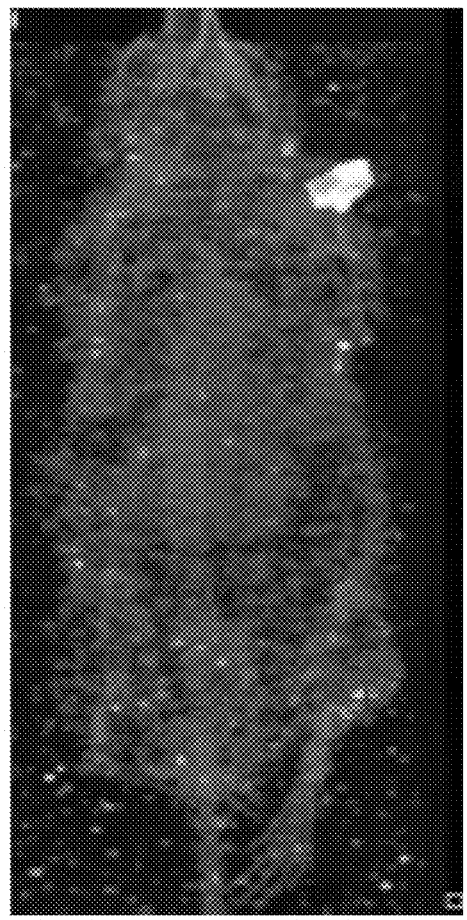 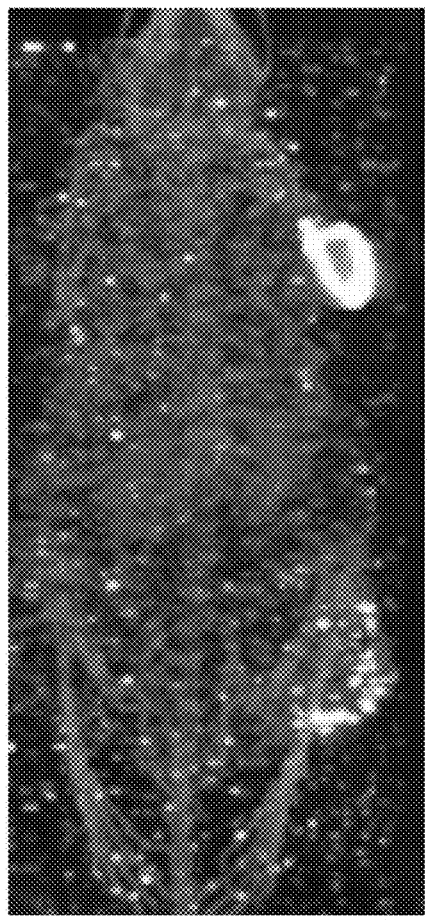
FIG. 3A  FIG. 3B

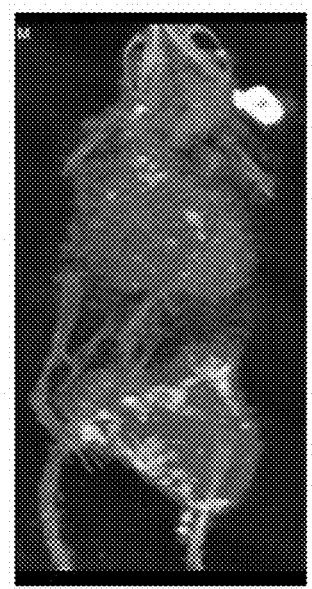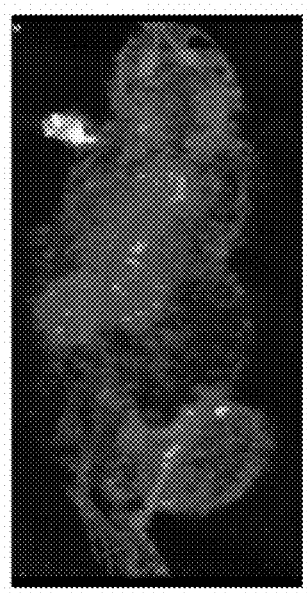
FIG. 10A  FIG. 10B  FIG. 10C

COMPOSITIONS TARGETING RADIATION-INDUCED MOLECULES AND METHODS OF USE THEREOF

CROSS REFERENCE TO RELATED APPLICATIONS

This application claims the benefit of PCT Application PCT/US2015/041986, filed Jul. 24, 2015, which claims the benefit of US provisional application number 62/028,771, filed Jul. 24, 2014, each of the disclosures of which is hereby incorporated by reference in its entirety.

GOVERNMENTAL RIGHTS

This invention was made with government support under 1R01CA140220-02, 5R01CA125757-06, and 7R01CA112385-0 awarded by the National Institutes of Health. The government has certain rights in the invention.

FIELD OF THE INVENTION

The invention encompasses peptide constructs useful in the recognition of tumor cells and tumor specific delivery of drugs and therapies.

BACKGROUND OF THE INVENTION

In the United States, the probability that an individual, over the course of a lifetime, will develop or die from cancer is 1 in 2 for men and 1 in 3 for women. Many anti-tumor drugs, are toxic to non-tumor cells, resulting in hard to tolerate side-effects. Tumor-specific drug delivery and therapy methods have the potential to reduce or prevent tumor growth in organisms allowing them to lead longer, healthier lives. Tumor-targeted drug delivery has the potential to minimize toxicity to normal tissues and improve the bioavailability of therapeutic agents to tumor cells. Presently, drug delivery systems are developed against constitutively expressed cancer antigens such as EGFR receptor and HER2. There are a limited percentage of patients that have overexpression of these antigens on cancer. Therefore, there is a need in the art to develop anti-tumor agents that expand the number of cancer receptors that can be targeted.

SUMMARY OF THE INVENTION

In an aspect, the invention encompasses a composition comprising a peptide construct, wherein the peptide construct comprises:

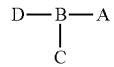

wherein
  A is a peptide that specifically binds to an epitope exposed on an irradiated tumor cell;
  B is a linker comprising at least three amino acids, wherein at least one of the amino acids is selected from the group consisting of lysine, tyrosine, histidine and cysteine;
  C is at least one chelator conjugated to B; and
  D is polyethylene glycol (PEG).

In another aspect, the invention encompasses a method of detecting a tumor in a subject. The method comprises exposing a target area of the subject where the presence of a tumor is suspected to ionizing radiation, administering to the subject a composition comprising a peptide construct, wherein the peptide construct comprises:

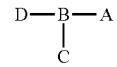

wherein
  A is a peptide that specifically binds to an epitope exposed on an irradiated tumor cell;
  B is a linker comprising at least three amino acids, wherein at least one of the amino acids is selected from the group consisting of lysine, tyrosine, histidine and cysteine;
  C is at least one chelator conjugated to B and complexed with a radionuclide; and
  D is polyethylene glycol (PEG); and
detecting the radionuclide to detect binding of the peptide to a cell in the subject, wherein the presence of the radionuclide indicates the presence of a tumor in the target area of the subject.

In still another aspect, the invention encompasses a method for enhancing radiotherapy in a subject. The method comprises administering to the subject a composition comprising a peptide construct, wherein the peptide construct comprises:

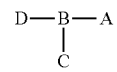

wherein
  A is a peptide that specifically binds to an epitope exposed on an irradiated tumor cell;
  B is a linker comprising at least three amino acids, wherein at least one of the amino acids is selected from the group consisting of lysine, tyrosine, histidine and cysteine;
  C is at least one chelator conjugated to B and complexed with a radionuclide; and
  D is polyethylene glycol (PEG).

BRIEF DESCRIPTION OF THE FIGURES

The application file contains at least one drawing executed in color. Copies of this patent application publication with color drawing(s) will be provided by the Office upon request and payment of the necessary fee.

FIG. 1A-B depicts SPECT images of the spatial and temporal pharmacokinetics of (FIG. 1A) $^{111}$In-labeled control peptide and (FIG. 1B) $^{111}$In-labeled PEG-GIRLRG (SEQ ID NO:1) within irradiated A549 tumors at 72 hours following administration. The right hind limb tumor was treated with 3 Gy and left hind limb tumor is an untreated (0Gy) internal control in the same mouse.

FIG. 3A-B depicts SPECT images of the spatial and temporal pharmacokinetics of (FIG. 3A) $^{111}$In-labeled control peptide and (FIG. 3B) $^{111}$In-labeled PEG-GIRLRG (SEQ ID NO:1) within irradiated OE33 tumors at 72 hours following administration. Right hind limb tumor was treated with 3 Gy and left hind limb tumor is an untreated (0Gy) internal control in the same mouse.

(FIG. 4A) shows NIR image of control scrambled peptide. (FIG. 4B) shows NIR image of GIRLRG (SEQ ID NO:1). (FIG. 4C, FIG. 4D) shows NIR image of blocking studies ALX750 conjugated to GIRLRG (SEQ ID NO:1) peptide. (FIG. 4C) shows NIR when control IgG is administered before GIRLRG (SEQ ID NO:1). (FIG. 4D) shows NIR when control anti-GRP78 antibody is administered before GIRLRG (SEQ ID NO:1).

(FIG. 5A) Shows the contact points of GIRLRG (SEQ ID NO:1) peptide to GRP78 protein. (FIG. 5B and FIG. 5C) Show the residues of GIRLRG (SEQ ID NO:1) interacting with the ribbon model of GRP78 ATPase domain.

(FIG. 6A) Sensogram for immobilization of GRP78 protein on the surface of the sensor chip via amine coupling method. (FIG. 6B) Overlay sensograms of the indicated concentrations of the GIRLRG (SEQ ID NO:1) peptide that passed over the chip.

(FIG. 7A) D54 glioma; (FIG. 7B) HT3 cervical cancer; (FIG. 7C) OE33 esophageal cancer; (FIG. 7D) A549 lung cancer.

FIG. 10A-C depicts SPECT imaging with radiolabeled PEG-GIRLRG (SEQ ID NO:1) peptide in nude mice with (FIG. 10A) heterotopic lung (A549), (FIG. 10B) pancreatic (BXPC3) and (FIG. 10C) brain (D54) cancer. The tumor on the right hind limb was irradiated with 3 doses of 3 Gy. Enhanced tumor binding of the PEG-GIRLRG (SEQ ID NO:1) peptide is observed in A549, BXPC3 and D54 tumors.

DETAILED DESCRIPTION OF THE INVENTION

Figure 2:
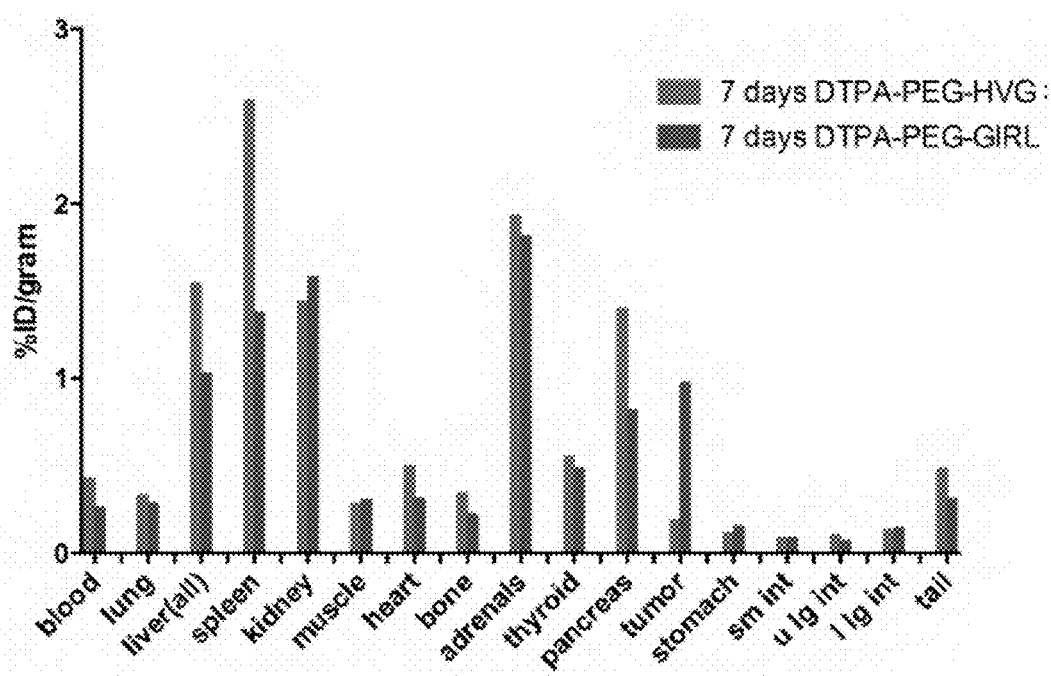
FIG. 2 depicts a bar graph of measurements of gamma emission from mice shown in FIG. 1: $^{111}$In-labeled control peptide (DTPA-PEG) and $^{111}$In-labeled DTPA-PEG-GIRLRG (SEQ ID NO:1) within irradiated mouse A549 tumors at 7 days following administration.
Figure 4A:
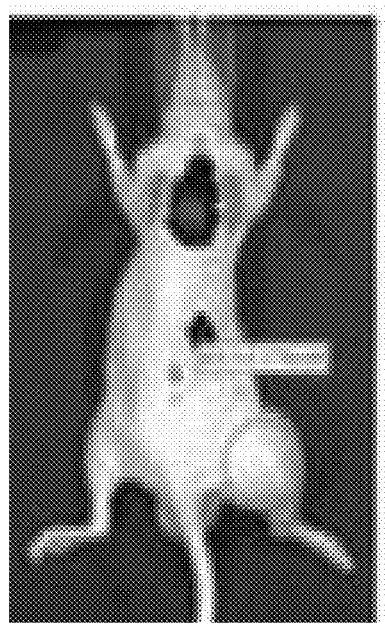
FIG. 4A-D depicts near infrared images of ALX750 conjugated to GIRLRG (SEQ ID NO:1) peptide. Right hind limb tumors were treated with 3 Gy.
Figure 4B:
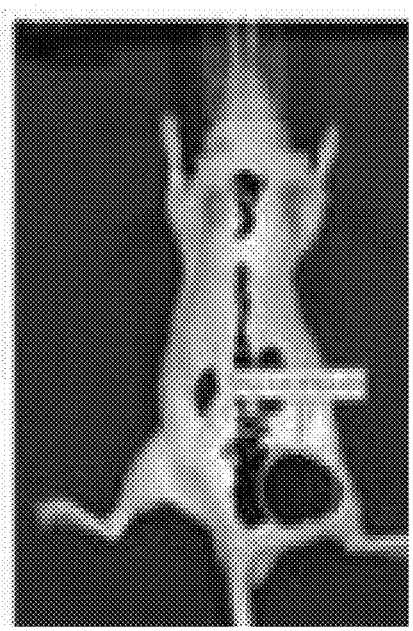
Figure 4C:
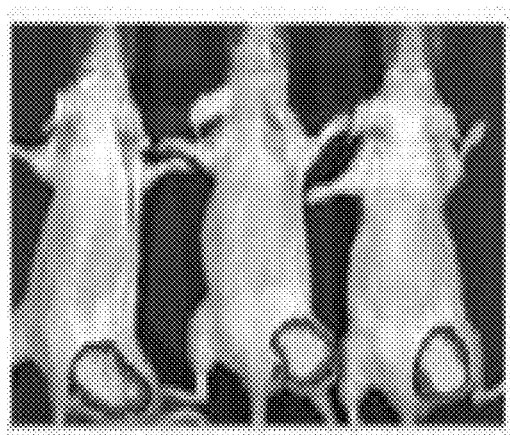
Figure 4D:
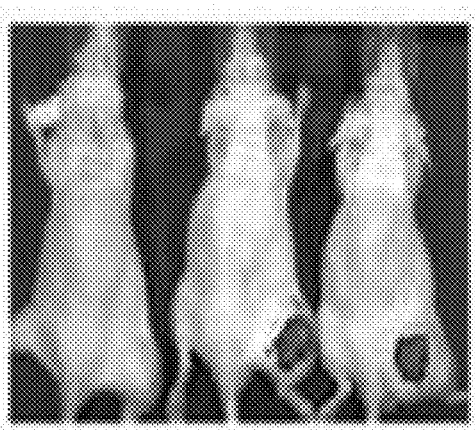

The present disclosure is directed to peptide binding drug delivery systems that target inducible proteins in cancer. This expands the number of cancer receptors that can be targeted for development of drug delivery systems. The general principle of the disclosed invention is that cancer cells respond to ionizing radiation through a stress response that involves membrane transport and presentation of stress proteins on the cell surface. These proteins are normally sequestered within the cancer cell but are transported to the surface in response to oxidative stress and DNA strand breaks caused by ionizing radiation. The present invention exploits this physiologic response by developing peptide ligands that bind to radiation-inducible stress proteins with high affinity and specificity. Conjugation of peptides to therapeutic agents can specifically deliver cytotoxic agents to tumors. As such, the present disclosure may improve tumor control, pharmacokinetics and bioavailability of cancer drugs. GIRLRG (SEQ ID NO:1) is a peptide that binds specifically to radiation-inducible GRP78 protein on cancer. This peptide may be used for the development of radiopharmaceuticals, liposomes and nanoparticles to target poor prognosis cancers.

I. Composition

The present disclosure is directed to a composition comprising a peptide construct, wherein the peptide construct comprises:

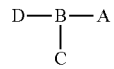

wherein
   A is a peptide that specifically binds to an epitope exposed on an irradiated tumor cell;
   B is a linker comprising at least three amino acids, wherein at least one of the amino acids is selected from the group consisting of lysine, tyrosine, histidine and cysteine;
   C is at least one chelator conjugated to B; and
   D is polyethylene glycol (PEG).

Each element will be described in greater detail below.

(a) Peptide (A)

The present disclosure encompasses peptides capable of binding protein receptors on irradiated tumors. Importantly, the peptides are capable of binding protein receptors on irradiated tumors with high affinity and specificity. By "peptide" is meant an amino acid sequence that includes 5 or more amino acid residues. "Peptide" refers to both short chains, commonly referred to as peptides, oligopeptides, or oligomers, and to longer chains, up to about 100 residues in length. In an exemplary embodiment, peptides of the invention specifically bind to epitopes of proteins exposed on irradiated tumor cells. For instance, peptides of the invention may bind to extracellular, transmembrane or intracellular epitopes of proteins on irradiated tumor cells. As used herein, an "epitope" is a region on an antigen molecule to which a peptide binds specifically. The epitope can result from a three dimensional sequence formed from residues on different regions of a protein antigen molecule, which, in a native state, are closely apposed due to protein folding, or can result from a linear sequence of a protein or peptide in a denatured conformation. In a specific embodiment, the present invention provides peptides capable of specifically binding the GRP78 protein on an irradiated tumor cell. The inventors discovered that the peptide GIRLRG (SEQ ID NO:1) specifically binds the GRP78 protein on an irradiated tumor cell. As such, an exemplary peptide of the invention is GIRLRG (SEQ ID NO:1). Alternatively, a peptide may be a peptide disclosed in WO 2013/049830, which is hereby incorporated by reference in its entirety.

A peptide of the invention may be subject to various changes, substitutions, insertions, and deletions where such changes provide for certain advantages in its use. Thus, the invention encompasses any of a variety of forms of peptide derivatives that include amides, conjugates with proteins, cyclized peptides, polymerized peptides, conservatively substituted variants, analogs, fragments, peptoids, chemically modified peptides, peptide mimetics, and replacement of Adenoviral knob (See, for example, Mathis et al., *Oncogene* 2005; 24:7775-7791).

Peptides of the invention may comprise naturally occurring amino acids, synthetic amino acids, genetically encoded amino acids, non-genetically encoded amino acids, and combinations thereof. Peptides may include both L-form and D-form amino acids.

Representative non-genetically encoded amino acids may include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids may include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

The term "conservatively substituted variant" refers to a peptide comprising an amino acid residue sequence similar to a sequence of a reference peptide that binds a radiation inducible target in which one or more residues have been conservatively substituted with a functionally similar residue and which displays the targeting activity as described herein. The phrase "conservatively substituted variant" also includes peptides wherein a residue is replaced with a chemically derivatized residue, provided that the resulting peptide displays targeting activity as disclosed herein.

Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Peptides of the present invention also include peptides comprising one or more additions and/or deletions or residues relative to the sequence of a peptide whose sequence is disclosed herein, so long as the requisite targeting activity of the peptide is maintained. The term "fragment" refers to a peptide comprising an amino acid residue sequence shorter than that of a peptide disclosed herein.

The term "peptoid" as used herein refers to a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), a thiopeptide bond (CS—NH), and an N-modified bond (—NRCO—). See e.g. Corringer et al. (1993) J Med Chem 36:166-172; Garbay-Jauregiuberry et al. (1992) Int J Pept Protein Res 39:523-527; Tung et al. (1992) Pept Res 5:115-118; Urge et al. (1992) Carbohydr Res 235:83-93; Pavone et al. (1993) Int J Pept Protein Res 41:15-20.

Peptides of the present invention, including peptoids, may be synthesized by any of the techniques that are known to those skilled in the art of peptide synthesis. Synthetic chemistry techniques, such as a solid-phase Merrifield-type synthesis, may be preferred for reasons of purity, antigenic specificity, freedom from undesired side products, ease of production and the like. A summary of representative techniques can be found in Stewart & Young (1969) Solid Phase Peptide Synthesis. Freeman, San Francisco; Merrifield (1969) Adv Enzymol Relat Areas Mol Biol 32:221-296; Fields & Noble (1990) Int J Pept Protein Res 35:161-214; and Bodanszky (1993) Principles of Peptide Synthesis. 2nd rev. ed. Springer-Verlag, Berlin; New York. Solid phase synthesis techniques can be found in Andersson et al. (2000) Biopolymers 55:227-250, references cited therein, and in U.S. Pat. Nos. 6,015,561, 6,015,881, 6,031,071, and 4,244,946. Peptide synthesis in solution is described by Schröder & Lübke (1965) The Peptides. Academic Press, New York. Appropriate protective groups usable in such synthesis are described in the above texts and in McOmie (1973) Protective Groups in Organic Chemistry. Plenum Press, London, New York. Peptides that include naturally occurring amino acids can also be produced using recombinant DNA technology. In addition, peptides comprising a specified amino acid sequence can be purchased from commercial sources (e.g., Biopeptide Co., LLC of San Diego, Calif. and PeptidoGenics of Livermore, Calif.).

Any peptide or peptide mimetic of the present invention may be used in the form of a pharmaceutically acceptable salt. Suitable acids which are capable of forming a pharmaceutically acceptable salt with the peptides of the present invention include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-di- and tri-alkyl and aryl amines (e.g. triethylamine, diisopropyl amine, methyl amine, dimethyl amine and the like), and optionally substituted ethanolamines (e.g. ethanolamine, diethanolamine and the like).

(b) Linker (B)

According to the invention, a peptide of the invention may be conjugated to a linker. In an embodiment, a peptide may be conjugated to a linker moiety that serves to conjugate the peptide of the invention to a chelator. It is to be understood that conjugation of the peptide to the linker and conjugation of the linker to the chelator will not adversely affect either the targeting function of the peptide or the metal-binding function of the chelator. Suitable linkers include amino acid chains and alkyl chains functionalized with reactive groups for coupling to both the peptide and the chelator. An amino acid chain is the preferred linking group when the chelator is peptidic so that the conjugate can be synthesized in toto by solid-phase techniques.

In an embodiment, the linker may include amino acid side chains, referred to as a peptide linker. Accordingly, additional amino acid residues may be added at the amino terminus of a peptide of the invention for the purpose of providing a linker by which the peptides of the present invention can be conveniently affixed to a label or solid matrix, or carrier. Importantly, an amino acid linker alone does not specifically bind to epitopes exposed on irradiated tumor cells. An amino acid residue linker of the invention must be at least 3 residues. An amino acid residue linker of less than 3 amino acids will not work in a peptide construct of the invention. In an embodiment, an amino acid residue linker may be 3 to 10 residues. In a specific embodiment, an amino acid residue linker comprises 3 to 5 residues. In another specific embodiment, an amino acid residue linker comprises 3 or 4 residues. In an exemplary embodiment, an amino acid residue linker comprises 3 residues. In another exemplary embodiment, an amino acid residue linker comprises 4 residues. In a specific embodiment, an amino acid residue linker consists essentially of 3 to 5 residues. In another specific embodiment, an amino acid residue linker consists essentially of 3 or 4 residues. In an exemplary embodiment, an amino acid residue linker consists essentially of 3 residues. In another exemplary embodiment, an amino acid residue linker consists essentially of 4 residues.

Any amino acid residues may be selected for the linker, provided at least one of the amino acids is selected from the group consisting of lysine, tyrosine, histidine and cysteine. In a specific embodiment, any amino acid residues may be selected for the linker, provided at least one of the amino acids is lysine. In an embodiment, an amino acid residue linker comprises 3 to 5 lysines. In another embodiment, an amino acid residue linker comprises 3 or 4 lysines. In an exemplary embodiment, an amino acid residue linker comprises 3 lysines. In an embodiment, an amino acid residue linker consists essentially of 3 to 5 lysines. In another embodiment, an amino acid residue linker consists essentially of 3 or 4 lysines. In still another embodiment, an amino acid residue linker consists essentially of 3 lysines. In a specific embodiment, an amino acid residue linker comprises at least three amino acids, wherein three amino acids are lysine. In another specific embodiment, an amino acid residue linker comprises four amino acids, wherein three amino acids are lysine. In still another specific embodiment, an amino acid residue linker consists essentially of four amino acids, wherein three amino acids are lysine.

In certain embodiments, a linker further comprises one or more spacers. Spacers are known in the art. Non-limiting examples of spacers include 2-aminoethoxy-2-ethoxy acetic acid (AEEA) linkers, AEEEA linkers, and AEA linkers. In a specific embodiment, a linker further comprises one or more 2-aminoethoxy-2-ethoxy acetic acid (AEEA) linkers.

In another embodiment, an alkyl chain linking group may be coupled to the peptide by reacting the amino group of the N-terminal residue of the peptide of the invention with a first functional group on the alkyl chain, such as a carboxyl group or an activated ester. Subsequently the chelator is attached to the alkyl chain to complete the formation of the complex by reacting a second functional group on the alkyl chain with an appropriate group on the chelator. The second functional group on the alkyl chain is selected from substituents that are reactive with a functional group on the chelator while not being reactive with the N-terminal residue of the peptide. For example, when the chelator incorporates a functional group, such as a carboxyl group or an activated ester, the second functional group of the alkyl chain linking group can be an amino group. It will be appreciated that formation of the conjugate may require protection and deprotection of the functional groups present in order to avoid formation of undesired products. Protection and deprotection are accomplished using protecting groups, reagents, and protocols common in the art of organic synthesis. Particularly, protection and deprotection techniques employed in solid phase peptide synthesis may be used. It will be appreciated that linking groups may alternatively be coupled first to the chelator and then to the peptide of the invention.

(c) Chelator (C)

According to the invention, a chelator may be conjugated to a linker of the invention. As used herein, a "chelator" or "chelating agent" is a molecule that forms multiple chemical bonds with a single metal atom. Prior to forming the bonds, the chelating agent has more than one pair of unshared electrons. The bonds are formed by sharing pairs of electrons with the metal atom.

Examples of chelating agents include, but are not limited to, iminodicarboxylic and polyaminopolycarboxylic reactive groups, diethylenetriaminepentaacetic acid (DTPA), 1,4,7,10-tetraazacyclododecane-1,4,7,10-tetraacetic acid (DOTA), tetramethyl heptanedionate (TMHD), 2,4-pentanedione, ethylenediamine-tetraacetic acid disodium salt (EDTA), ethyleneglycol-O,O'-bis(2-aminoethyl)-N,N,N',N'-tetraacetic acid (EGTA), N-(2-hydroxyethyl)ethylenediamine-N,N',N'-triacetic acid trisodium salt (HEDTA), nitrilotriacetic acid (NTA), and 1,4,8,11-tetraazacyclotetradecane-N,N',N'',N'''-tetraacetic acid (TETA), deferoxamine (DFO), and derivatives thereof.

Chelating agents may be conjugated to a linker of the invention, using the methods generally described in Liu et al., *Bioconjugate Chew.* 12(4):653, 2001; Alter et al., U.S. Pat. No. 5,753,627; and PCT Publication No. WO 91/01144; each of which is hereby incorporated by reference. For example, a chelator may be conjugated to a linker by reacting the free amino group of the side chain of lysine with an appropriate functional group of the chelator, such as a carboxyl group or activated ester. In an embodiment, a chelator may be conjugated to at least one amino acid selected from the group consisting of lysine, tyrosine, histidine and cysteine. In another embodiment, a chelator may be conjugated to at least one lysine of the linker. In another embodiment, a chelator may be conjugated to each lysine of the peptide linker. For example, if the linker is comprised of three lysines then a chelator may be conjugated to each lysine resulting in a peptide construct comprising three chelators. In a specific embodiment, a chelator is DTPA.

A peptide construct of the invention may be complexed, through its attached chelating agent, to a detectable label, thereby resulting in a peptide that is indirectly labeled. Similarly, cytotoxic or therapeutic agents may also be attached via a chelating group to a peptide construct of the invention.

(d) Polyethylene Glycol (D)

A peptide construct of the invention further comprises a polyethylene glycol conjugated to a linker. A polyethylene glycol (PEG) may be functionalized in the same manner as the alkyl chain described above for incorporation in the peptide construct. The incorporation of PEG into the peptide construct improves systemic half-life and reduces dosage frequency. In certain embodiments, PEG may be selected from the group consisting of PEG20 and PEG40.

In a specific embodiment, a peptide construct of the invention may comprise a peptide, a peptide linker, at least one chelator and PEG. In another specific embodiment, a peptide construct of the invention may comprise GIRLRG (SEQ ID NO:1), a peptide linker comprising at least 3 lysines, at least one chelator and PEG selected from the group consisting of PEG20 and PEG40. In still another specific embodiment, a peptide construct of the invention may comprise GIRLRG (SEQ ID NO:1), a peptide linker comprising 3 lysines, a DTPA chelator conjugated to each lysine and PEG selected from the group consisting of PEG20 and PEG40. In another embodiment, a peptide construct of the invention may comprise GIRLRG (SEQ ID NO:1), a peptide linker consisting essentially of 3 lysines, a DTPA chelator conjugated to each lysine and PEG selected from the group consisting of PEG20 and PEG40. In still another embodiment, a peptide construct of the invention may comprise GIRLRG (SEQ ID NO:1), a peptide linker comprising four amino acids, three of which are lysine, a DTPA chelator conjugated to each lysine and PEG selected from the group consisting of PEG20 and PEG40. In an exemplary embodiment, a peptide construct of the invention comprises PEG40-Lys(DTPA)-AEEA-Lys(DTPA)-AEEA-Trp-Lys(DTPA)-AEEA-GIRLRG (SEQ ID NO:1). In another exemplary embodiment, a peptide construct of the invention consists essentially of PEG40-Lys(DTPA)-AEEA-Lys(DTPA)-AEEA-Trp-Lys(DTPA)-AEEA-GIRLRG (SEQ ID NO:1).

(e) Detectable Label

According to the invention, a peptide construct of the invention may comprise a detectable label. In an embodiment, the detectable label may be complexed with a chelating agent that is conjugated to the peptide. In another embodiment, the detectable label may be complexed with a chelating agent that is conjugated to a linker that is conjugated to the peptide. In still another embodiment, the detectable label may be coupled to a linker that is conjugated to the peptide. In still yet another embodiment, a detectable label may be indirectly attached to a peptide of the invention by the ability of the label to be specifically bound by a second molecule. One example of this type of an indirectly attached label is a biotin label that can be specifically bound by the second molecule, streptavidin. Single, dual or multiple labeling may be advantageous.

As used herein, a "detectable label" is any type of label which, when attached to a peptide of the renders the peptide detectable. A detectable label may also be toxic to cells or cytotoxic. In general, detectable labels may include luminescent molecules, chemiluminescent molecules, fluorochromes, fluorophores, fluorescent quenching agents, colored molecules, radioisotopes, radionuclides, cintillants, massive labels such as a metal atom (for detection via mass changes), biotin, avidin, streptavidin, protein A, protein G, antibodies or fragments thereof, Grb2, polyhistidine, $Ni^{2+}$, Flag tags, myc tags, heavy metals, enzymes, alkaline phosphatase, peroxidase, luciferase, electron donors/acceptors, acridinium esters, and colorimetric substrates. In a specific embodiment, the detectable label is a radionuclide. The skilled artisan would readily recognize other useful labels that are not mentioned above, which may be employed in the operation of the present invention.

A detectable label emits a signal that can be detected by a signal transducing machine. In some cases, the detectable label can emit a signal spontaneously, such as when the detectable label is a radionuclide. In other cases the detectable label emits a signal as a result of being stimulated by an external field such as when the detectable label is a relaxivity metal. Examples of signals include, without limitation, gamma rays, X-rays, visible light, infrared energy, and radiowaves. Examples of signal transducing machines include, without limitation, gamma cameras including SPECT/CT devices, PET scanners, fluorimeters, and Magnetic Resonance Imaging (MRI) machines. As such, the detectable label comprises a label that can be detected using magnetic resonance imaging, scintigraphic imaging, ultrasound, or fluorescence.

Suitable fluorophores include, but are not limited to, fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes. A peptide of the invention can be labeled for fluorescence detection by labeling the agent with a fluorophore using techniques well known in the art (see, e.g., Lohse et al., Bioconj Chem 8:503-509 (1997)). For example, many known dyes are capable of being coupled to $NH_2$-terminal amino acid residues. Alternatively, a fluorochrome such as fluorescein may be bound to a lysine residue of the peptide linker.

A radionuclide may be a γ-emitting radionuclide, Auger-emitting radionuclide, β-emitting radionuclide, an α-emitting radionuclide, or a positron-emitting radionuclide. A radionuclide may be a detectable label and/or a cytotoxic agent. Non-limiting examples of suitable radionuclides may include carbon-11, nitrogen-13, oxygen-15, fluorine-18, fluorodeoxyglucose-18, phosphorous-32, scandium-47, copper-64, 65 and 67, gallium-67 and 68, bromine-75, 77 and 80m, rubidium-82, strontium-89, zirconium-89, yttrium-86 and 90, ruthenium-95, 97,103 and 105, rhenium-99m, 101, 105, 186 and 188, technetium-99m, rhodium-105, mercury-107, palladium-109, indium-111, silver-111, indium-113m, lanthanide-114m, tin-117m, tellurium-121m, 122m and 125m, iodine-122, 123, 124, 125, 126, 131 and 133, praseodymium-142, promethium-149, samarium-153, gadolinium-159, thulium-165, 167 and 168, dysprosium-165, holmium-166, lutetium-177, rhenium-186 and 188, iridium-192, platinum-193 and 195m, gold-199, thallium-201, titanium-201, astatine-211, bismuth-212 and 213, lead-212, radium-223, actinium-225, and nitride or oxide forms derived there from. In a specific embodiment, a radionuclide is selected from the group consisting of copper-64, zirconium-89, yttrium-90, indium-111, and lutetium-177. In another specific embodiment, a radionuclide is selected from the group consisting of yttrium-90, indium-111, and lutetium-177. In an exemplary embodiment, a radionuclide is indium-111.

A variety of metal atoms may be used as a detectable label. The metal atom may generally be selected from the group of metal atoms comprised of metals with an atomic number of twenty or greater. For instance, the metal atoms may be calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms. In some embodiments, the metal atoms may be selected from the group comprising alkali metals with an atomic number greater than twenty. In other embodiments, the metal atoms may be selected from the group comprising alkaline earth metals with an atomic number greater than twenty. In one embodiment, the metal atoms may be selected from the group of metals comprising the lanthanides. In another embodiment, the metal atoms may be selected from the group of metals comprising the actinides. In still another embodiment, the metal atoms may be selected from the group of metals comprising the transition metals. In yet another embodiment, the metal atoms may be selected from the group of metals comprising the poor metals. In other embodiments, the metal atoms may be selected from the group comprising gold atoms, bismuth atoms, tantalum atoms, and gadolinium atoms. In preferred embodiments, the metal atoms may be selected from the group comprising metals with an atomic number of 53 (i.e. iodine) to 83 (i.e. bismuth). In an alternative embodiment, the metal atoms may be atoms suitable for magnetic resonance imaging. In another alternative embodiment, the metal atoms may be selected from the group consisting of metals that have a K-edge in the x-ray energy band of CT. Preferred metal atoms include, but are not limited to, manganese, iron, gadolinium, gold, and iodine.

The metal atoms may be metal ions in the form of +1, +2, or +3 oxidation states. For instance, non-limiting examples include $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide. For instance, non-limiting examples of metal oxides may include iron oxide, manganese oxide, or gadolinium oxide. Additional examples may include magnetite, maghemite, or a combination thereof.

According to the invention, a peptide construct comprising a chelating agent may incorporate a radionuclide or metal atom. Incorporation of the radionuclide or metal atom with a peptide-chelating agent complex may be achieved by various methods common in the art of coordination chemistry. For example, when the metal is technetium-99m, the following general procedure may be used to form a technetium complex. A peptide-chelating agent complex solution is formed initially by dissolving the complex in aqueous alcohol such as ethanol. The solution is then degassed to remove oxygen then thiol protecting groups are removed with a suitable reagent, for example, with sodium hydroxide, and then neutralized with an organic acid, such as acetic acid (pH 6.0-6.5). In the labeling step, a stoichiometric excess of sodium pertechnetate, obtained from a molybdenum generator, is added to a solution of the complex with an amount of a reducing agent such as stannous chloride sufficient to reduce technetium and heated. The labeled complex may be separated from contaminants $^{99m}TcO_4^-$ and colloidal $^{99m}TcO_2$ chromatographically, for example, with a C-18 Sep Pak cartridge.

In an alternative method, labeling can be accomplished by a transchelation reaction. The technetium source is a solution of technetium complexed with labile ligands facilitating ligand exchange with the selected chelator. Suitable ligands for transchelation include tartarate, citrate, and heptagluconate. In this instance the preferred reducing reagent is sodium dithionite. It will be appreciated that the complex may be labeled using the techniques described above, or alternatively the chelator itself may be labeled and subsequently conjugated to the peptide construct of the invention to form the complex; a process referred to as the "prelabeled ligand" method.

Another approach for labeling complexes of the present invention involves immobilizing the peptide-chelating agent complex on a solid-phase support through a linkage that is cleaved upon metal chelation. This is achieved when the chelating agent is coupled to a functional group of the support by one of the complexing atoms. Preferably, a complexing sulfur atom is coupled to the support which is functionalized with a sulfur protecting group such as maleimide.

Still another approach for labeling peptide constructs of the present invention involves incubation with a desire radionuclide. For example, peptide constructs comprising a peptide of the invention, a linker, one or more chelators and PEG may be dissolved in ammonium acetate buffer. Ammonium acetate may be added to a $^{111}InCl_3$ stock solution and carefully mixed; the final pH should be between about 5.5-5.8. The $^{111}InCl_3$ may then be added to the peptide construct at a ratio of about 370:1 kBq:μg and the reaction mixture may be incubated at about 95° C. with constant shaking for about 1 h. The radiolabeling efficiency of the peptide construct may be determined using instant thin-layer chromatography.

In another embodiment, a detectable label may be coupled directly or indirectly to a peptide without the use of a chelating agent. For example, the detectable label is coupled to a linker that is coupled to a peptide of the invention. For example, a radioactive iodine label (e.g., $^{122}I$, $^{123}I$, $^{124}I$, $^{125}I$, or $^{131}I$) is capable of being coupled to each D- or L-Tyr or D- or L-4-amino-Phe residue present in a peptide linker of the invention. In an embodiment, a tyrosine residue of a peptide linker of the invention may be halogenated. Halogens include fluorine, chlorine, bromine, iodine, and astatine. Such halogenated peptides of the invention may be detectably labeled if the halogen is a radioisotope, such as, for example, $^{18}F$, $^{75}Br$, $^{77}Br$, $^{122}I$, $^{123}I$, $^{124}I$, $^{125}I$, $^{129}I$, $^{131}I$, or $^{211}At$. Halogenated peptides of the invention contain a halogen covalently bound to at least one amino acid, and preferably to D-Tyr residues present in the peptide linker.

(f) Therapeutic Agent

In certain embodiments, a peptide construct of the invention may be coupled to a therapeutic agent, such that the therapeutic agent can be selectively targeted to an irradiated tumor. The therapeutic agent may be directly coupled to the peptide or may be indirectly coupled to the peptide. In an embodiment, the therapeutic agent may be complexed with a chelating agent that is conjugated to the peptide. In a specific embodiment, the therapeutic agent may be complexed with a chelating agent that is conjugated to a linker that is conjugated to the peptide. In still another embodiment, the therapeutic agent may be conjugated to a linker that is conjugated to the peptide. In still yet another embodiment, the therapeutic agent may be conjugated to a linker that is conjugated to a chelating agent that is complexed with a detectable label.

A "therapeutic agent" is any compound known in the art that is used in the detection, diagnosis, or treatment of cancer. Such compounds may be naturally-occurring, modified, or synthetic. In certain embodiments, the therapeutic agent may be a radionuclide. The therapeutic agent preferably reduces or interferes with tumor growth or otherwise reduces the effect of the tumor within the body or organism. A therapeutic agent that reduces the symptoms produced by the tumor or reduces tumor growth is suitable for the present invention. Additionally, any therapeutic agent that reduces the symptoms associated with tumor cell growth will work for purposes of the present invention. Non-limiting examples of therapeutic agents may include drugs, therapeutic compounds, genetic materials, metals (such as radioactive isotopes), proteins, peptides, carbohydrates, lipids, steroids, nucleic acid based materials, or derivatives, analogues, or combinations thereof in their native form or derivatized with hydrophobic or charged moieties to enhance incorporation or adsorption into a cell. Such therapeutic agents may be water soluble or may be hydrophobic. Non-limiting examples of therapeutic agents may include immune-related agents, thyroid agents, respiratory products, antineoplastic agents, anti-helmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. Non-limiting examples of therapeutic agents are described below. A peptide construct of the invention may be coupled to one, two, three, four, or five therapeutic agents. Methods of coupling a peptide construct to a therapeutic agent are known in the art. Generally speaking, the coupling should not interfere with the peptide recognizing its target. In some instances, a peptide may be generated with a cleavable linkage between the peptide and therapeutic agent. Such a linker may allow release of the therapeutic agent at a specific cellular location.

A therapeutic agent of the invention may be a small molecule therapeutic, a therapeutic nucleic acid, or a chemotherapeutic agent. A representative therapeutic nucleic acid may encode a polypeptide having an ability to induce an immune response and/or an anti-angiogenic response in vivo. Representative therapeutic proteins with immunostimulatory effects include but are not limited to cytokines (e.g., an interleukin (IL) such as IL2, IL4, IL7, IL12, interferons, granulocyte-macrophage colony-stimulating factor (GM-CSF), tumor necrosis factor alpha (TNF-α)), immunomodulatory cell surface proteins (e.g., human leukocyte antigen (HLA proteins), co-stimulatory molecules, and tumor-associated antigens. See Kirk & Mule, 2000; Mackensen et al., 1997; Walther & Stein, 1999; and references cited therein. Representative proteins with anti-angiogenic activities that can be used in accordance with the presently disclosed subject matter include: thrombospondin I (Kosfeld & Frazier, 1993; Tolsma et al., 1993; Dameron et al., 1994), metallospondin proteins (Carpizo & Iruela-Arispe, 2000), class I interferons (Albini et al., 2000), IL12 (Voest et al., 1995), protamine (Ingber et al., 1990), angiostatin (O'Reilly et al., 1994), laminin (Sakamoto et al., 1991), endostatin (O'Reilly et al., 1997), and a prolactin fragment (Clapp et al., 1993). In addition, several anti-angiogenic peptides have been isolated from these proteins (Maione et al., 1990; Eijan et al., 1991; Woltering et al., 1991). Representative proteins with both immunostimulatory and anti-angiogenic activities may include IL12, interferon-γ, or a chemokine. Other therapeutic nucleic acids that may be useful for cancer therapy include but are not limited to nucleic acid sequences encoding tumor suppressor gene products/antigens, antimetabolites, suicide gene products, and combinations thereof.

A chemotherapeutic agent refers to a chemical compound that is useful in the treatment of cancer. The compound may be a cytotoxic agent that affects rapidly dividing cells in general, or it may be a targeted therapeutic agent that affects the deregulated proteins of cancer cells. A cytotoxic agent is any naturally-occurring, modified, or synthetic compound that is toxic to tumor cells. Such agents are useful in the treatment of neoplasms, and in the treatment of other symptoms or diseases characterized by cell proliferation or a hyperactive cell population. The chemotherapeutic agent may be an alkylating agent, an anti-metabolite, an anti-tumor antibiotic, an anti-cytoskeletal agent, a topoisomerase inhibitor, an anti-hormonal agent, a targeted therapeutic agent, a photodynamic therapeutic agent, or a combination thereof. In an exemplary embodiment, the chemotherapeutic agent is selected from the group consisting of liposomal doxorubicin and nanoparticle albumin docetaxel.

Non-limiting examples of suitable alkylating agents may include altretamine, benzodopa, busulfan, carboplatin, carboquone, carmustine (BCNU), chlorambucil, chlornaphazine, cholophosphamide, chlorozotocin, cisplatin, cyclosphosphamide, dacarbazine (DTIC), estramustine, fotemustine, ifosfamide, improsulfan, lipoplatin, lomustine (CCNU), mafosfamide, mannosulfan, mechlorethamine, mechlorethamine oxide hydrochloride, melphalan, meturedopa, mustine (mechlorethamine), mitobronitol, nimustine, novembichin, oxaliplatin, phenesterine, piposulfan, prednimustine, ranimustine, satraplatin, semustine, temozolomide, thiotepa, treosulfan, triaziquone, triethylenemelamine, triethylenephosphoramide (TEPA), triethylenethiophosphaoramide (thiotepa), trimethylolomelamine, trofosfamide, uracil mustard and uredopa.

Suitable anti-metabolites may include, but are not limited to aminopterin, ancitabine, azacitidine, 8-azaguanine, 6-azauridine, capecitabine, carmofur (1-hexylcarbomoyl-5-fluorouracil), cladribine, clofarabine, cytarabine (cytosine arabinoside (Ara-C)), decitabine, denopterin, dideoxyuridine, doxifluridine, enocitabine, floxuridine, fludarabine, 5-fluorouracil, gemcetabine, hydroxyurea (hydroxycarbamide), leucovorin (folinic acid), 6-mercaptopurine, methotrexate, nafoxidine, nelarabine, oblimersen, pemetrexed, pteropterin, raltitrexed, tegofur, tiazofurin, thiamiprine, tioguanine (thioguanine), and trimetrexate.

Non-limiting examples of suitable anti-tumor antibiotics may include aclacinomysin, aclarubicin, actinomycins, adriamycin, aurostatin (for example, monomethyl auristatin E), authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, epoxomicin, esorubicin, idarubicin, marcellomycin, mitomycins, mithramycin, mycophenolic acid, nogalamycin, olivomycins, peplomycin, plicamycin, potfiromycin, puromycin, quelamycin, rodorubicin, sparsomycin, streptonigrin, streptozocin, tubercidin, valrubicin, ubenimex, zinostatin, and zorubicin.

Non-limiting examples of suitable anti-cytoskeletal agents may include cabazitaxel, colchicines, demecolcine, docetaxel, epothilones, ixabepilone, macromycin, omacetaxine mepesuccinate, ortataxel, paclitaxel (for example, DHA-paclitaxel), taxane, tesetaxel, vinblastine, vincristine, vindesine, and vinorelbine.

Suitable topoisomerase inhibitors may include, but are not limited to, amsacrine, etoposide (VP-16), irinotecan, mitoxantrone, RFS 2000, teniposide, and topotecan.

Non-limiting examples of suitable anti-hormonal agents may include aminoglutethimide, antiestrogen, aromatase inhibiting 4(5)-imidazoles, bicalutamide, finasteride, flutamide, fluvestrant, goserelin, 4-hydroxytamoxifen, keoxifene, leuprolide, LY117018, mitotane, nilutamide, onapristone, raloxifene, tamoxifen, toremifene, and trilostane.

Examples of targeted therapeutic agents may include, without limit, monoclonal antibodies such as alemtuzumab, cartumaxomab, edrecolomab, epratuzumab, gemtuzumab, gemtuzumab ozogamicin, glembatumumab vedotin, ibritumomab tiuxetan, reditux, rituximab, tositumomab, and trastuzumab; protein kinase inhibitors such as bevacizumab, cetuximab, crizonib, dasatinib, erlotinib, gefitinib, imatinib, lapatinib, mubritinib, nilotinib, panitumumab, pazopanib, sorafenib, sunitinib, toceranib, and vandetanib.

Non limiting examples of angiogeneisis inhibitors may include angiostatin, bevacizumab, denileukin diftitox, endostatin, everolimus, genistein, interferon alpha, interleukin-2, interleukin-12, pazopanib, pegaptanib, ranibizumab, rapamycin (sirolimus), temsirolimus, and thalidomide.

Non limiting examples of growth inhibitory polypeptides may include bortazomib, erythropoietin, interleukins (e.g., IL-1, IL-2, IL-3, IL-6), leukemia inhibitory factor, interferons, romidepsin, thrombopoietin, TNF-α, CD30 ligand, 4-1BB ligand, and Apo-1 ligand.

Non-limiting examples of photodynamic therapeutic agents may include aminolevulinic acid, methyl aminolevulinate, retinoids (alitretinon, tamibarotene, tretinoin), and temoporfin.

Other antineoplastic agents may include anagrelide, arsenic trioxide, asparaginase, bexarotene, bropirimine, celecoxib, chemically linked Fab, efaproxiral, etoglucid, ferruginol, lonidamide, masoprocol, miltefosine, mitoguazone, talapanel, trabectedin, and vorinostat.

Also included are pharmaceutically acceptable salts, acids, or derivatives of any of the above listed agents. The dose of the chemotherapeutic agent can and will vary depending upon the agent and the type of tumor or neoplasm. A skilled practitioner will be able to determine the appropriate dose of the chemotherapeutic agent.

Other therapeutic agents may comprise a virus or a viral genome such as an oncolytic virus. An oncolytic virus comprises a naturally occurring virus that is capable of killing a cell in the target tissue (for example, by lysis) when it enters such a cell.

(g) Pharmaceutical Composition

The peptide constructs of the present invention may further comprise a drug carrier to facilitate drug preparation and administration. Any suitable drug delivery vehicle or carrier may be used, including but not limited to a gene therapy vector (e.g., a viral vector or a plasmid), a microcapsule, for example a microsphere or a nanosphere (Manome et al., 1994; Hallahan, 2001a; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786, 387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997 and U.S. Pat. Nos. 4,551, 482, 5,714,166, 5,510,103, 5,490,840, and 5,855,900), and a polysome (U.S. Pat. No. 5,922,545).

Additionally, the peptide constructs may be formulated into pharmaceutical compositions and administered by a number of different means that may deliver a therapeutically effective dose. Such compositions may be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations and formulations for parenteral administration may be prepared as described above. Solid dosage forms for oral administration may include capsules, tablets, pills, powders, and granules. In such solid dosage forms, the peptide construct is ordinarily combined with one or more adjuvants appropriate to the indicated route of administration. If administered per os, the composition can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as can be provided in a dispersion of active composition of the invention in hydroxypropylmethyl cellulose. In the case of capsules, tablets, and pills, the dosage forms may also comprise buffering agents such as sodium citrate, or magnesium or calcium carbonate or bicarbonate. Tablets and pills may additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The amount of the peptide construct of the invention that may be combined with the carrier materials to produce a single dosage of the composition can and will vary depending upon the subject, the peptide, the formulation, and the particular mode of administration. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

In certain embodiments, a composition comprising a peptide construct of the invention is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating peptide constructs into delivery vehicles are known in the art.

In one alternative embodiment, a liposome delivery vehicle may be utilized. Liposomes, depending upon the embodiment, are suitable for delivery of the peptide construct of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the peptide construct of the invention may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the peptide construct of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a peptide construct of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The peptide construct of the invention may be encapsulated in a microemulsion by any method generally known in the art.

In yet another embodiment, a peptide construct of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate peptide constructs of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Method of Use

In another aspect, a composition of the present invention, as described above, may be used in treating, stabilizing and preventing cancer and associated diseases in a subject. The method comprises exposing a target area of the subject where the presence of a tumor is suspected to ionizing radiation and administering to the subject a composition comprising a peptide construct of the invention that specifically binds a protein exposed on an irradiated cell. By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. In a desired embodiment, the percent of tumor or cancerous cells surviving the treatment is at least 20, 40, 60, 80, or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of a peptide of the invention is at least 2, 5, 10, 20, or 50-fold greater than the decrease in the number of non-tumor or non-cancerous cells. Desirably, the methods of the present invention result in a decrease of 20, 40, 60, 80, or 100% in the size of a tumor or in the number of cancerous cells, as determined using standard methods. Desirably, at least 20, 40, 60, 80, 90, or 95% of the treated subjects have a complete remission in which all evidence of the tumor or cancer disappears. Desirably, the tumor or cancer does not reappear or reappears after at least 5, 10, 15, or 20 years.

The peptides of the present invention may be complexed with radionuclides as described above in order to provide specific delivery of radiation to the site of a tumor. Further, the composition of the present invention may be part of a combination therapy. Preferably, a combination therapy would include the use of the peptide construct of the present invention along with a radiation therapy or chemotherapy course of treatment. It has also been suggested that peptide construct compositions, such as those described herein, may increase the susceptibility of tumor cells to the effects of chemotherapy or radiation. In preferred embodiments, the composition of the invention may be used to enhance the efficacy of cancer radiotherapy.

In yet another aspect, the present invention provides a method of detecting a tumor in a subject. The method comprises exposing a target area of the subject where the presence of a tumor is suspected to ionizing radiation, administering to the subject a composition comprising a peptide construct of the invention complexed with a radionuclide, and detecting the radionuclide to detect binding of the peptide to a cell in the subject, wherein the presence of the radionuclide indicates the presence of a tumor in the target area of the subject. In preferred embodiments, the method may be used to diagnose or image a cancer in a subject. In some embodiments, a method for detecting a tumor can comprise (a) exposing a suspected tumor to ionizing radiation; (b) biopsying a suspected tumor; (c) contacting a peptide construct of the invention complexed with a radionuclide with the suspected tumor in vitro; and (d) detecting the radionuclide, whereby a tumor is diagnosed.

Binding may be detected using microscopy (fluorescent microscopy, confocal microscopy, or electron microscopy), magnetic resonance imaging (including MTI, MRS, DWI and fMRI), scintigraphic imaging (SPECT (Single Photon Emission Computed Tomography), PET (Positron Emission Tomography), gamma camera imaging, and rectilinear scanning), radiography, or ultrasound. The radionuclide may be detectable in situ, in vivo, ex vivo, and in vitro.

The peptide compositions are as described in Section I above. The subject, the cancer, the radiotherapy, and the administration of the compositions are described below.

(a) Subject

A method of the invention may be used to detect or treat a tumor in a subject that is a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc.

(b) Tumor

A peptide construct of the invention may be used to treat or recognize a tumor derived from a neoplasm or a cancer. "Neoplasm" is any tissue, or cell thereof, characterized by abnormal growth as a result of excessive cell division. The neoplasm may be malignant or benign, the cancer may be primary or metastatic; the neoplasm or cancer may be early stage or late stage. Non-limiting examples of neoplasms or cancers that may be treated or detected include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In a specific embodiment, the cancer is selected from the group consisting of bladder carcinoma, breast carcinoma, cervical carcinoma, cholangiocarcinoma, colorectal carcinoma, esophageal carcinoma, gastric sarcoma, glioma, lung carcinoma, lymphoma, melanoma, multiple myeloma, osteosarcoma, ovarian carcinoma, pancreatic carcinoma, prostate carcinoma, stomach carcinoma, a head, a neck tumor, and a solid tumor. In an exemplary embodiment, the cancer is selected from the group consisting of esophageal cancer, glioma, cervical cancer, lung cancer and breast cancer.

(c) Exposing to Ionizing Radiation—Radiotherapy

In an aspect, the method comprises exposing a target area of a subject where the presence of a tumor is suspected to ionizing radiation. Low doses of radiation can be used for selective targeting using the peptide construct compositions disclosed herein. In some embodiments, the dose of radiation comprises up to about 2 Gy ionizing radiation. Higher radiation doses can also be used, especially in the case of local radiation treatment as described herein below.

Radiation can be localized to a tumor using conformal irradiation, brachytherapy, or stereotactic irradiation. The threshold dose for inductive changes can thereby be exceeded in the target tissue but avoided in surrounding normal tissues. A "target tissue" as used herein refers to an intended site for accumulation of a peptide construct following administration to a subject. For example, the methods disclosed herein can employ a target tissue comprising an irradiated tumor. A "control tissue" as used herein refers to a site suspected to substantially lack binding and/or accumulation of an administered peptide construct. For example, in accordance with the methods of the presently disclosed subject matter, a non-irradiated tumor and a non-cancerous tissue are control tissues. In some embodiments, doses of at least about 2 Gy ionizing radiation can be used, and in some embodiments a dose of about 10 Gy to about 20 Gy ionizing radiation can be used. For treatment of a subject having two or more tumors, local irradiation enables differential drug administration and/or dose at each of the two or more tumors. Alternatively, whole body irradiation can be used, as permitted by the low doses of radiation required for targeting of peptide constructs disclosed herein. Radiotherapy methods suitable for use in the practice of the presently disclosed subject matter can be found in Leibel & Phillips, 1998, among other sources.

In an embodiment, the radiation treatment comprises administration of less than about 2 Gy ionizing radiation. In another embodiment, the radiation treatment comprises at least about 2 Gy ionizing radiation, in some embodiments about 2 Gy to about 3 Gy ionizing radiation, and in some embodiments about 2 Gy to about 6 Gy ionizing radiation. In other embodiments, radiation treatment comprises about 10 Gy to about 20 Gy ionizing radiation.

Administration of a composition to a subject can be performed by irradiating the tumor prior to, concurrent with, or subsequent to administration of a composition of the invention. Accordingly, the tumor is irradiated in some embodiments 0 hours to about 24 hours before administration of the composition, and in some embodiments about 4 hours to about 24 hours before administration of the composition.

(d) Administration

In certain aspects, a pharmacologically effective amount of a peptide construct of the invention may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the peptides useful in this discovery, making them more lipophilic, for example, by encapsulating them in liposomes or by blocking polar groups.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

For therapeutic applications, a therapeutically effective amount of a composition of the invention is administered to a subject. A "therapeutically effective amount" is an amount of the therapeutic composition sufficient to produce a measurable biological tumor response (e.g., an immunostimulatory, an anti-angiogenic response, a cytotoxic response, or tumor regression). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

For diagnostic applications, a detectable amount of a composition of the invention is administered to a subject. A "detectable amount", as used herein to refer to a diagnostic composition, refers to a dose of such a composition that the presence of the composition can be determined in vivo or in vitro. A detectable amount will vary according to a variety of factors, including but not limited to chemical features of the drug being labeled, the detectable label, labeling methods, the method of imaging and parameters related thereto, metabolism of the labeled drug in the subject, the stability of the label (e.g. the half-life of a radionuclide label), the time elapsed following administration of the drug and/or labeled peptide construct prior to imaging, the route of drug administration, the physical condition and prior medical history of the subject, and the size and longevity of the tumor or suspected tumor. Thus, a detectable amount can vary and can be tailored to a particular application. After study of the present disclosure, and in particular the Examples, it is within the skill of one in the art to determine such a detectable amount.

The frequency of dosing may be daily or once, twice, three times or more per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Although the foregoing methods appear the most convenient and most appropriate and effective for administration of peptide constructs, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

Typical dosage levels can be determined and optimized using standard clinical techniques and will be dependent on the mode of administration.

III. Kits

In another aspect, a kit is provided for use in diagnostic or therapeutic embodiments of the invention. The kit includes a peptide construct of the invention, preferably a peptide comprising SEQ ID NO:1, and a detectable label (radionuclide), as described in Section I. In an embodiment, each component of the kit (a peptide construct and a detectable label (radionuclide)) is separately packaged in the kit. In another preferred embodiment, the kit includes a predetermined amount of the peptide construct and the detectable label (radionuclide) (e.g., an amount sufficient for diagnosing or treating cancer in a subject). The peptide construct and/or the detectable label (radionuclide) can be lyophilized to enable long-term storage. The peptide and/or detectable label (radionuclide) may be sealed in a sterilized container. The kit preferably includes instructions for using the kit and its contents.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: A Radiolabeled Peptide to GRP78 Specifically Targets to Tumors

GRP78 expression and cancer cell surface expression are induced by radiation (Passarella, 2010). GRP78 surface expression is accessible to binding ligands that induce pro-survival signaling through AKT and leads to lung cancer resistance to therapy. GRP78 is mobilized in cancer during the radiation response. GRP78 is highly expressed in a wide range of cancers through extrinsic factors including glucose deprivation, hypoxia and acidosis in the microenvironment of cancer. The induction of ER stress leads to an increase in GRP78 in the ER compartment, as well as GRP78 transport from the ER to the cell surface. GRP78 is a co-receptor for cell-surface signaling. Through the formation of complexes with other proteins on the cell surface, GRP78 mediates enhanced viability in cancer cells. Cell-surface GRP78 acts as a receptor for α2-macroglobulin.

As such, the lead peptide to Glucose Regulatory Protein-78 (GRP78) has been PEGylated to improve the duration of circulation. Further, peptide ligands have been conjugated to liposomes to improve drug delivery to cancer. Likewise, peptides conjugated to nanoparticles improve delivery of cytotoxic agents to cancer. Finally, radiopharmaceuticals, such as $^{90}Y$, can be conjugated to the PEGylated peptide.

Phage displayed peptide libraries were used to identify peptides that bind within irradiated cancers in mouse models. 42 unique peptides were discovered that will specifically bind within cancers in mice following irradiation. These peptides were then used for affinity purification of the binding partner in cancer (Hariri, 2010; Passarella, 2010). Over a dozen radiation inducible proteins were discovered using this approach. Proteins were prioritized based upon the duration of expression, specificity to cancer and accessibility to peptide and nanoparticle binding. This approach challenges the paradigm of targeting only constitutively expressed proteins in cancer. Inducible proteins increase the number of molecular targets for peptide development. The lead peptide, GIRLRG (SEQ ID NO:1), binds selectively to irradiated cancer. This platform technology and this new paradigm in treating cancer holds promise to improve both drug development and treatment of cancer. This new paradigm will expand the number of therapeutic targets for peptide selection and development. This approach will also add an additional method for treating lung cancer.

The GIRLRG (SEQ ID NO:1) peptide conjugated to a poly-lysine linker for DOTA and DTPA conjugation was first studied. This peptide-conjugate cleared quickly from the circulation and binds briefly to cancer. The duration of tumor binding was improved by PEGylation, with longer circulation times and prolonged imaging in cancer. Surprisingly, conjugating PEG to the free carboxyl-end of the peptide eliminated cancer binding, so the carboxyl end (Arg) is essential for cancer binding. Both PEG20 and PEG40 are effective at enhancing prolonged binding in cancer. Radioiodination of the peptide linker region was possible, but the PEG-peptide was rapidly de-iodinated and therefore tumor binding could not be monitored by imaging. DTPA conjugation to Lysine in the linker region maintained cancer specific binding. The optimized construct is:

(SEQ ID NO: 1)
mPEG40K-carbonyl-Lys(CHX-A"-DTPA)-AEEAc-Lys(CHX-A"-DTPA)-AEEAc-Trp-Lys(CHX-A"-DTPA)-AEEAc-GIRLRG PEG-GIRLRG (SEQ ID NO:1) was 8 nm and did not aggregate even after heating. SPECT images of the spatial and temporal pharmacokinetics of $^{111}$In-labeled PEG-GIRLRG and $^{111}$In-labeled control peptide within irradiated mouse A549 tumors is shown in FIG. 1. At 7 days after administration, gamma emission from each of the organs and tumors of mice injected with PEG-GIRLRG (SEQ ID NO:1) and PEG-control peptide was measured (FIG. 2). PEG-GIRLRG (SEQ ID NO:1) selectively bound to tumors, whereas the control peptide did not. Further, PEG-GIRLRG (SEQ ID NO:1) did not bind to irradiated normal tissue.

The cancer selective binding of $^{111}$In-labeled PEG-GIRLRG (SEQ ID NO:1) was also found in cervix, esophageal and brain tumors at 72 hours following administration (FIG. 3). The right hind limb tumor was treated with 3 Gy and left hind limb tumor is an untreated (0Gy) internal control in the same mouse.

Example 2: Characterization of the Radiolabeled Peptide in Mouse Models of Cancer A preclinical imaging study will be conducted to test that the radiation inducible receptor is expressed specifically in cancer during radiotherapy. The first objective is to determine whether DPTA-PEG-GIRLRG (SEQ ID NO:1) binds selectively within irradiated mouse models of human cancer. The second objective is to determine the pharmacokinetics of the radiolabeled peptide to assist in future clinical study design. Preliminary data shows that $^{111}$In-GIRLRG (SEQ ID NO:1) binds within irradiated cancers. $^{111}$In-labeled peptides are studied because of the longer half life. FIG. 1 and FIG. 3 show the feasibility of SPECT imaging of radiolabeled peptide. Additionally, DTPA-PEG-GIRLRG (SEQ ID NO:1) has also been conjugated to liposomes and nanoparticles to accomplish targeted drug delivery.

Radiolabeling of DTPA-PEG-GIRLRG (SEQ ID NO: 1). Of the various imaging agents, Indium-111 ($^{111}$In) was chosen as the radiolabel due to its suitable half-life for SPECT imaging. The well-established radiopharmaceutical chemistry is 500 μl of 0.5 M ammonium acetate pH 8.1 chelex buffer to 500 μl of $^{111}$In (pH 1.5-1.9) of $^{111}$InCl$_3$. DTPA-PEG-peptide will be labeled with $^{111}$In at specific activity 10 mCi/mg. 460 μl of 0.1M ammonium acetate pH 5.5 chelex buffer will be added to acid washed tubes, and 300 μg of DTPA-PEG-peptide (60 μl, concentration 5 mg/ml) will then be added. 3 mCi of $^{111}$InCl$_3$ solution pH 5.8-6.1 will then be added and incubated at 65° C. for 1 h. 4 μl of the reaction mixture will be aliquoted, and 1 μl of 50 mM DTPA to bind to free $^{111}$In will be added, and incubated at 37° C. for 5 min, then quality control (QC) will be performed. ITLC will be performed (mobile phase is 50 mM DTPA). $^{111}$In-DTPA moves with the solvent front and $^{111}$In-DTPA-PEG-peptide remains at the origin. If labeling is less than 95%, the reaction will be spun in a desalting column (7 kDa). Anything less than 7 kDa will stay on the column and $^{111}$In-DTPA-PEG-peptides will elute through the column. QC will be repeated with ITLC. Radiolabeling of peptide with $^{111}$In requires pH changes and heating. If aggregation or loss of specificity for cancer is observed, DOTA or DFO as chelators of Cu-64 and Zr-89, respectively, will be studied.

PEG-GIRLRG (SEQ ID NO:1) biodistribution studies. Tumor uptake of a radiolabeled drug can be affected by the tracer protein dose and timing of tissue collection. Usually a low tracer dose with high radiolabeling specific activity is preferred to avoid induction of a pharmacological effect and to prevent saturation of the receptors/antigens in vivo. However, this is not ideal for all targets, especially when the targets are expressed on healthy tissue. If the injected tracer dose is low, these organs can serve as a sink and bind high amounts of the radiotracer, thereby preventing the tracer from reaching the tumor cells. Increasing the tracer mass can potentially saturate the receptors on healthy organs, since their expression is often relatively low compared to the tumor. This will result in increased uptake of the tracer in the tumor and improved imaging contrast between tumor and normal organs. The effect of specific activity on $^{111}$In labeled peptide for optimized biodistribution and tumor targeting will be studied. Specifically, after irradiation, tumor bearing mice will be used to systematically study the in vivo pharmacokinetics of $^{111}$In labeled peptide in both low and high (10-fold) specific activities at multiple time points (1 h, 4 h, 24 h, and 48 h post tracer intravenous (i.v.) injection, n=4/group). A control DPTA-PEG-scrambled peptide will also be used for biodistribution studies to evaluate non-specific tumor retention.

For biodistribution studies, animals will be sacrificed at each time point and the organs of interest will be collected, weighed, and counted in a well gamma counter. The in vivo stability, elimination rate and route of $^{111}$In-PEG-peptide will be evaluated through metabolism studies. Specifically, after i.v. administration, approximately 100 μL of mouse blood will be collected at each time point and separated into supernatant and cell pellet via centrifugation. Each fraction will be counted in a gamma counter. The supernatant will be analyzed with fast protein liquid chromatography (FPLC) equipped with radioactivity detectors. The identification of $^{111}$In-peptide will be confirmed with purified $^{111}$In-peptide standard. The molecular weight of any other radioactive species during the separation will be calculated via the calibration curve for further identification. Additionally, urine and feces samples will be collected to measure the clearance of $^{111}$In-peptide in a longitudinal setting up to 2 weeks. These studies will give specific and sensitive organ uptake statistics and provide fundamental insight into the pharmacokinetics, specific binding of $^{111}$In-peptide to GRP78 and how the specific activity affects the tumor retention in vivo. It is anticipated that the pharmacokinetic evaluation of $^{111}$In-peptide with different specific activities will lead to optimal biodistribution profile and tumor SPECT imaging contrast ratio.

$^{111}$In-Peptide SPECT Imaging. Based on the optimized time point and specific activity of $^{111}$In-peptide for tumor targeting obtained from the biodistribution studies, SPECT imaging in tumor bearing mice will be performed to evaluate the inducible receptor targeting specificity and efficiency. Following the same irradiation dose, SPECT imaging studies will be carried out to assess the temporal and spatial expression of inducible receptor from day 1 to day 3 on the same animal. Further, the correlation between the irradiation dose and receptor expression level measured by SPECT imaging will also be investigated at the optimized time point to enhance the understanding of $^{111}$In-peptide imaging efficiency. Specifically, 100 μCi of $^{111}$In-peptide will be injected via tail vein. At the optimized time point, mice will be scanned on the nanoSPECT scanner. The Inveon CT will be used to collect anatomic information for co-registration with SPECT. The SPECT images will be reconstructed with the maximum a posteriori algorithm and analyzed by ASIPro or IRW. For each SPECT image, a region of interest (ROI) will be drawn on multiple slices of tumors. The variation of tumor SPECT imaging studies will be correlated with the histopathological examination of the receptor expression level. Besides using control PEG-peptide to assess non-specific tumor retention, competitive SPECT blocking studies will be carried out to confirm the targeting specificity via the co-administration of non-radiolabeled peptide with 100:1 molar ratio to the $^{111}$In-peptide. It is anticipated that the $^{111}$In-peptide with optimized specific activity will afford sensitive and specific SPECT detection of the inducible receptor in the tumor with enhanced contrast ratio. Importantly, the non-invasive, quantitative measurement will provide a functional evaluation of the temporal and spatial distribution of the PEG-peptide at multiple time points.

$^{111}$In-Peptide Percent Specific Binding. The experimental procedure will be performed in two steps. In a first step, animal studies will be conducted to establish biodistribution in vivo, to determine the toxicity and to calculate the human radiation dose estimates in animals prior to the second step which will consist of imaging mice with $^{111}$In labeled peptide. The results of the animals study will help predict the human biodistribution and will provide guidelines for safe administration of the radiopharmaceutical in humans. The animal dosimetry experiment will provide the nominal radiation dose estimates which allow determination of the amount of radioactivity that will be injected in the human imaging studies.

Biodistribution Study in Mice: Animal biodistribution will be determined by the standard animal dissection technique. Radiolabeled peptide will be injected intravenously via the tail-vein. At several time points after the tracer injection (such as 30 min, 1 hr, 4 hr, 8 hr, 24 hr and 48 hr) (with n>=5 per time point), the animals will be sacrificed and dissected. All major organs will be weighed and counted for radioactivity in a Gamma Counter. Blood and sample tissues will be removed, blotted dry, and counted. Biodistribution data will be calculated and reported as % ID/g (mean±SD) and % ID (mean±SD) for each organ, decay corrected to the time of injection. To account for the relative organ weight in mice with respect to human, organ % ID will be scaled by the ratio of relative human organ weights to the mouse organ weights with respect to the body weight of mice.

Time activity curves will be created by combining the % ID for each organ and each animal group and uptake-clearance function will be fitted to those by the least square technique. The choice of the fitting function will be determined to achieve a best fit to the data. The typical formulation of the function is usually a combination of exponentials. Animals will be kept in metabolic cages in order to determine the amount of activity that will be excreted either in urine or feces, although limited activity is expected to be excreted due to the slow metabolism of antibodies. Residence times will be calculated by analytical integration of the fitted time taking into account the radioactive decay of $^{111}$I. Residence times will be expressed in hr and normalized to one unit injected activity. All non-accounted activity as well as activity in the blood and fat will be assigned to the remainder of the body. The red marrow residence time will be assessed from the blood residence time by the relation.

$$A_{RM} = \frac{RMECF}{(1-HCT)} A_{BL} \times \frac{M_{RM\_patient}}{M_{BL\_patient}} \quad (I)$$

Where RMECFF is the Red Marrow Extra Cellular Fraction (with nominal value of 0.19) and HCT is the blood hematocrit value (nominally of value 0.39), and where $A_{BL}$ and $A_{RM}$ are respectively the blood and red marrow residence time. $M_{RM}$ and $M_{BL}$ are respectively the mass of red marrow and blood. The scale factor of $M_{RM}$ represents the approximate specific activity of labeled antibodies bound to the surface of the marrow cells.

If $^{111}$In-DPTA-PEG-GIRLRG (SEQ ID NO:1) loses cancer specificity in this study, then the use of other chelators for $^{89}$Zr (DFO) and $^{64}$Cu (DOTA) will be studied. These chelators can label with less stringent conditions. If DPTA-PEG-GIRLRG (SEQ ID NO:1) shows cancer selective binding, then $^{90}$Y will be studied to determine tumor growth delay and tumor control.

Example 3: Conjugation of Peptides to Drug Delivery Systems and Internal Emitters for Imaging of Biodistribution Concomitant chemotherapy and radiation therapy is the standard of care in patients with stage III non-small cell lung cancer (NSCLC). The goal of the present disclosure is to use the PEGylated peptide for guided drug delivery by use of bifunctional PEG on nanoparticles (Hariri, 2010) or in liposomes (Lowery, 2010), including thermal regulated drug delivery. This may involve the design of conjugation systems such as peptide or PEG linkers to nanoparticles and liposomes that will be radiolabeled for imaging in clinical. Mouse models of human cancer will be studied (Passarella, 2010; Hariri, 2010; Lowery, 2010).

The drug delivery systems that may be used include: nanoparticle albumin Taxol (nab; Abraxane) and doxorubicin in liposomes (Doxil) (Passarella, 2010; Lowery, 2010). GIRLRG (SEQ ID NO:1)-nab and GIRLRG (SEQ ID NO:1)-Doxil improve cancer specificity of drug delivery and improve tumor control relative to non-targeted Abraxane with radiotherapy (FIG. 4). In this Example, cancer specificity of drug delivery by the lead PEG-peptide conjugate (from Example 2) will be compared to that of the control peptide. The experimental groups will include untreated control, radiation alone, GIRLRG (SEQ ID NO:1)-Doxil, GIRLRG (SEQ ID NO:1)-Doxil+radiation, control peptide-Doxil, control peptide-Doxil+radiation, Doxil+radiation (Table 1). The assays that will be used to compare these groups include imaging biodistribution (Hariri 2010; Lowery, 2011), drug levels in tumor and normal tissues (Lowery, 2011), and tumor growth delay in treated tumors (Hariri, 2010; Passarella 2010) (Table 1). Size, aggregation and surface charge for conjugates will also be characterized.

The goal of the proposed preclinical studies is to determine the efficacy of the GIRLRG ligand conjugated to liposomal doxorubicin by use of PEG. Efficacy in human lung cancer tumors in nude mice will be studied. Preparation and drug-loading of the liposomes will be carried out as described (Lowery, 2011). Briefly, liposomes will be made with cholesterol and 1,2-Distearoyl-sn-Glycero-3-Phosphocholine (DSPC) at a molar ratio of cholesterol:DSPC=45:55. PEG-GIRLRG (SEQ ID NO:1) will be obtained from Bachem. Maleimide-PEG-DSPE (1,2-Distearoyl-sn-Glycero-3-Phosphoethanolamine-N-[Maleimide(Polyethylene Glycol) will be included in liposomes (2% of total phospholipids for each). Lipids will be dissolved in chloroform (10 mg/ml) and mixed in a round bottom flask attached to a rotary evaporator. A thin lipid film formed after the chloroform will be evaporated under vacuum. The lipid film will be rehydrated in 500 mM of ammonium sulfate with 2 mM of desferrioxamine mesylate (pH 5.5) at 45° C. Liposomes will be subsequently extruded repeatedly through polycarbonate membrane filters with a pore size of 100 nm. Desalting columns will be utilized to change buffers and remove the unconjugated free peptide or dye from the liposomes. The final concentration of liposomes will be adjusted to 1 mg/ml. Loading of doxorubicin will be driven by the pH gradient generated from the ammonium sulfate within the liposomes. Doxorubicin (from Sigma, 2 mg/ml in PBS) will be mixed with the liposome suspension and maintained at room temperature for 2 h. Free drug will be removed by passing the liposome suspension through a desalting column. The drug concentration will be determined with a fluorophotometer (excitation/emission at 480/550 nm).

TABLE 1

| Experimental Groups | Analyses |
| --- | --- |
| untreated control | Tumor growth delay |
| radiation alone | Tumor control |
| GIRLRG-Doxil | Tumor biodistribution |
| GIRLRG-Doxil + radiation | Drug levels in tumor & blood |
| control peptide-Doxil | |
| control peptide-Doxil + radiation | |
| Doxil + radiation | |

GIRLRG (SEQ ID NO:1)-Doxil+radiation will be compared to each of the control groups to measure improved doxorubicin delivery to cancer and improved tumor control. Standard ANOVA methods will be used to analyze the effect of the various experimental groups given above to test for significant differences among treatment groups. Dunnett's and Tukey's tests will be used to compare the treatments with the control and each other. Unpaired t-tests will be used to analyze the effect of radiation by comparing the irradiated tumors against the non-irradiated with the same peptide. Non-parametric analysis will utilize Kruskal-Wallace assessment.

Tumor growth delay will be performed as described (Hallahan, 2003; Hariri, 2010; Passarella, 2010). Briefly, Mice will be monitored daily and tumor volume will be measured manually with a caliper, using the formula: volume=length×width×height/2, derived from the formula for an ellipsoid. When tumors had reached the desired size (5-6 mm diameter), the mice will be grouped (n=8) and injected i.v. with treatment groups listed above. Tumors will be treated with radiation (3Gy×3). Tumor control analysis will be performed as described (Hallahan, 2003; Hariri, 2010; Passarella, 2010). Data will be calculated as fold increase from the original tumor volume, with variance analyzed by the Kruskal-Wallis method.

Drug levels in tumor and blood will be performed as described (Hariri, 2010; Lowery, 2011). Briefly, doxorubicin within the plasma and tumors will be extracted and quantified by fluorophotometer measurements. Each measurement will be normalized with the weight of the tissue. The half life of doxorubicin within the serum will be calculated by plotting the concentration of the drug within the plasma against the time post drug administration. A ratio of doxorubicin distribution within the tumors and serum will be calculated to determine the efficiency of the drug delivery.

It is expected that peptide will improve tumor growth delay and tumor control in mouse models of cancer. As such, this peptide conjugate will be developed for clinical studies.

REFERENCES FOR EXAMPLES 1-3

1. Kruskal W H, Wallis W A. Use of ranks in one-criteria variance analysis. J Am Stat Assoc 1952; 47:583-621.

2. Hariri, G., et al., *Radiation-guided drug delivery to mouse models of lung cancer.* Clin Cancer Res, 2010. 16(20): p. 4968-77.
3. Lowery, A., et al., *Tumor-targeted delivery of liposome-encapsulated doxorubicin by use of a peptide that selectively binds to irradiated tumors.* J Control Release, 2010. 150(1): p. 117-24.
4. Passarella, R. J., et al., *Targeted nanoparticles that deliver a sustained, specific release of Paclitaxel to irradiated tumors.* Cancer Res, 2010. 70(11): p. 4550-9.
5. Han, Z., et al., *Noninvasive assessment of cancer response to therapy.* Nat Med, 2008. 14(3): p. 343-9.
6. Wang, H., et al., *TIP-1 translocation onto the cell plasma membrane is a molecular biomarker of tumor response to ionizing radiation.* PLoS One, 2010. 5(8): p. e12051.
7. Lee, A. S., *GRP78 induction in cancer: therapeutic and prognostic implications.* Cancer Res, 2007. 67(8): p. 3496-9.
8. Arap, M. A.; Landenranta, J.; Mintz, P. J.; Hajitou, A.; Sarkis, A. S.; Arap, W.; Pasqualini, R. Cell surface expression of the stress response chaperone GRP78 enables tumor targeting by circulating ligands. *Cancer Cell,* 2004, 6, 275-284.
9. Hallahan D E, Geng L, Qu S, et al. Integrin-mediated targeting of drug delivery to irradiated tumor blood vessels. Cancer Cell 2003; 3:63-74.
10. Hariri G, Zhang Y, Fu A, et al. Radiation-guided P-selectin antibody targeted to cancer. Annals of Biomedical Engineering 2008; 36:821-830.
11. Hallahan D. E., Geng L., Cmelak A. J., Chakravarthy A. B., Martin W Scarfone C., Gonzalez A. Targeting drug delivery to radiation-induced neoantigens in tumor microvasculature. Journal of Controlled Release 74:183-191, 2001
12. Sengupta, S.; Eavarone, D.; Capila, I.; Zhao, G. L.; Watson, N.; Kiziltepe, T.; Sasisekharan, R. Temporal targeting of tumour cells and neovasculature with a nanoscale delivery system. *Nat. Let.,* 2005, 436, 568-72.
13. Karmali, P. P.; Kotamraju, V.; Kastantin, M.; Black, M.; Missirlis, D.; Tirrell, M.; Ruoslahti, E. Targeting of albumin-embedded paclitaxel nanoparticles to tumors. *Nanomed. Nanotechnol.* 2009, 5, 73-82.
14. Palama, I. E.; Leporatti, S.; de Luca, E.; Di Renzo, N.; Maffia, M.; Gambacorti-Passerini, C.; Rinaldi, R.; Gigli, G.; Cingolani, R.; Coluccia, A. M. Imatinib-loaded polyelectrolyte microcapsules for sustained targeting of BCR-ABL+leukemia stem cells. *Nanomedicine-UK,* 2010, 5(3), 419-431.
15. Lowery, A.; Onishko, H.; Hallahan, D. E.; Han, Z. Tumor-targeted delivery of liposome-encapsulated doxorubicin by use of a peptide that selectively binds to irradiated tumors. *J. Control. Release,* 2011, 150(1), 117-124.
16. U.S. Cancer Statistics Working Group. United States Cancer Statistics: 1999-2007 Incidence and Mortality Web-based Report. Atlanta (Ga.): Department of Health and Human Services, Centers for Disease Control and Prevention, and National Cancer Institute; 2010.
17. Sun, q., *GRP78 in NSCL cancer.* Mol Biol Rep, 2012. epub ahead of print.
18. Munro, S. and H. R. Pelham, *A C-terminal signal prevents secretion of luminal ER proteins.* Cell, 1987. 48(5): p. 899-907.
19. Burikhanov, R., et al., *The tumor suppressor Par-4 activates an extrinsic pathway for apoptosis.* Cell, 2009. 138(2): p. 377-88.
20. Davidson, D. J., et al., *Kringle 5 of human plasminogen induces apoptosis of endothelial and tumor cells through surface-expressed glucose-regulated protein 78.* Cancer Res, 2005. 65(11): p. 4663-72.
21. Philippova, M., et al., *Identification of proteins associating with glycosylphosphatidylinositol-anchored T-cadherin on the surface of vascular endothelial cells: role for Grp78/BiP in T-cadherin-dependent cell survival.* Mol Cell Biol, 2008. 28(12): p. 4004-17.
22. Kern, J., et al., *GRP-78 secreted by tumor cells blocks the antiangiogenic activity of bortezomib.* Blood, 2009. 114(18): p. 3960-7.
23. Li, J. and A. S. Lee, *Stress induction of GRP78/BiP and its role in cancer.* Curr Mol Med, 2006. 6(1): p. 45-54.
24. McFarland, B. C., et al., *Plasminogen kringle 5 induces apoptosis of brain microvessel endothelial cells: sensitization by radiation and requirement for GRP78 and LRP1.* Cancer Res, 2009. 69(13): p. 5537-45.
25. Katanasaka, Y., et al., *Cancer antineovascular therapy with liposome drug delivery systems targeted to BiP/GRP78.* Int J Cancer, 2010. 127(11): p. 2685-98.
26. Pyrko, P., et al., *The unfolded protein response regulator GRP78/BiP as a novel target for increasing chemosensitivity in malignant gliomas.* Cancer Res, 2007. 67(20): p. 9809-16.
27. Cohen, M. and P. Petignat, *Purified autoantibodies against glucose-regulated protein 78 (GRP78) promote apoptosis and decrease invasiveness of ovarian cancer cells.* Cancer Lett, 2011. 309(1): p. 104-9.
28. Misra, U. K., et al., *Ligation of cancer cell surface GRP78 with antibodies directed against its COOH-terminal domain up-regulates p53 activity and promotes apoptosis.* Mol Cancer Ther, 2009. 8(5): p. 1350-62.
29. Eberhardt, W. E. E. and et al, eds. *Stage IIIB Non-Small Cell Lung Cancer, in principles and Practice of Lung Cancer.* Lung Cancer, ed. H. Pass and et al. Vol. 1. 2010, Lippincott: Philadelphia. 821-836.
30. Johnson, D., et al., eds. *Cancer of the lung. Abeloff's Clinical Oncology,* ed. e. a. Abeloff. 2008.
31. Moretti, L., S. Ocak, and D. E. Hallahan, eds. *Cell Cycle and Vascular Targets for Radiotherapy,. principles and practice of lung cancer,* ed. H. Pass. Vol. 1. 2010, Lippincott: Philadelphia. 189-208.

Introduction for the Examples 4-8

Cancer is one of the leading causes of morbidity and mortality worldwide. Cancer treatments require precise spatial identification to locate the tumor. Molecular imaging using single-photon emission computed tomography (SPECT) or positron emission tomography (PET) offers tremendous advantage in biodistribution of cancer therapeutic agents [1]. Several radiolabeled targeting agents, including small molecules, peptides, proteins as well as antibodies and antibody fragments, have been utilized in non-invasive imaging and detection of tumors. Molecular imaging using radiolabeled-peptides offer several advantages over traditional imaging. Targeting peptides are relatively small in size, allowing enhanced diffusion properties, target accessibility and high sensitivity. Additionally, peptides have little antigenicity and are economical to synthesize. Peptides exhibit metabolic stability and tolerance to changes in their structures which is common during the radiolabeling process [2]. Despite significant advances, there are few radiolabeled peptide-based tracers that have been approved for clinical use [2]. There are several factors impeding the development of newer agents, including effectiveness, specificity, translational ability, regulatory hurdles. There is a need for developing novel cancer-specific targets and their peptide ligands, which could be developed as tracers for noninvasive imaging of cancers.

We developed and characterized a novel peptide, GIRLRG (SEQ ID NO:1) that binds specifically to tumors ex vivo and in vivo [3]. We have also found that GIRLRG (SEQ ID NO:1) conjugated to paclitaxel-encapsulated nanoparticles specifically targeted breast cancer (MDA-MB-231) and glioblastoma (GL261) [3]. We further identified that GIRLRG (SEQ ID NO:1) specifically binds to Glucose-regulated protein 78 kDa (GRP78) [3]. GRP78 is an endoplasmic reticulum (ER) chaperone and is a marker for ER stress. It is induced in various cancers during glucose deprivation, hypoxia and acidosis in the microenvironment of poorly vascularized tumors [4]. ER stress leads to induction of GRP78 in the ER compartment, as well relocalization from the ER to the cell surface [5]. Cell-surface GRP78 is detected on many types of cancer cells in vivo [6, 7] and is not present on noncancerous cells [4, 8-10]. Expression of GRP78 on the surface of human cancer cells is associated with tumorgenesis, tumor progression, angiogenesis, and metastasis, thereby demonstrating its utility as an anticancer therapeutic target [4].

We have identified the binding site and affinity of GIRLRG (SEQ ID NO:1) peptide to GRP78. Using heterotopic tumor models in mice we found that GIRLRG (SEQ ID NO:1) peptide specifically binds to tumors and can be developed as therapeutic agent for various cancers.

Example 4: GIRLRG (SEQ ID NO:1) Binds to the ATPase Domain of the GRP78 Protein

Figure 5A:
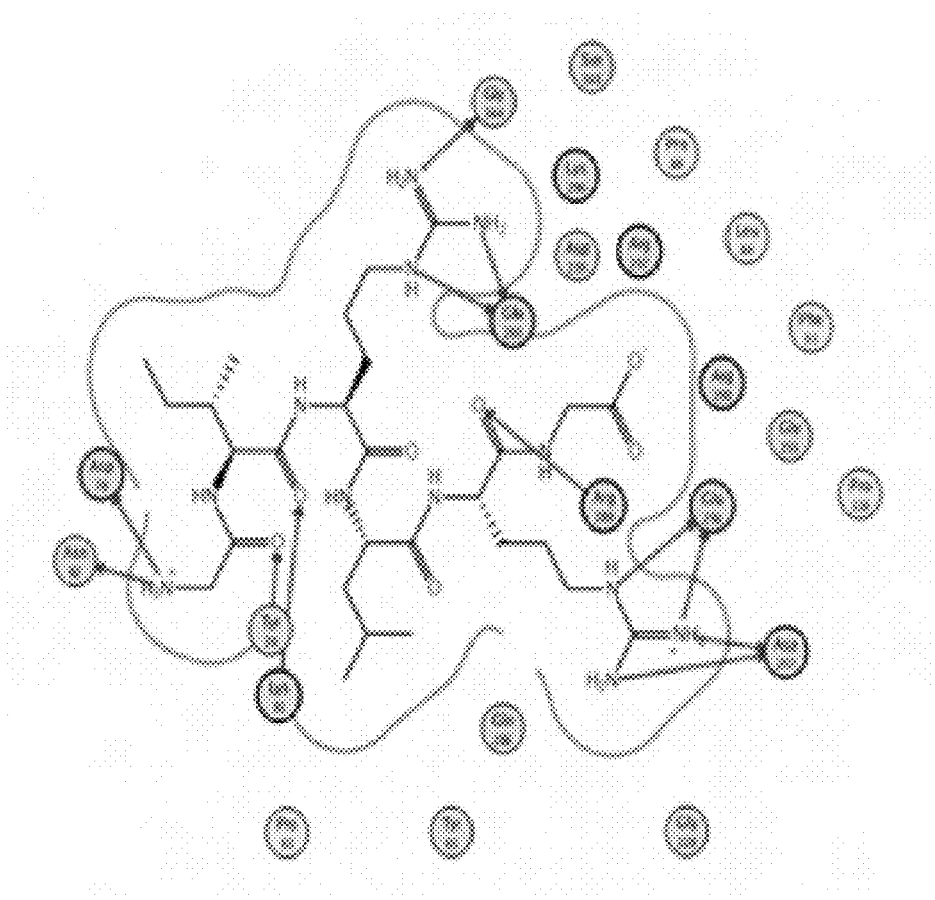
FIG. 5A-C depicts modeling of GIRLRG (SEQ ID NO:1) peptide into the GRP78 ATPase domain.
Figure 5B:
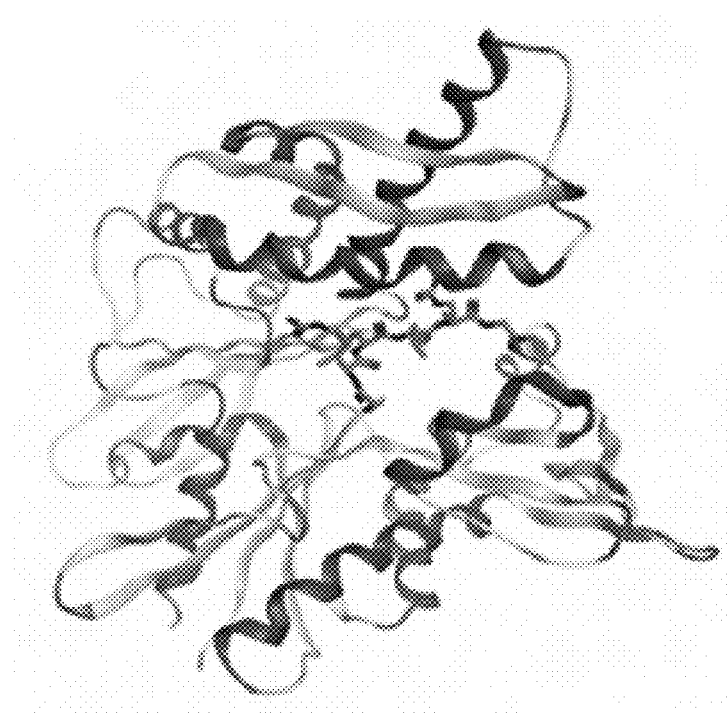
Figure 5C:
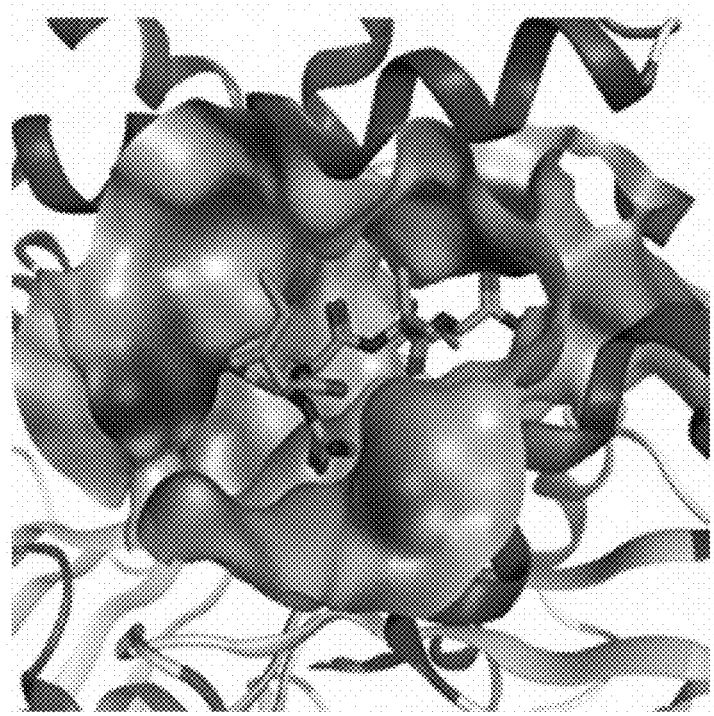

The GIRLRG (SEQ ID NO:1) peptide was modeled with the GRP78 which shows the binding sites and the interacting residues in the ATPase domain of the GRP78 protein (FIG. 5). In this model, two of the peptide's Arg fit on either side of the main central helix in GRP78 and are surrounded by charged residues (FIG. 5A and FIG. 5B). The first Arg interacts strongly with Asp 259 and Glu 293, forming a charge network also with Lys 296 and Arg 297 (FIG. 5B and FIG. 5C). The second peptide Arg is flanked by Glu 256 and A257. A complete list of interacting residues is shown in

TABLE 2

Table 2. Complete list of GRP78 ATPase domain residues that interact with GIRLRG (SEQ ID NO: 1)

| |
| --- |
| Thr 38 |
| Tyr 39 |
| Pro 63 |
| Tyr 65 |
| Asp 78 |
| Lys 81 |
| Asn 82 |
| Leu 84 |
| Phe 93 |
| Glu 256 |
| Asp 257 |
| Asp 259 |
| Arg 289 |
| Arg 290 |
| Lys 294 |
| Lys 296 |
| Arg 297 |

Example 5: GIRLRG (SEQ ID NO:1) Peptide Binds Specifically to GRP78 Protein

Figure 6A:
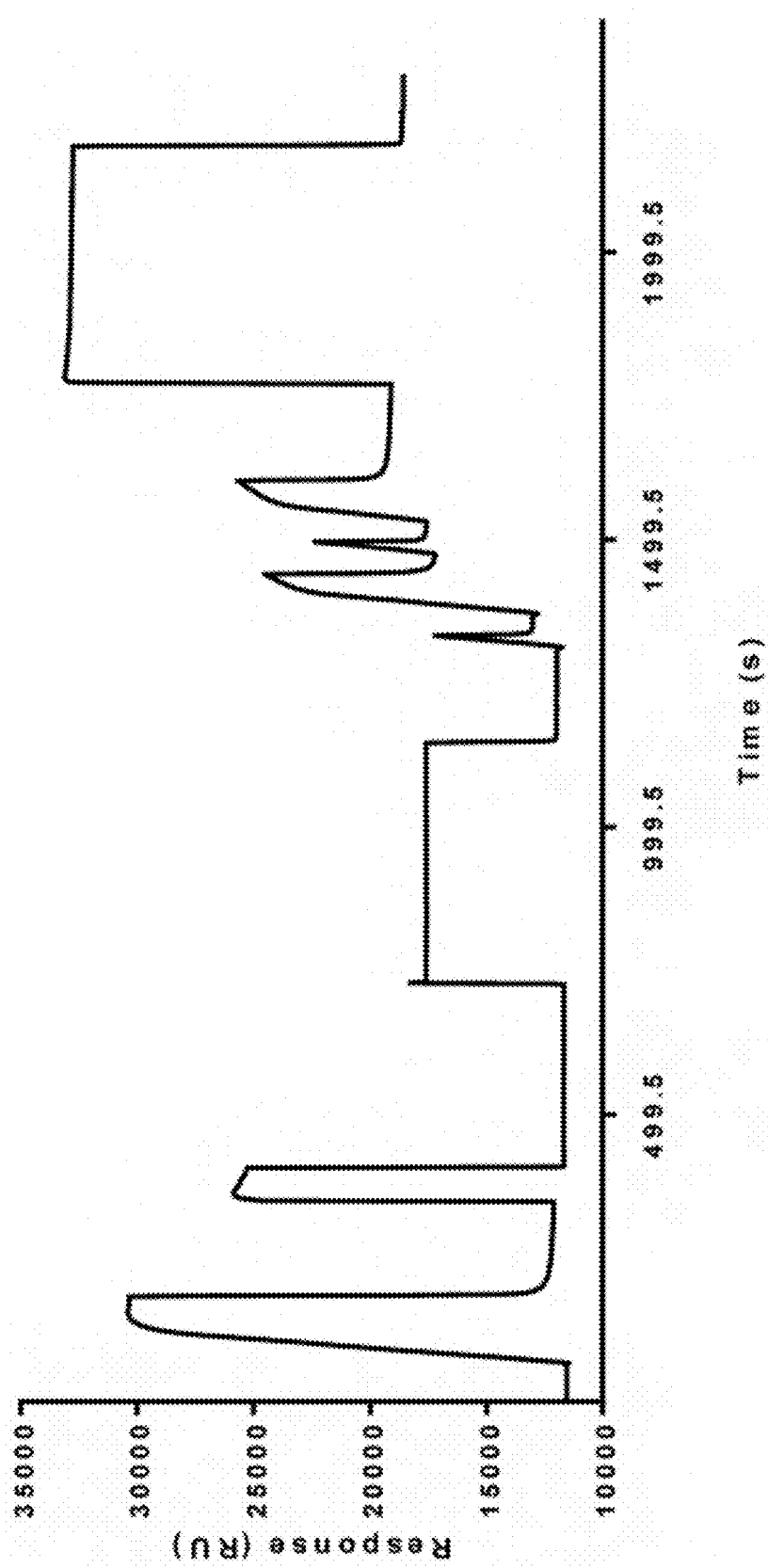
FIG. 6A-B depicts binding affinity of GIRLRG (SEQ ID NO:1) peptide to GRP78 protein using surface plasmon resonance.
Figure 6B:
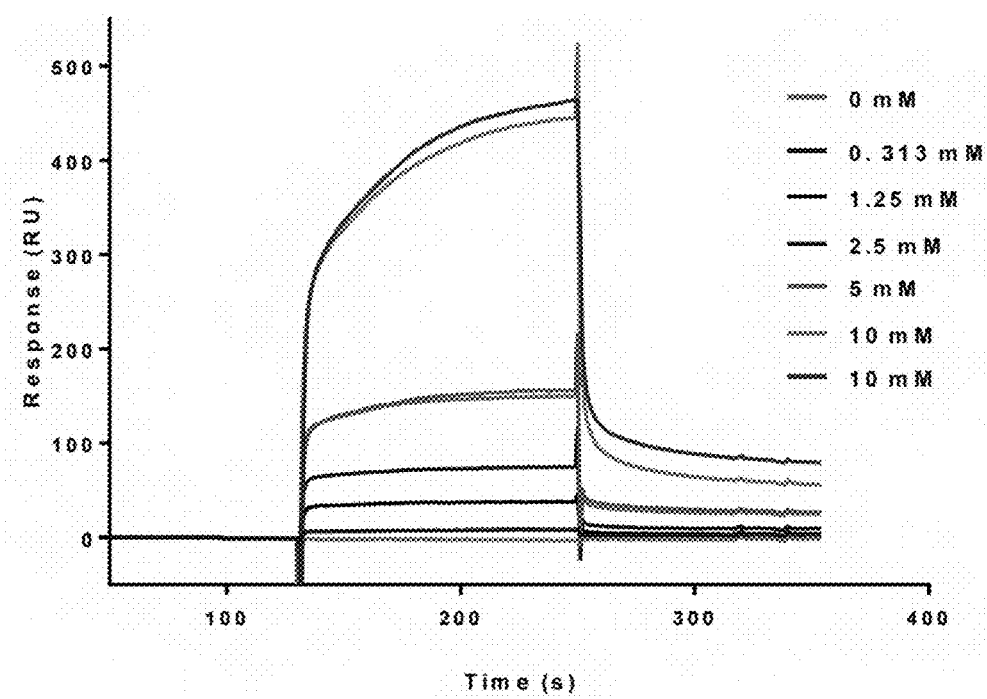
Figure 7A:
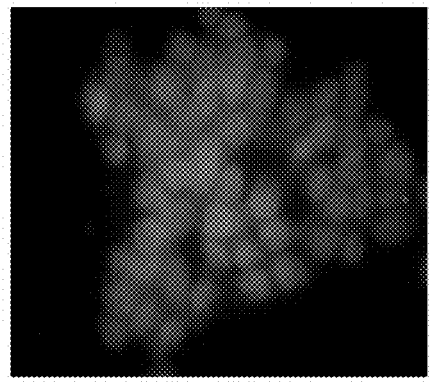
FIG. 7A-D depicts binding of FITC-conjugated GIRLRG (SEQ ID NO:1) peptide to cancer cell lines as observed under fluorescent microscope (Resolution 200x).
Figure 7B:
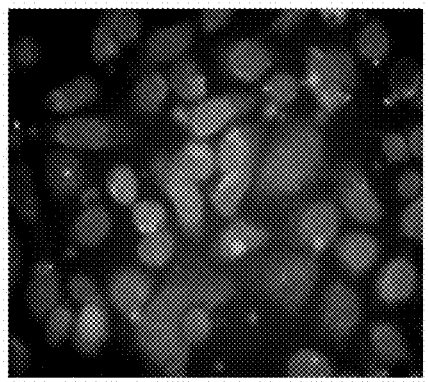
Figure 7C:
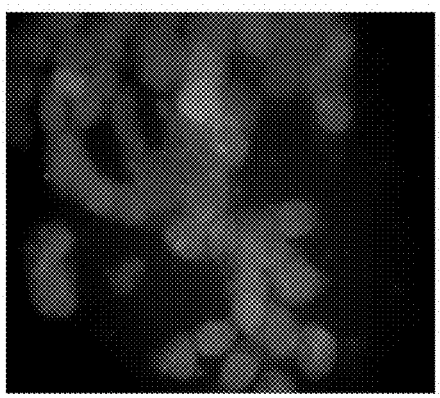
Figure 7D:
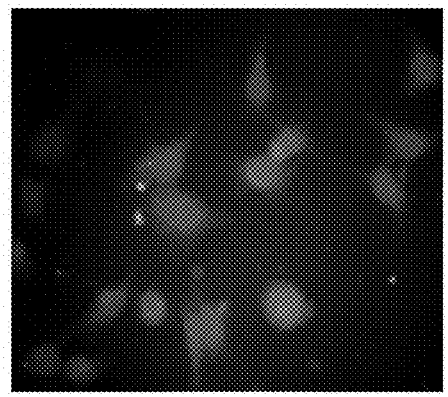

To determine the binding affinity of GIRLRG (SEQ ID NO:1) peptide to GRP78 protein, we used surface plasmon resonance technology. GRP78 protein was immobilized on the surface of CM4 sensor chip and approximately 7000 resonance Units (RUs) of GRP78 protein were immobilized (FIG. 6A). The GIRLRG (SEQ ID NO:1) peptide was dissolved in HBS-EP buffer at various concentrations (10, 5, 2.5, 1.25 and 0.313 mM) and passed over the immobilized GRP78 for 2 min (FIG. 6B). The rate constant $K_D$ was obtained by fitting the sensogram data after reference subtraction (data from blank channel) using the BIA evaluation 3.0 software. The change in RU with varying concentrations of peptide indicated the change in bound mass on sensor surface with time and the dissociation constant was found to be $2.16e^{-3}M$.

Example 6: GIRLRG (SEQ ID NO:1) Peptide Binds to Cancer Cells In Vitro.

Four cancer cell lines D54 (glioma), HT3 (cervical), OE33 (eosophageal) and A549 (lung cancer) were used to evaluate binding of GIRLRG (SEQ ID NO:1) peptide. Cancer cells were incubated with FITC-conjugated GIRLRG (SEQ ID NO:1) peptide and fluorescent images were acquired using a fluorescent microscope. FITC labeled GIRLRG (SEQ ID NO:1) peptide showed binding to D54, HT3, OE33 and A549 cell lines (FIG. 7).

Example 7: Radiolabelling of PEG Peptides

Figure 11A:
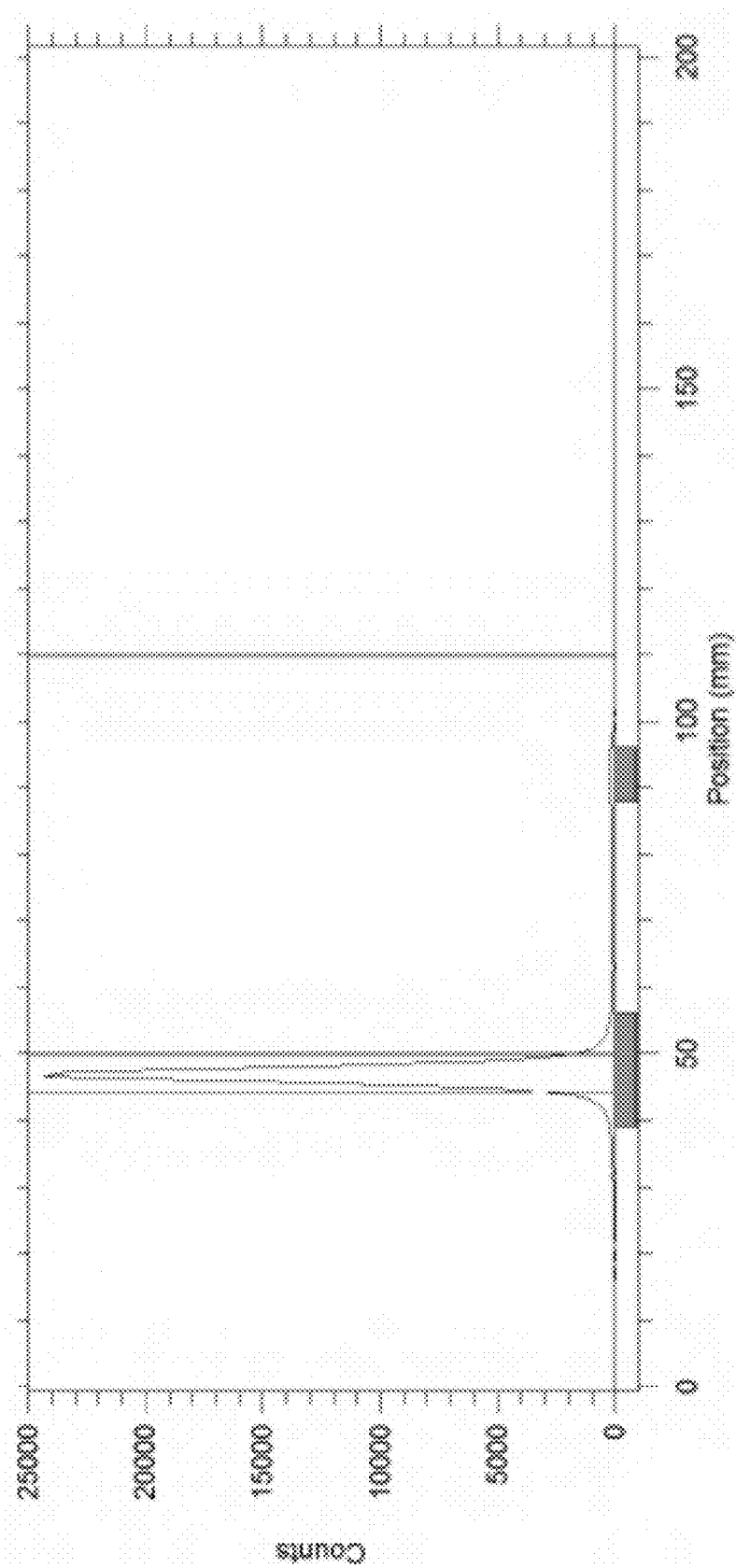
FIG. 11A-B depicts instant thin layer chromatogram of $^{111}$In-DTPA-PEG-control (FIG. 11A) and $^{111}$In-DTPA-PEG-GIRLRG (SEQ ID NO:1) (FIG. 11B). $^{111}$In-DTPA-PEG-GIRLRG (SEQ ID NO:1) stays at the origin and $^{111}$In-DTPA moves with solvent front.
Figure 11B:
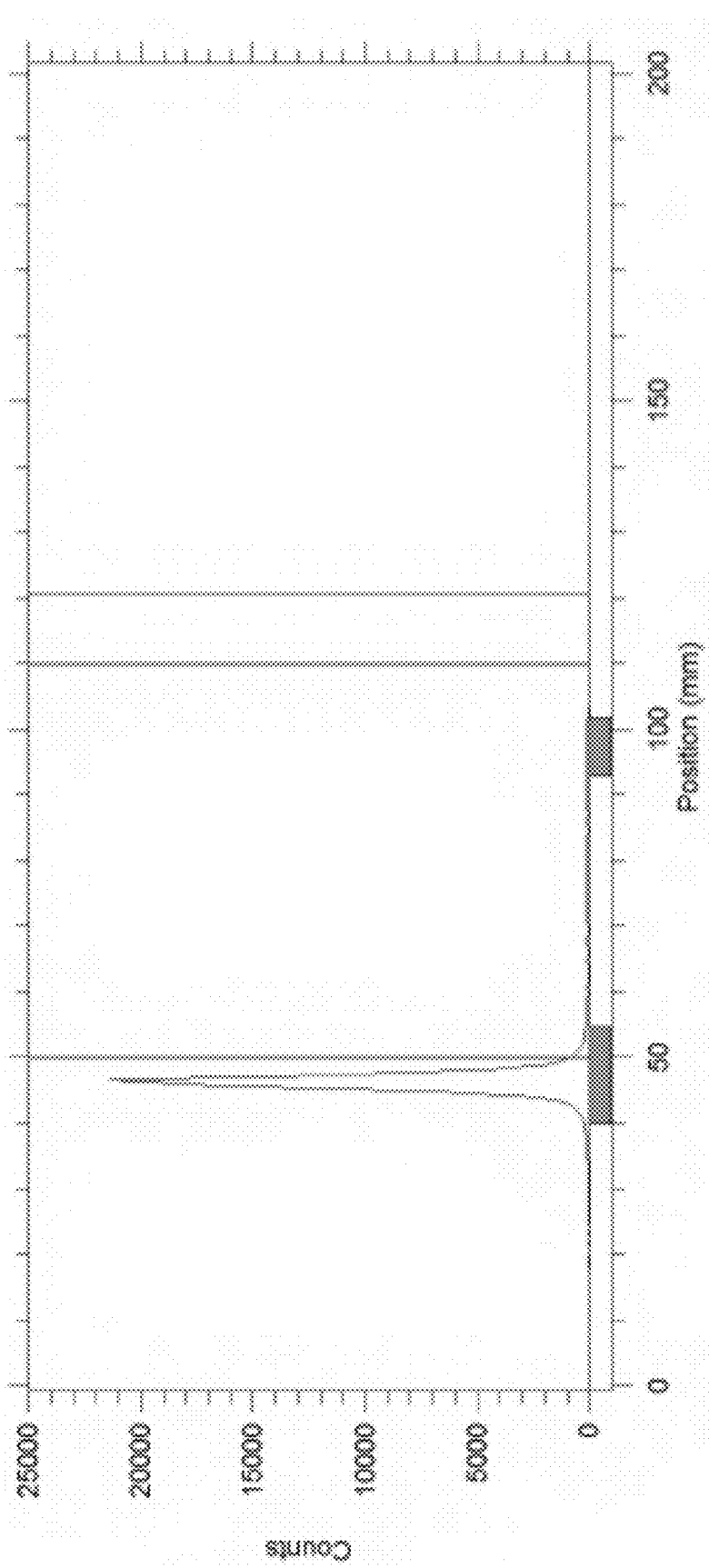

The radiolabeling of PEG peptides was optimized by varying the pH, buffer, temperature and amount of $^{111}InCl_3$ added per mg DTPA-PEG-compounds. For all in vivo studies, DTPA-PEG-control and DTPA-PEG-GIRLRG (SEQ ID NO:1) peptide was labeled with $^{111}$Indium. The best yield was obtained by carrying out all reactions under absolute metal-free condition. The optimal pH was 5.5, the optimal temperature was 95° C. and ammonium acetate buffer resulted in best labeling yield. Dynamic light scattering (DLS) studies were performed with the pegylated peptides to confirm the absence of aggregates or changes in size (data not shown). DTPA-PEG-compounds were radiolabeled with a specific activity of 370MBq (10 mCi) (greater than 95% radiolabeling efficiency) per mg compound. The ITLC chromatogram of $^{111}$In-DTPA-compounds is shown in FIG. 11.

Example 8: GIRLRG (SEQ ID NO:1) Peptide Binds Specifically to Tumors In Vivo

Figure 8A:
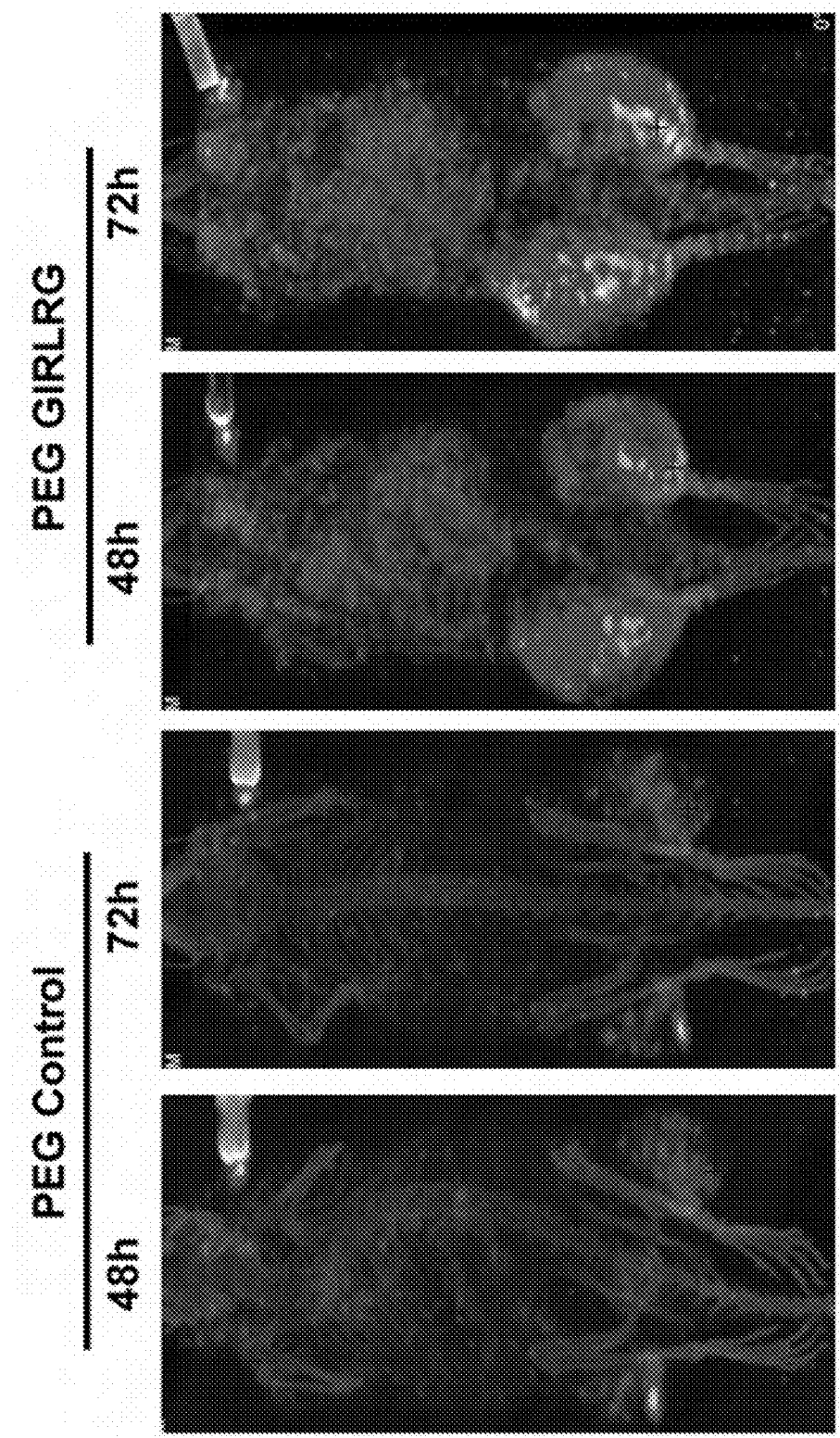
FIG. 8A-B depicts SPECT imaging (FIG. 8A) and post-SPECT biodistribution (FIG. 8B) with radiolabeled PEG-GIRLRG (SEQ ID NO:1) and PEG-control peptide in nude mice with heterotopic cervical tumors (HT3). The tumor on the right hind limb was irradiated with 3 doses of 3 Gy and the left was sham control. Enhanced tumor binding of the PEG-GIRLRG (SEQ ID NO:1) peptide is observed in HT3 tumors at both 48 h and 72 h post injection. ***p<0.001.
Figure 9A:
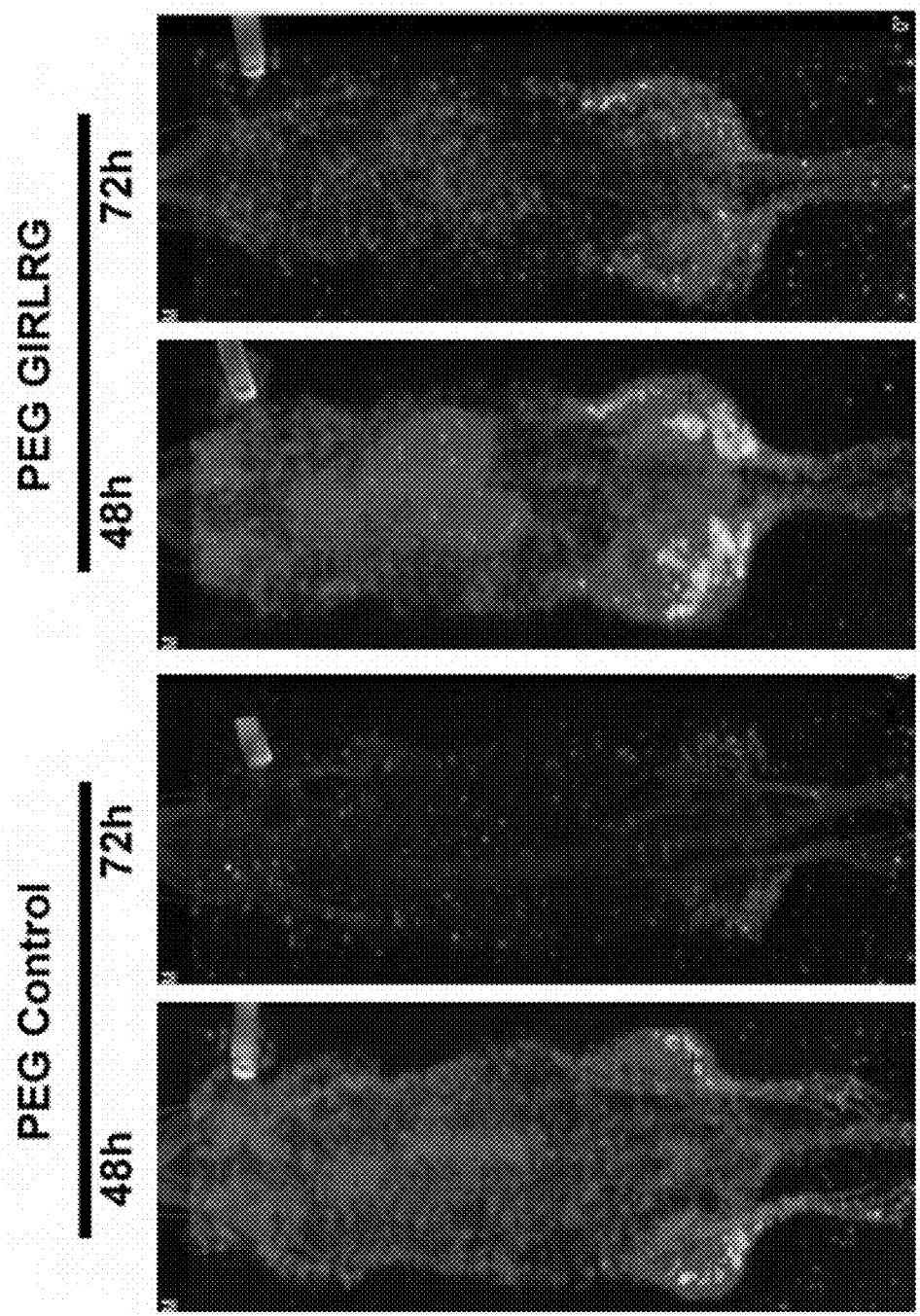
FIG. 9A-B depicts SPECT imaging (FIG. 9A) and post-SPECT biodistribution (FIG. 9B) with radiolabeled PEG-GIRLRG (SEQ ID NO:1) and PEG-control peptide in nude mice with heterotopic esophageal (OE33). The tumor on the right hind limb was irradiated with 3 doses of 3 Gy and the left was sham control. Enhanced tumor binding of the PEG-GIRLRG (SEQ ID NO:1) peptide is observed in HT3 tumors at both 48 h and 72 h post injection. ***p<0.001.

Radiotherapy is routinely used for treating local cancers including cervical and esophageal cancers. To evaluate the efficacy of tumor binding of $^{111}$In-labeled PEG-GIRLRG (SEQ ID NO:1) peptide, we performed imaging in cervical (HT3) and esophageal (OE33) heterotopic tumors using nanoSPECT/CT. Nude mice bearing the HT3 and OE33 tumors in both the hind limbs were used (~1 cm³). Since radiotherapy is used in treating cervical and esophageal cancers, we also irradiated the tumors. The tumor on the right hind limb was irradiated with 3 fractions of 3 Gy over a course of 24 h, the tumor on the left hind limb was used as sham control. The mice were then injected with 500 μCi (10 μCi/μg) of radiolabeled peptide via tail vein. SPECT/CT imaging was performed at 48 and 72 h post injection. The SPECT imaging at 48 h and 72 h post injection revealed that $^{111}$In-labeled PEG-DTPA-GIRLRG (SEQ ID NO:1) peptide bound to HT3 (FIG. 8A) and OE33 (FIG. 9A). Very low or negligible binding of $^{111}$In-labeled PEG-DTPA-control was observed in both HT3 (FIG. 8A) and OE33 (FIG. 9A)

tumors. Irradiating the tumors (right hind limbs) did not affect tumor binding of the radiolabeled GIRLRG (SEQ ID NO:1) peptide.

Figure 8B:
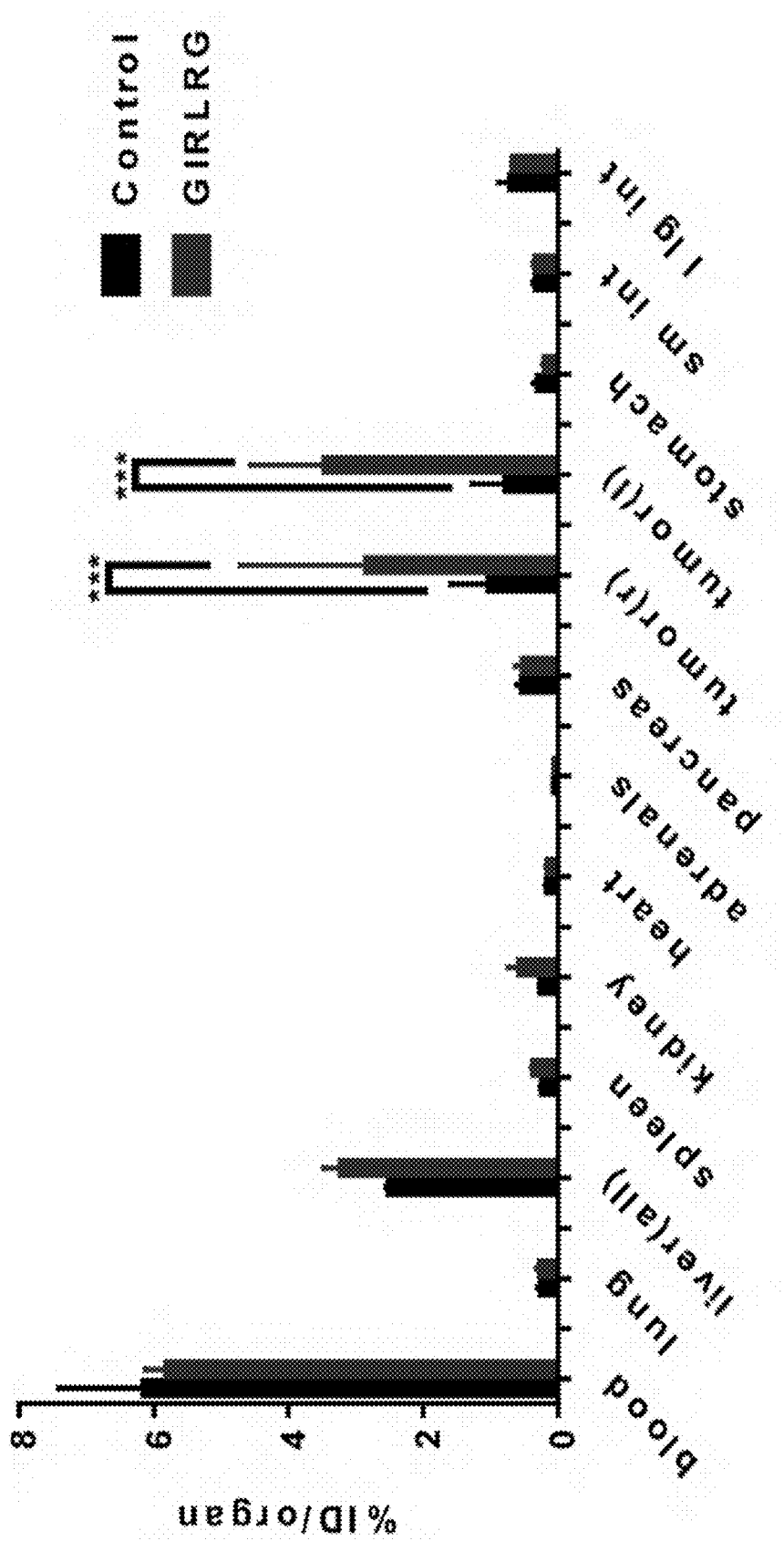
Figure 9B:
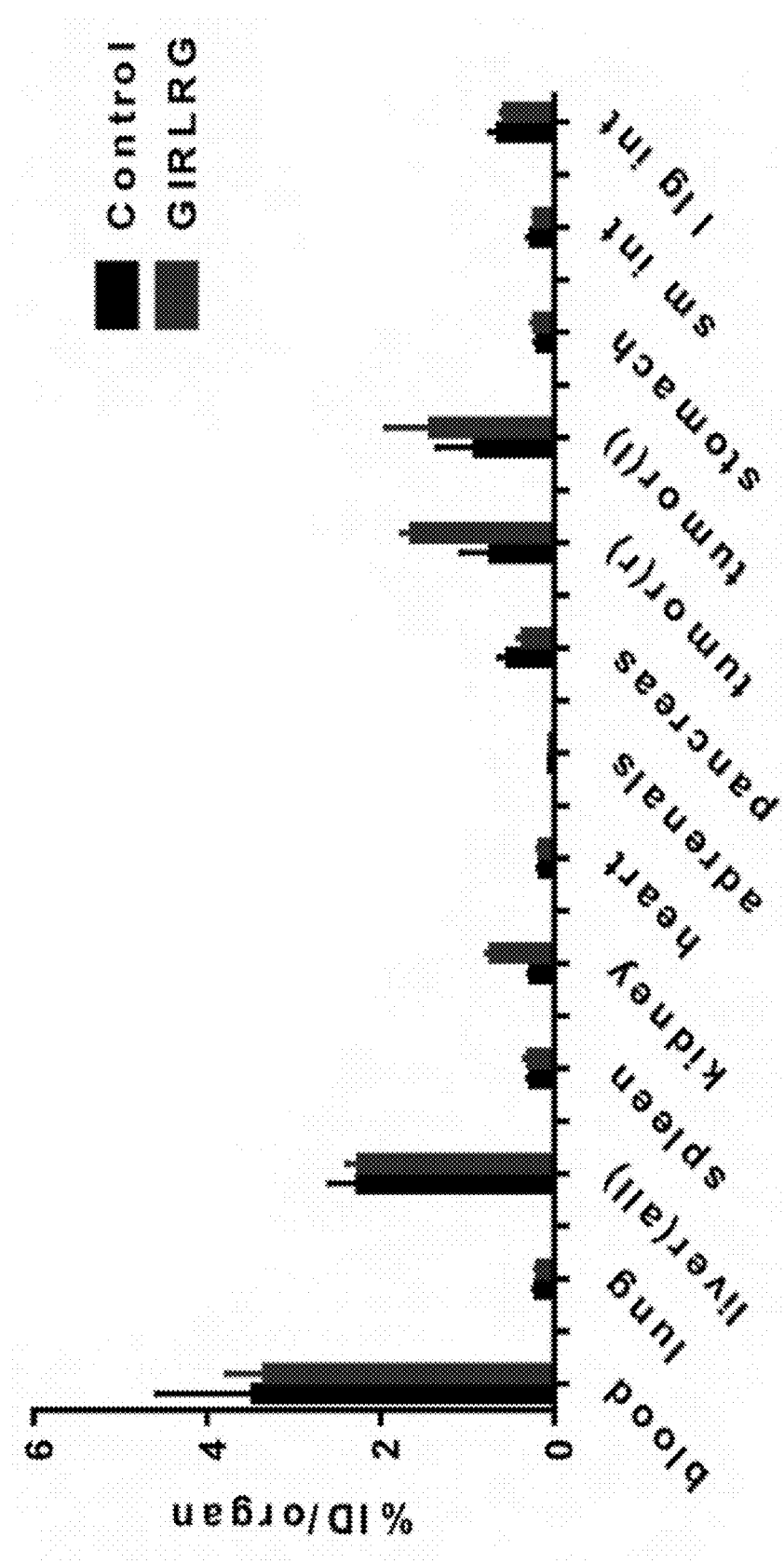

Post-SPECT biodistribution was performed 96 h after injection (FIG. 8 and FIG. 9). The post-SPECT biodistribution data of the $^{111}$In labeled compounds in tumor bearing mice are summarized in FIG. 8B and FIG. 9B. The biodistribution results correlate with the SPECT imaging data. Significantly higher (p<0.001) uptake of the radiolabeled GIRLRG (SEQ ID NO:1) was observed in tumors when compared to control peptide. The radiolabeled peptides were still in circulation as seen from the blood uptake in the biodistribution data. Labeled peptide was also observed in the liver of both HT3 and OE33 tumor bearing mice as these peptides were being cleared from the circulation. Labeled peptide in other organs was negligible.

In addition we also screened lung cancer (A549), pancreatic cancer (BxPC3) and glioblastoma (D54) tumor models for binding of radiolabeled GIRLRG (SEQ ID NO:1) peptide. SPECT/CT imaging showed enhanced binding of $^{111}$In-labeled PEG-DTPA-GIRLRG (SEQ ID NO:1) in A549, BxPC3 and D54 tumors (FIG. 10).

Discussion for Examples 4-8

Peptide receptors are overexpressed in cancers and have been used as molecular targets. Imaging probes currently being developed for these receptors include somatostatin (SST)-analogs, cholecystokinin/gastrin and GLP-1 analogs for neuroendocrine tumors, bombesin and neuropeptide-Y analogs for prostate or breast cancers, and Arg-Gly-Asp peptides for neoangiogenesis labeling [2, 14]. The first and most successful FDA approved peptide-based radiopharmaceutical is the somatostatin analog, $^{111}$In-DTPA-octreotide ($^{111}$In-OctreoScan, $^{111}$In-pente-treotide) [2, 15-17]. It is being used for imaging SST receptor-positive lesions, such as neuroendocrine tumors, mammary cancer and small cell lung cancer [15-17]. The successful clinical application of this radiopharmaceutical raised interest in the development of radiolabeled peptides to target other tumor-related peptide receptor systems.

Increasing evidence suggest glucose-related stress response proteins serve as functional chaperones on surface of cancer cells. These regulate multiple signaling pathways related to apoptosis, immune function and drug resistance. GRP78 is one such surface protein that could be potentially developed for targeted therapy against various cancers. GRP78 plays a vital role in the unfolded protein response (UPR), which regulates survival or death pathways in response to ER stress. GRP78 reestablishes normal function of the cell by translation repression, reduction of intermediate protein aggregates, removal of improperly folded proteins, and regulation of intracellular $Ca^{2+}$[18]. GRP78-targeting peptides conjugated with cytotoxic agents have been shown to specifically bind tumors and induce cytotoxicity [8, 19]. GIRLRG (SEQ ID NO:1) peptide was identified by in vivo biopanning, which specifically bound to GRP78 on the surface of various cancers [3]. In the present study, we sought to identify the exact binding domain of GIRLRG (SEQ ID NO:1) peptide to GRP78 protein. Using molecular modeling and docking studies, we found that the GIRLRG (SEQ ID NO:1) peptide bound to the residues in the ATPase domain of GRP78. Different peptides and antibodies binding to the ATPase and substrate binding domains of GRP78 have been reported [20-23]. Some of these have been shown to positively or negatively regulate the growth promoting effects of GRP78, although their modes of action have not been extensively investigated. We used surface plasmon resonance (SPR) to evaluate the affinity of GIRLRG (SEQ ID NO:1) to GRP78. SPR analysis showed that GIRLRG (SEQ ID NO:1) had a $K_D$ of $2.16e^{-3}$M for GRP78. We believe that this might be helpful in the diffusion of the peptide in the tumor as higher the binding affinity, lower will be the diffusion to the interior of the tumor. This was confirmed using FITC-conjugated GIRLRG (SEQ ID NO:1) peptide that showed that the peptide specifically bound to glioma (D54), cervical (HT3), esophageal (OE33) and lung (A549) cancer cells in vitro.

We evaluated GIRLRG (SEQ ID NO:1) peptide as an imaging probe for various tumors. Peptides are small and could be cleared quickly from the system leading to poor bioavailability in targeted tissues [24]. To overcome this problem, we conjugated the GIRLRG (SEQ ID NO:1) peptide to 40 kDa PEG to enhance its circulation time and extravasation to the tumors. This strategy of PEGylation has been successful used and approved for various biomolecules used in the clinic [25]. PEG-GIRLRG (SEQ ID NO:1) was radiolabeled with $^{111}$Indium by use of DTPA as the chelator. The background signal was evaluated using 40 kDa PEG construct having the chelator DTPA (PEG control). PEG-GIRLRG (SEQ ID NO:1) or PEG-Control was used for imaging of cervical (HT3) and esophageal (OE33) using nano SPECT. PEG-GIRLRG (SEQ ID NO:1) specifically bound to HT3 and OE33 tumors while little or no binding was observed in PEG-Control. This data indicated that PEG-GIRLRG (SEQ ID NO:1) had specific binding to the HT3 and OE33 tumors most likely by binding to the GRP78 on the surface of the tumors. Since radiation is routinely used in treating cervical and esophageal cancers, we compared irradiated tumors to sham irradiated tumors. Irradiation of the tumor did not interfere with specific binding of GIRLRG (SEQ ID NO:1) peptide to the HT3 and OE33 tumors. POST SPECT biodistribution data further supported the imaging data. Significantly higher uptake of PEG-GIRLRG (SEQ ID NO:1) peptide was observed in tumors when compared to the PEG-control. In addition to the cervical and esophageal cancer, we evaluated binding of PEG-GIRLRG (SEQ ID NO:1) in lung cancer (A549), pancreatic cancer (BXPC3) and glioblastoma (D54). Similar to the cervical and esophageal tumors, we found specific binding of PEG-GIRLRG (SEQ ID NO:1) to lung cancer, pancreatic cancer and glioblastoma.

Overall, this study strengthens GRP78 as a peptide receptor and a molecular target for development of diagnostics and therapeutics for various cancers. GIRLRG (SEQ ID NO:1) specifically binds to GRP78 on the surface of cancer cells, and this could be a potential peptide for targeting various cancers like cervical, esophageal, lung, glioma and pancreatic. Presently PEG-GIRLRG (SEQ ID NO:1) is being developed further and being prepared for preclinical efficacy and safety testing before moving it to clinical trials.

Methods for Examples 4-8

Cell Lines: Human lung adenocarcinoma A549 and Human glioblastoma D54 cells were cultured in DMEM/F12, human esophageal carcinoma OE33 cells in RPMI and HT3 cells in IMDM media supplemented with 10% fetal bovine serum, penicillin and streptomycin. They were maintained at 37° C. in a 5% $CO_2$ incubator.

Peptide Synthesis: DTPA-PEG-(KKK)-GIRLRG (SEQ ID NO:1) and DTPA-PEG-(KKK)-control containing 40 kDa PEG were synthesized by Bachem (USA). FITC-GIRLRG (SEQ ID NO:1) was synthesized by China peptides (Shanghai, China) using standard solid-phase Fmoc chemistry. The peptides were purified to a minimum purity of 95% by high-performance liquid chromatography (HPLC) and were isolated by lyophilization.

Molecular Modeling Studies: The GIRLRG (SEQ ID NO:1) peptide was modeled into the GRP78 ATPase domain, starting from the published crystal structure with ADP bound, 3IUC [11]. ADP and associated solvent molecules were removed and the apo structure was minimized using the Amber99 [12] in the Molecular Operating Environment (MOE), Chemical Computing Group Inc. Canada. version 2011.10. software. The GIRLRG (SEQ ID NO:1) peptide was placed manually into the groove between Leu 84 and Arg 289 (residue numbering from 3IUC), with the first Arg placed into the adenosine binding site. The orientation was selected based on the observation that when modifying the sequence of GIRLRG (SEQ ID NO:1), that Arg was consistently required for binding. The resulting binding mode was again minimized with the Amber 99 force field.

Surface Plasmon Resonance (SPR): Affinity of GIRLRG (SEQ ID NO:1) to GRP78 protein was measured by the biosensor-based SPR technique using an automatic apparatus BIAcore 2000 (GE healthcare, Sweden) as described earlier [13]. The recombinant eukaryotic GRP78 protein (Prospec, USA) as ligand that was immobilized by amine coupling on the CM4 sensor surface and GIRLRG (SEQ ID NO:1) peptide was used as the analyte. Experiments were performed at 25° C. in HBS-EP buffer (GE healthcare). GRP78 protein was immobolized using surface preparation wizard for amine coupling. Briefly, equal volume (115 µl) of N-hydroxysuccinimide (NHS, 2.3 mg in 200 µl of water) and N-ethyl-N'-3 (diethylamino propyl) carbodiimide (EDC, 15 mg in 200 µl of water) was mixed, and 75 µl of this solution was injected into the flow cell at the flow rate of 5 µl/min across the CM4 sensor chips to activate the carboxy methylated dextran surface for 15 min. GRP78 protein (50 µg/ml in 10 mM sodium acetate, pH 4.7) was injected at the flow rate of 5 µl/min across the activated surface for 25 min. The residual NHS esters were inactivated with ethanolamine (50 µl) for 10 min. A blank reference surface was also prepared with the same procedure by activation with EDC/NHS and then inactivation with ethanolamine. The affinity of the interaction was determined from the level of binding at equilibrium as a function of the sample concentrations by BIA evaluation software 3.0. The rate constant $K_D$ was obtained by fitting the sensorgram data after reference subtraction (data from blank channel) using the BIA evaluation 3.0 software.

Immunofluorescence: Cancer cells (A549, HT3, D54 and OE33) were grown on chamber slides (Millipore, USA) and incubated with 10 µg/ml FITC-GIRLRG (SEQ ID NO:1) peptide for 2 h at 37° C. in a $CO_2$ incubator. The cells were then washed with PBS to remove unbound peptide and fixed with 4% paraformaldehyde at room temperature. The nuclei were stained with DAPI and fluorescent images were captured using a Carl Zeiss microscope (Tokyo, Japan).

Radiolabeling of Peptides: The radiolabeling procedure was optimized by varying the pH, buffers, temperature, amounts of $^{111}InCl_3$ added per mg DTPA-PEG-compounds. DTPA-PEG-control and DTPA-PEG-GIRLRG (SEQ ID NO:1) stock powders were dissolved in ammonium acetate buffer (0.1M) to obtain 5 mg/ml solution. $^{111}InCl_3$ (370MBq ml$^{-1}$ in 0.5M HCl, pH 1.1-1.4) was obtained from Mallinckrodt Pharmaceuticals. Ammonium acetate (400 µl of 0.5M) was added to $^{111}InCl_3$ stock solution (450 µl) and carefully mixed; the final pH should be between 5.5-5.8. The $^{111}InCl_3$ was then added to the DTPA-PEG-control, and DTPA-PEG-GIRLRG (SEQ ID NO:1) at a ratio of 370:1 kBq:µg and the reaction mixture was incubated at 95° C. with constant shaking for 1 h. The radiolabeling efficiency of the PEG peptides was determined using instant thin-layer chromatography and labeled peptides ≥95% was used for in vivo studies. Dynamic light scattering (DLS) studies were performed with the pegylated peptides to confirm the absence of aggregates or changes in size (data not shown).

Mice: All animal studies were performed in accordance with the guidelines of the IACUC and in accordance with protocols approved by the Washington University Division of Comparative Medicine. Tumor models were established in 6 to 8-week-old female athymic nude mice obtained from Harlan laboratories (USA). Heterotopic tumors were induced by sub-cutaneously injecting tumor cells ($1-3 \times 10^6$) into hind limbs of athymic nude mice. The tumors were grown until a size of 1 cm$^3$ before using the mice for SPECT imaging.

Nano CT/SPECT Imaging and Biodistribution Studies: Mice (n=3 per group) were injected intravenously with approximately 500 µCi $^{111}$In-DTPA-PEG-GIRLRG (SEQ ID NO:1) or PEG-control in a volume of 100 µl. Whole body SPECT images were obtained at 48 and 72 h post injection (p.i.) using a NanoSPECT/CT imager (Bioscan Inc., Washington, D.C., USA) fitted with 2 mm pinhole collimators in helical scanning mode. Mice were placed in prone position and scanned under anesthesia (0.5 L/min 1.5% isoflurane in air). A 45-keV helical CT scan was performed first and then the SPECT acquisition was performed at 24 projections and 60 s per projection, for a total scan time of about 45 min. Tomographic data were reconstructed iteratively with the manufacturer-supplied InVivoScope and HiSPECT software for CT and SPECT, respectively.

After scanning, 96 h p.i., the bio-distribution of the labelled peptide in various organs was determined. The animals were sacrificed and organs of interest including blood were dissected/collected, weighed, and counted in a gamma counter along with a standard of the injected activity to allow calculation of the injected dose per organ (% ID/organ).

Statistical Analysis: Quantitative data are expressed as mean±SD. Means were compared using the Student t test. P values of less than 0.05 were considered statistically significant.

REFERENCES FOR EXAMPLES 4-8

[1] A. B. de Barros, A. Tsourkas, B. Saboury, V. N. Cardoso, A. Alavi, Emerging role of radiolabeled nanoparticles as an effective diagnostic technique, EJNMMI research, 2 (2012) 39.
[2] M. Schottelius, H. J. Wester, Molecular imaging targeting peptide receptors, Methods, 48 (2009) 161-177.
[3] R. J. Passarella, D. E. Spratt, A. E. van der Ende, J. G. Phillips, H. Wu, V. Sathiyakumar, L. Zhou, D. E. Hallahan, E. Harth, R. Diaz, Targeted nanoparticles that deliver a sustained, specific release of Paclitaxel to irradiated tumors, Cancer research, 70 (2010) 4550-4559.
[4] A. S. Lee, GRP78 induction in cancer: therapeutic and prognostic implications, Cancer research, 67 (2007) 3496-3499.
[5] Y. Zhang, R. Liu, M. Ni, P. Gill, A. S. Lee, Cell surface relocalization of the endoplasmic reticulum chaperone and unfolded protein response regulator GRP78/BiP, The Journal of biological chemistry, 285 (2010) 15065-15075.

[6] A. Delpino, M. Castelli, The 78 kDa glucose-regulated protein (GRP78/BIP) is expressed on the cell membrane, is released into cell culture medium and is also present in human peripheral circulation, Bioscience reports, 22 (2002) 407-420.

[7] M. Triantafilou, D. Fradelizi, K. Triantafilou, Major histocompatibility class one molecule associates with glucose regulated protein (GRP) 78 on the cell surface, Human immunology, 62 (2001) 764-770.

[8] M. A. Arap, J. Landenranta, P. J. Mintz, A. Hajitou, A. S. Sarkis, W. Arap, R. Pasqualini, Cell surface expression of the stress response chaperone GRP78 enables tumor targeting by circulating ligands, Cancer cell, 6 (2004) 275-284.

[9] Y. Fu, A. S. Lee, Glucose regulated proteins in cancer progression, drug resistance and immunotherapy, Cancer biology & therapy, 5 (2006) 741-744.

[10] P. J. Mintz, J. Kim, K. A. Do, X. Wang, R. G. Zinner, M. Cristofanilli, M. A. Arap, W. K. Hong, P. Troncoso, C. J. Logothetis, R. Pasqualini, W. Arap, Fingerprinting the circulating repertoire of antibodies from cancer patients, Nature biotechnology, 21 (2003) 57-63.

[11] M. Wisniewska, T. Karlberg, L. Lehtio, I. Johansson, T. Kotenyova, M. Moche, H. Schuler, Crystal structures of the ATPase domains of four human Hsp70 isoforms: HSPA1L/Hsp70-hom, HSPA2/Hsp70-2, HSPA6/Hsp70B', and HSPA5/BiP/GRP78, PloS one, 5 (2010) e8625.

[12] J. M. Wang, P. Cieplak, P. A. Kollman, How well does a restrained electrostatic potential (RESP) model perform in calculating conformational energies of organic and biological molecules?, J Comput Chem, 21 (2000) 1049-1074.

[13] V. Kapoor, A. K. Singh, S. Dey, S. C. Sharma, S. N. Das, Circulating cycloxygenase-2 in patients with tobacco-related intraoral squamous cell carcinoma and evaluation of its peptide inhibitors as potential antitumor agent, Journal of cancer research and clinical oncology, 136 (2010) 1795-1804.

[14] M. Fani, H. R. Maecke, S. M. Okarvi, Radiolabeled peptides: valuable tools for the detection and treatment of cancer, Theranostics, 2 (2012) 481-501.

[15] V. Rufini, M. L. Calcagni, R. P. Baum, Imaging of neuroendocrine tumors, Seminars in nuclear medicine, 36 (2006) 228-247.

[16] V. Ambrosini, M. Fani, S. Fanti, F. Forrer, H. R. Maecke, Radiopeptide imaging and therapy in Europe, Journal of nuclear medicine: official publication, Society of Nuclear Medicine, 52 Suppl 2 (2011) 42S-55S.

[17] G. A. Kaltsas, D. Papadogias, P. Makras, A. B. Grossman, Treatment of advanced neuroendocrine tumours with radiolabelled somatostatin analogues, Endocrine-related cancer, 12 (2005) 683-699.

[18] Y. Ma, L. M. Hendershot, The role of the unfolded protein response in tumour development: friend or foe?, Nature reviews. Cancer, 4 (2004) 966-977.

[19] Y. Liu, S. C. Steiniger, Y. Kim, G. F. Kaufmann, B. Felding-Habermann, K. D. Janda, Mechanistic studies of a peptidic GRP78 ligand for cancer cell-specific drug delivery, Molecular pharmaceutics, 4 (2007) 435-447.

[20] M. Gonzalez-Gronow, S. J. Kaczowka, S. Payne, F. Wang, G. Gawdi, S. V. Pizzo, Plasminogen structural domains exhibit different functions when associated with cell surface GRP78 or the voltage-dependent anion channel, The Journal of biological chemistry, 282 (2007) 32811-32820.

[21] A. Raiter, C. Weiss, Z. Bechor, I. Ben-Dor, A. Battler, B. Kaplan, B. Hardy, Activation of GRP78 on endothelial cell membranes by an ADAM15-derived peptide induces angiogenesis, Journal of vascular research, 47 (2010) 399-411.

[22] M. Gonzalez-Gronow, M. Cuchacovich, C. Llanos, C. Urzua, G. Gawdi, S. V. Pizzo, Prostate cancer cell proliferation in vitro is modulated by antibodies against glucose-regulated protein 78 isolated from patient serum, Cancer research, 66 (2006) 11424-11431.

[23] D. Maddalo, A. Neeb, K. Jehle, K. Schmitz, C. Muhle-Goll, L. Shatkina, T. V. Walther, A. Bruchmann, S. M. Gopal, W. Wenzel, A. S. Ulrich, A. G. Cato, A peptidic unconjugated GRP78/BiP ligand modulates the unfolded protein response and induces prostate cancer cell death, PloS one, 7 (2012) e45690.

[24] Y. Yamamoto, Y. Tsutsumi, T. Mayumi, Molecular design of bioconjugated cell adhesion peptide with a water-soluble polymeric modifier for enhancement of antimetastatic effect, Current drug targets, 3 (2002) 123-130.

[25] P. Bailon, C. Y. Won, PEG-modified biopharmaceuticals, Expert opinion on drug delivery, 6 (2009) 1-16.

The invention claimed is:

1. A composition, the composition comprising a peptide construct, wherein the peptide construct comprises:

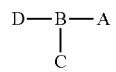

wherein
A is a peptide that specifically binds to an epitope exposed on an irradiated tumor cell, wherein A is GIRLRG (SEQ ID NO:1);
B is a linker comprising at least three amino acids, wherein at least one of the amino acids is selected from the group consisting of lysine, tyrosine, histidine and cysteine;
C is at least one chelator conjugated to B; and
D is polyethylene glycol (PEG).

2. The composition of claim 1, wherein D is selected from the group consisting of PEG20 and PEG40.

3. The composition of claim 1, wherein B comprises at least three lysine.

4. The composition of claim 1, wherein B further comprises one or more 2-aminoethoxy-2-ethoxy acetic acid (AEEA) linkers.

5. The composition of claim 3, wherein C is conjugated to one of the lysine residues.

6. The composition of claim 1, wherein C is diethylenetriaminepentaacetic acid (DTPA).

7. The composition of claim 1, wherein the composition further comprises a radionuclide complexed with C.

8. The composition of claim 7, wherein the radionuclide is selected from the group consisting of copper-64, zirconium-89, yttrium-90, indium-111, and lutetium-177.

9. The composition of claim 1, wherein B is four amino acids and three of the four amino acids are lysine, C is DTPA and is conjugated to each lysine, and D is PEG40.

10. A method of detecting a tumor in a subject, the method comprising:
a) exposing a target area of the subject where the presence of a tumor is suspected to ionizing radiation;
b) administering to the subject a composition comprising a peptide construct, wherein the peptide construct comprises:

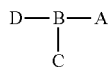

wherein
A is a peptide that specifically binds to an epitope exposed on an irradiated tumor cell, wherein A is GIRLRG (SEQ ID NO:1);
B is a linker comprising at least three amino acids, wherein at least one of the amino acids is selected from the group consisting of lysine, tyrosine, histidine and cysteine;
C is at least one chelator conjugated to B and complexed with a radionuclide; and
D is polyethylene glycol (PEG); and c) detecting the radionuclide to detect binding of the peptide to a cell in the subject, wherein the presence of the radionuclide indicates the presence of a tumor in the target area of the subject.

11. The composition of claim 10, wherein B is four amino acids and three of the four amino acids are lysine, C is DTPA and is conjugated to each lysine, and D is PEG40.

12. The method of claim 10, wherein the exposing comprises exposing the tumor to at least about 2 Gy ionizing radiation.

13. The method of claim 10, wherein the administering comprises administering the composition 0 hours to about 24 hours following radiation exposure.

14. The method of claim 10, wherein the detecting comprises detecting the radionuclide using positron emission tomography, single photon emission computed tomography, gamma camera imaging, or rectilinear scanning.

15. The method of claim 10, wherein the tumor is selected from the group consisting of an esophageal carcinoma, a glioma, a cervical carcinoma, a lung carcinoma and a breast carcinoma.

16. A method for enhancing radiotherapy in a subject, the method comprising administering to the subject a composition comprising a peptide construct, wherein the peptide construct comprises:

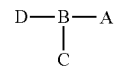

wherein
A is a peptide that specifically binds to an epitope exposed on an irradiated tumor cell, wherein A is GIRLRG (SEQ ID NO:1);
B is a linker comprising at least three amino acids, wherein at least one of the amino acids is selected from the group consisting of lysine, tyrosine, histidine and cysteine;
C is at least one chelator conjugated to B and complexed with a radionuclide;
D is polyethylene glycol (PEG).

17. The composition of claim 16, wherein B is four amino acids and three of the four amino acids are lysine, C is DTPA and is conjugated to each lysine, and D is PEG40.

18. The method of claim 16, wherein the subject has cancer.

19. The method of claim 18, wherein the cancer is selected from the group consisting of esophageal cancer, glioma, cervical cancer, lung cancer and breast cancer.

* * * * *

```
                       SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: SYNTHESIZED

<400> SEQUENCE: 1

Gly Ile Arg Leu Arg Gly
1               5
```